(12) United States Patent
Loozen et al.

(10) Patent No.: US 8,071,587 B2
(45) Date of Patent: Dec. 6, 2011

(54) (DIHYDRO)IMIDAZOISO[5,1-A]QUINOLINES

(75) Inventors: Hubert Jan Jozef Loozen, Oss (NL); Cornelius Marius Timmers, Oss (NL)

(73) Assignee: N. V. Organon, Oss (NL)

( * ) Notice: Subject to any disclaimer, the term of this patent is extended or adjusted under 35 U.S.C. 154(b) by 9 days.

(21) Appl. No.: 12/786,996

(22) Filed: May 25, 2010

(65) Prior Publication Data
US 2010/0324021 A1 Dec. 23, 2010

Related U.S. Application Data

(60) Provisional application No. 61/181,485, filed on May 27, 2009.

(51) Int. Cl.
C07D 471/04 (2006.01)
C07D 519/00 (2006.01)
A61K 31/4745 (2006.01)
A61P 15/08 (2006.01)

(52) U.S. Cl. .......... 514/211.08; 514/211.15; 514/217.05; 514/232.8; 514/253.03; 514/292; 540/492; 540/544; 540/575; 540/597; 544/126; 544/361; 546/85; 546/86

(58) Field of Classification Search .................. 540/492, 540/544, 575, 597; 544/126, 361; 546/85, 546/86; 514/211.08, 211.15, 217.05, 232.8, 514/253.03, 292
See application file for complete search history.

(56) References Cited

U.S. PATENT DOCUMENTS

| | | | |
|---|---|---|---|
| 6,906,080 B1 | 6/2005 | Barth et al. | |
| 7,858,794 B2 | 12/2010 | Timmers et al. | |
| 2002/0147345 A1 | 10/2002 | El Tayer et al. | |
| 2008/0262033 A1 | 10/2008 | Karstens et al. | |
| 2008/0275042 A1 | 11/2008 | Grima Poveda et al. | |
| 2008/0300270 A1 | 12/2008 | Timmers et al. | |
| 2009/0215773 A1 | 8/2009 | Van Straten et al. | |
| 2011/0028450 A1 | 2/2011 | Timmers et al. | |
| 2011/0028451 A1 | 2/2011 | Timmers et al. | |
| 2011/0039832 A1 | 2/2011 | van Rijn et al. | |

FOREIGN PATENT DOCUMENTS

| | | |
|---|---|---|
| WO | 00/08015 A2 | 2/2000 |
| WO | 00/08015 A3 | 2/2000 |
| WO | 02/09706 A1 | 2/2002 |
| WO | 03/004028 A1 | 1/2003 |
| WO | 2004/014917 A2 | 2/2004 |
| WO | 2004/014917 A3 | 2/2004 |
| WO | 2004/031182 A1 | 4/2004 |
| WO | 2004/056780 A2 | 7/2004 |
| WO | 2004/056780 A3 | 7/2004 |
| WO | 2005/087765 A1 | 9/2005 |
| WO | 2006/117023 A1 | 11/2006 |
| WO | 2006/117368 A1 | 11/2006 |
| WO | 2006/117370 A1 | 11/2006 |
| WO | 2006/117371 A1 | 11/2006 |
| WO | 2009/098283 A1 | 8/2009 |

OTHER PUBLICATIONS

Guo, T., "Small molecule agonists and antagonists for the LH and FSH receptors", Expert Opin. Ther. Patents, 2005, p. 1555-1564, vol. 15, No. 11.
Navot, D. et al., "The Use of Follicle-Stimulating Hormone for Controlled Ovarian Hyperstimulation in Vitro Fertilization", Journal of in Vitro Fertilization and Embryo Transfer, 1988, p. 3-13, vol. 5, No. 1.
Olijve, W. et al., "Molecular biology and biochemistry of human recombinant follicle stimulating hormone (Puregon)", Molecular Human Reproduction, 1996, p. 371-382, vol. 2, No. 5.
Sharpe, R. M., "Intratesticular Control of Steroidogenesis", Clinical Endocrinology, 1990, p. 787-807, vol. 33.
Morse, J. H. et al., "Heterogeneity of Proteins in Commercial Preparations of Human Chorionic Gonadotropin (hCG) Demonstrated by Western Blotting", American Journal of Reproductive Immunology, 1988, p. 134-140, vol. 17.
Devroey, P. et al., "Successful in-vitro fertilisation and embryo transfer after treatment with recombinant human FSH", The Lancet, 1992, p. 1170-1171, vol. 339.
Dorrington, J. H. et al., "Effects of FSH on Gonadal Functions", Recent Progress in Hormone Research, 1979, p. 300-342, vol. 35.
Insler, V. et al., "Gonadotropin Therapy: New Trends and Insights", Int/Fertil, 1988, p. 85-97, vol. 33, No. 2.

*Primary Examiner* — Bruck Kifle
(74) *Attorney, Agent, or Firm* — Janet E. Fair; John C. Todaro

(57) ABSTRACT

The invention relates to imidazoiso[5,1-a]quinoline and 5,6-dihydro-imidazoiso[5,1-a]quinoline derivatives according to general Formula I

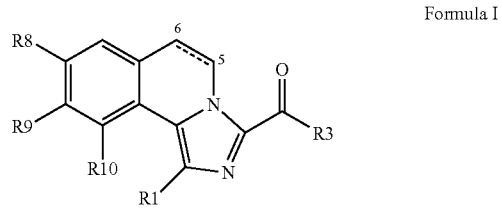

Formula I or a pharmaceutically acceptable salt thereof. The compounds can be used for the treatment of infertility.

19 Claims, No Drawings

(DIHYDRO)IMIDAZOISO[5,1-A]QUINOLINES

FIELD OF THE INVENTION

The present invention relates to imidazoiso[5,1-a]quinoline and 5,6-dihydro-imidazoiso[5,1-a]quinoline derivatives, to pharmaceutical compositions comprising the same and to the use of said compounds for the manufacture of medicaments for the treatment of infertility.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone), for example, plays a pivotal role in the stimulation of follicle development and maturation whereas LH (luteinizing hormone) induces ovulation [Sharp, R. M. Clin Endocrinol. 33, 787-807 (1990); Dorrington and Armstrong, Recent Prog. Horm. Res. 35, 301-342 (1979)]. Currently, FSH is applied clinically for ovarian stimulation, i.e. controlled ovarian stimulation for in vitro fertilisation (IVF) and induction of ovulation in infertile anovulatory women [Insler, V., Int. J. Fertility 33, 85-97 (1988), Navot and Rosenwaks, J. Vitro Fert. Embryo Transfer 5, 3-13 (1988)], as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity [Morse et al, Amer. J. Reproduct. Immunol. and Microbiology 17, 143 (1988)]. Alternatively, they can be prepared as recombinant gonadotropins. Recombinant human FSH is available commercially and is being used in assisted reproduction [Olijve et al. Mol. Hum. Reprod. 2, 371-381 (1996); Devroey et al. Lancet 339, 1170-1171 (1992)].

The actions of the FSH hormone are mediated by a specific membrane receptor that is a member of the large family of G-protein coupled receptors. These receptors consist of a single polypeptide with seven transmembrane domains and are able to interact with the Gs protein, leading to the activation of adenylate cyclase.

The FSH receptor (FSHR) is a highly specific target in the ovarian follicle growth process and is exclusively expressed in the ovary. Low molecular weight FSHR agonists can be used for the same clinical purposes as native FSH, i.e. for the treatment of infertility and for controlled ovarian stimulation preceeding in vitro fertilisation.

Certain tetrahydroquinoline derivatives have recently been disclosed in the International Application WO 2003/004028 (AKZO NOBEL N.V.) as FSHR modulating substances, either having agonistic or antagonistic properties.

Low molecular weight FSH mimetics with agonistic properties were disclosed in the International Application WO 2000/08015 (Applied Research Systems ARS Holding N.V.); WO 2004/031182 (Applied Research Systems ARS Holding N.V.); WO 2002/09706 (Affymax Research Institute); WO 2005/087765 (Arena Pharmaceuticals, Inc); WO 2006/117368 (AKZO NOBEL N.V.); WO 2006/117370 (AKZO NOBEL N.V.); WO 2006/117371 (AKZO NOBEL N.V.) and in WO 2006/117023 (AKZO NOBEL N.V.).

There clearly is a need for low molecular weight hormone mimetics that selectively activate the FSH receptor.

SUMMARY OF THE INVENTION

To that aim, the present invention provides imidazoiso[5,1-a]quinoline and 5,6-dihydro-imidazoiso[5,1-a]quinoline derivatives of general formula:

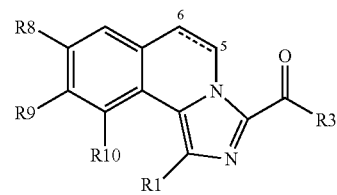

or a pharmaceutically acceptable salt thereof. The compounds can be used for the treatment of infertility.

DETAILED DESCRIPTION OF THE INVENTION

More specifically, the present invention provides dihydroimidazoiso[5,1-a]quinoline and imidazoiso[5,1-a]quinoline compounds according to formula I

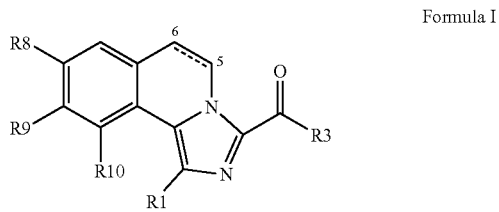

Formula I or a pharmaceutically acceptable salt thereof wherein the C5-C6 bond can either be saturated or unsaturated.

In this Formula $R^1$ through $R^{10}$ have the following definitions:

$R^1$ is phenyl or (2-5C)heteroaryl. These groups can both optionally be substituted with one or more substituents selected from $R^{13}$.

In addition $R^1$ can be (1-6C)alkyl, halogen, cyano, (2-6C)alkenyl, (2-6C)alkynyl, (3-6C)cycloalkyl, (5-6C)cycloalkenyl, (2-5C)heterocycloalkyl or (2-5C)-heterocycloalkenyl.

$R^3$ is (di)[(1-6C)alkyl]amino, optionally substituted with hydroxy or $R^3$ is a group selected from

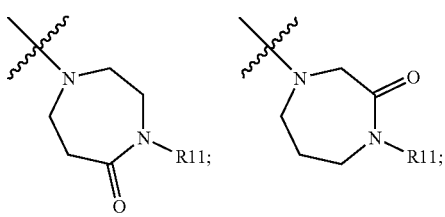

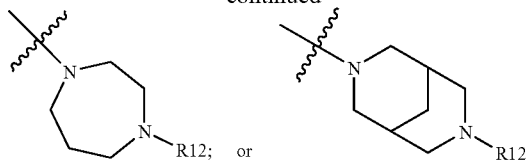

or
R³ is (1-6C)alkyl, (3-6C)cycloalkyl, (di)[(1-4C)alkyl]amino(1-4C)alkyl or
R³ is (2-6C)heterocycloalkyl, (2-6C)heterocycloalkyl(1-4C)alkyl, the (2-6C)heterocycloalkyl moiety of which optionally may be substituted with (1-4C)alkylcarbonyl or (3-6C)cycloalkylcarbonyl,
R³ is pyrrolidin-1-yl, azepin-1-yl, 1,4-oxazepin-1-yl, all optionally substituted with one or more (1-4C)alkyl substituents.
R⁸ is H, (1-4C)alkyl, (1-4C)alkoxy, (1-4C)alkoxy(1-4C)alkyl, hydroxy or (2-4C)alkenyl.
R⁹ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino, formyl, cyano, nitro, (di)[(1-4C)alkyl]aminocarboxy, (1-6C)alkylcarbonyl, (1-4C)alkoxycarbonyl, (di)[(1-4C)alkyl]amino, (di)[(1-4C)alkyl]aminocarbonylamino, (1-4C)alkoxycarbonylamino, (di)[(1-4C)alkyl]aminosulfonylamino, (1-6C)alkylthio or (1-4C)alkylsulfonylamino or
R⁹ is (1-6C)alkyl, (1-6C)alkoxy or (2-6C)alkenyl. These latter three groups can all optionally be substituted with one or more substituents selected from halogen, hydroxy, amine, azide, (1-4C)alkoxy, (1-4C)alkoxycarbonylamino or (1-4C)alkylcarbonylamino or
R⁹ is (1-5C)heteroaryl, phenyl, (2-5C)heteroaryloxy or phenoxy, all optionally substituted with one or more substituents selected from R¹⁴ or
R⁹ is (1-6C)alkylcarbonylamino, optionally substituted with hydroxy, amino, (2-5C)heterocycloalkyl or (di)[(1-4C)alkyl]amino or
R⁹ is phenyl substituted at two adjacent positions together representing a fused O—(CH₂)ₘ—O ring wherein m is 1 or 2.
R¹⁰ is H, methoxy, halogen or methyl.
R¹¹ is H, (1-4C)alkyl or (2-4C)alkenyl.
R¹² is (1-4C)alkylcarbonyl or (3-6C)cycloalkylcarbonyl, both optionally substituted with one or more substituents selected from R¹⁵.
R¹³ is hydroxy, amino, halogen, nitro, trifluoromethyl, cyano, (1-4C)alkyl, (1-4C)alkoxy, (1-4C)alkylthio or (di)[(1-4C)alkyl]amino.
R¹⁴ is hydroxy, amino, halogen, nitro, trifluoromethyl, cyano, (1-4C)alkyl, (1-4C)alkoxy, (1-4C)alkylthio, (di)[(1-4C)alkyl]amino, (2-5C)heteroaryl, (di)[(1-4C)alkyl]aminocarbonyl, (1-4C)alkylcarbonylamino or (1-4C)alkylsulfonyl or
R¹⁴ is (2-5C)heterocycloalkyl optionally substituted with (1-4C)alkyl or (1-4C)alkoxycarbonyl.
R¹⁵ in the compounds described above is hydroxy, amino, halogen, nitro, trifluoromethyl, cyano, (1-4C)alkyl, (1-4C)alkoxy, (1-4C)alkylthio or (di)[(1-4C)alkyl]amino.

The (dihydro)imidazoiso[5,1-a]quinoline derivatives according to the present invention are potent FSH receptor activators and can be used for the same clinical purposes as native FSH since they behave like agonists, with the advantage that they may be prepared synthetically, may display altered stability properties and may be administered differently. Thus, the FSH-receptor agonists of the present invention may be used for the treatment of fertility disorders e.g. controlled ovarian stimulation and IVF procedures.

The term (1-4C)alkyl as used in the definition means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (1-4C)alkylcarbonyl means an alkylcarbonyl group, the alkyl group of which contains 1-4 carbon atoms with the same meaning as previously defined.

The term (1-6C)alkylcarbonyl means an alkylcarbonyl group, the alkyl group of which contains 1-6 carbon atoms with the same meaning as previously defined.

The term (1-4C)alkylsulfonyl means an alkylsulfonyl group, the alkyl group of which contains 1-4 carbon atoms with the same meaning as previously defined.

The term (1-4C)alkylthio means an alkylthio group having 1-4 carbon atoms, the alkyl group of which contains 1-4 carbon atoms with the same meaning as previously defined.

The term (1-6C)alkylthio means an alkylthio group having 1-6 carbon atoms, the alkyl group of which contains 1-4 carbon atoms with the same meaning as previously defined. (1-5C)alkylthio groups are preferred, (1-4C)alkylthio being the most preferred.

The term (1-4C)alkylsulfonylamino means a alkylsulfonylamino group, the alkyl group of which contains 1-4 carbon atoms with the same meaning as previously defined.

The term (1-4C)alkylcarbonylamino means an alkylcarbonylamino group, the alkyl group of which contains 1-4 carbon atoms with the same meaning as previously defined.

The term (1-6C)alkylcarbonylamino means an alkylcarbonylamino group, the alkyl group of which contains 1-6 carbon atoms with the same meaning as previously defined.

The term (2-4C)alkenyl means a branched or unbranched alkenyl group having 2-4 carbon atoms, such as ethenyl and butenyl.

The term (2-6C)alkenyl means a branched or unbranched alkenyl group having 2-6 carbon atoms, such as ethenyl, 2-butenyl, and n-pentenyl.

The term (2-6C)alkynyl means a branched or unbranched alkynyl group having 2-6 carbon atoms, such as ethynyl, propynyl and n-pentynyl.

The term (3-6C)cycloalkyl means a cycloalkyl group having 3-6 carbon atoms, such as cyclopropyl, ethylcyclopropyl, cyclopropylmethyl, cyclobutyl, methylcyclobutyl, cyclopentyl and cyclohexyl.

The term (3-6C)cycloalkylcarbonyl means a cycloalkylcarbonyl group, the cycloalkyl group of which contains 3-6 carbon atoms with the same meaning as previously defined.

The term (3-6C)cycloalkoxy means a cycloalkyl group having 3-6 carbon atoms, with the same meaning as previously defined, attached via a carbon atom to an exocyclic oxygen atom.

The term (5-6C)cycloalkenyl means a cycloalkenyl group having 5-6 carbon atoms, such as cyclopentenyl, methylcyclopentenyl, cyclopentenylmethyl and cyclohexenyl.

The term (2-5C)heterocycloalkyl means a heterocycloalkyl group having 2-5 carbon atoms, preferably 3-4 carbon atoms, including 1-3 heteroatoms selected from N, O and/or S, which may be attached via a nitrogen if feasible, or a carbon atom. Preferred number of heteroatoms is 1 or 2.

Preferred are piperidin-1-yl, 1,4-diazacycloheptan-1-yl, morpholin-4-yl, tetrahydro-2H-thiopyran-4-yl, tetrahydro-2H-pyran-4-yl and pyrrolidin-1-yl. Most preferred heteroatoms are N or O. Most preferred are piperidin-1-yl, 1,4-diazacycloheptan-1-yl, morpholin-4-yl, tetrahydro-2H-pyran-4-yl pyrrolidin-1-yl and piperazin-1-yl. Even more preferred are piperidin-1-yl, 1,4-diazacycloheptan-1-yl, morpholin-4-yl and pyrrolidin-1-yl and piperazin-1-yl. Most preferred are piperidin-1-yl, 1,4-diazacycloheptan-1-yl, morpholin-4-yl and pyrrolidin-1-yl.

The term (2-6C)heterocycloalkyl means a heterocycloalkyl group having 2-6 carbon atoms, preferably 3-5 carbon atoms, including 1-3 heteroatoms selected from N, O and/or S, which may be attached via a nitrogen if feasible, or a carbon atom. Preferred heteroatoms are N or O. Preferred number of heteroatoms is one or two. Most preferred are piperidin-1-yl, 1,4-diazacycloheptan-1-yl, morpholin-4-yl, pyrrolidin-1-yl and piperazin-1-yl.

The term (2-5C)heterocycloalkenyl means a heterocycloalkenyl group having 2-5 carbon atoms, preferably 3-4 carbon atoms, including 1-3 heteroatoms selected from N, O and/or S, which may be attached via a nitrogen if feasible, or a carbon atom. Preferred number of heteroatoms is one or two. Most preferred are 3,6-dihydro-2H-pyran-4-yl and (3,6-dihydro-2H-thiopyran-4-yl.

The term (2-5C)heterocycloalkoxy means a heterocycloalkyl group which contains 2-5 carbon atoms with the same meaning as previously defined, attached via a carbon atom to an exocyclic oxygen atom.

The term (2-6C)heterocycloalkyl(1-4C)alkyl means a heterocycloalkylalkyl group, the heterocycloalkyl group of which contains 2-6 carbon atoms, preferably 3-5 carbon atoms, with the same meaning as previously defined and the alkyl group of which contains 1-4 carbon atoms with the same meaning as previously defined.

The term (2-5C)heterocycloalkylcarbonyl means a heterocycloalkylcarbonyl group, the heterocycloalkyl group of which contains 2-5 carbon atoms, preferably 3-5 carbon atoms, with the same meaning as defined previously.

The term (2-5C)heterocycloalkylcarbonylamino means a heterocycloalkylcarbonylamino group, the heterocycloalkyl group of which contains 2-5 carbon atoms, preferably 3-5 carbon atoms, with the same meaning as defined previously.

The term (1-5C)heteroaryl means an aromatic group having 1-5 carbon atoms and 1-4 heteroatoms selected from N, O and S, like imidazolyl, thiadiazolyl, pyridinyl, thienyl, tetrazolyl, oxazolyl, imidazolyl, pyrazolyl or furyl. Preferred number of heteroatoms is one or two. Preferred heteroaryl groups are thienyl, thiadiazolyl, oxazolyl, imidazolyl, tetrazolyl, pyrazolyl, pyrimidinyl, pyrazinyl, furyl and pyridinyl. Most preferred are thienyl, oxazolyl, tetrazolyl, pyrazinyl and pyridinyl. The (1-5C)heteroaryl group may be attached via a carbon atom or a nitrogen, if feasible.

The term (2-5C)heteroaryl means an aromatic group having 2-5 carbon atoms and 1-3 heteroatoms selected from N, O and S, like imidazolyl, thiadiazolyl, pyridinyl, thienyl or furyl. Preferred number of heteroatoms is one or two. Preferred heteroaryl groups are thienyl, thiadiazolyl, pyrimidinyl, pyrazinyl, pyrazolyl, oxazolyl, furyl and pyridinyl. The (2-5C)heteroaryl group may be attached via a carbon atom or a nitrogen, if feasible.

The term (2-5C)heteroarylaminocarbonyl means a heteroarylaminocarbonyl group, the heteroaryl group of which contains 2-5 carbon atoms with the same meaning and preferences as previously defined.

The term (2-5C)heteroarylcarbonylamino means a heteroarylcarbonylamino group, the heteroaryl group of which contains 2-5 carbon atoms with the same meaning and preferences as previously defined.

The term (2-5C)heteroaryloxy means a heteroaryloxy group, the heteroaryl group of which contains 2-5 carbon atoms with the same meaning and preferences as previously defined, attached via a carbon atom to an exocyclic oxygen atom.

The term (1-4C)alkoxy means an alkoxy group having 1-4 carbon atoms, the alkyl moiety having the same meaning as previously defined. (1-3C)Alkoxy groups are preferred.

The term (1-6C)alkoxy means an alkoxy group having 1-6 carbon atoms, the alkyl moiety having the same meaning as previously defined. (1-4C)Alkoxy groups are preferred.

The term (1-4C)alkoxycarbonyl means an alkoxycarbonyl group, the alkoxy group of which contains 1-4 carbon atoms with the same meaning as previously defined. (1-2C)Alkoxycarbonyl groups are preferred.

The term (1-4C)alkoxycarbonylamino means an alkoxycarbonylamino group, the alkoxy group of which contains 1-4 carbon atoms with the same meaning as previously defined.

The term (1-4C)alkoxy(1-4C)alkyl means an alkoxyalkyl group, the alkoxy group of which contains 1-4 carbon atoms with the same meaning as previously defined, which is attached to an alkyl group containing 1-4 carbon atoms with the same meaning as previously defined.

The term (di)[(1-4C)alkyl]amino as used herein means an amino group, monosubstituted or disubstituted with alkyl group(s), each containing 1-4 carbon atoms and having the same meaning as previously defined.

The term (di)[(1-4C)alkyl]aminocarbonyl means a (di)alkylaminocarbonyl group, the alkyl group(s) of which each contain(s) 1-4 carbon atoms with the same meaning as previously defined.

The term (di)[(1-4C)alkyl]aminocarboxy means a (di)alkylaminocarboxy group, the alkyl group(s) of which each contain(s) 1-4 carbon atoms with the same meaning as previously defined.

The term (di)[(1-4C)alkyl]aminocarbonylamino means a (di)alkylaminocarbonylamino group, the alkyl group(s) of which each contain(s) 1-4 carbon atoms with the same meaning as previously defined.

The term (di)(1-4C)alkylamino(1-4C)alkyl as used herein means a (di)alkylamino group, the alkyl group(s) of which each contain(s) 1-4 carbon atoms with the same meaning as previously defined, connected via the amino group to an alkyl group which contains 1-4 carbon atoms with the same meaning as previously defined.

The term (di)[(1-4C)alkyl]aminosulfonylamino means a (di)alkylaminosulfonylamino group, the alkyl group(s) of which each contain(s) 1-4 carbon atoms with the same meaning as previously defined.

The term halogen means fluorine, chlorine, bromine or iodine.

The term "substituted" means that one or more hydrogens on the designated atom is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like amine, sodium hydroxide, potassium hydroxide or lithium hydroxide.

In one aspect the invention relates to compounds of formula I wherein $R^1$ is phenyl or (2-5C)heteroaryl. These groups can both optionally be substituted with one or more substituents selected from $R^{13}$. In addition $R^1$ can be (1-6C)alkyl, halogen, cyano, (2-6C)alkenyl, (2-6C)alkynyl, (3-6C)cycloalkyl or (5-6C)cycloalkenyl.

In another aspect the invention relates to compounds of formula I wherein $R^3$ is (di)[(1-6C)alkyl]amino, optionally substituted with hydroxy or
$R^3$ is a group selected from

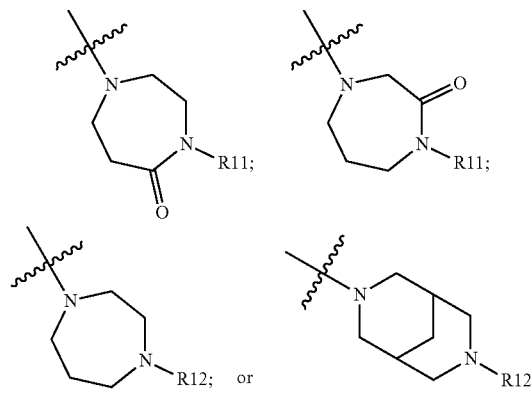

or
$R^3$ is (1-6C)alkyl, (3-6C)cycloalkyl, (di)[(1-4C)alkyl]amino(1-4C)alkyl or
$R^3$ is (2-6C)heterocycloalkyl(1-4C)alkyl, the (2-6C)heterocycloalkyl moiety of which optionally may be substituted with (1-4C)alkylcarbonyl or (3-6C)cycloalkylcarbonyl, or
$R^3$ is pyrrolidin-1-yl, azepin-1-yl, 1,4-oxazepin-1-yl, all optionally substituted with one or more (1-4C)alkyl substituents.

In another aspect the invention relates to compounds of formula I wherein the phenyl substitution in $R^9$ at the two adjacent positions is with dioxomethylene.

In another aspect the invention relates to compounds of formula I wherein $R^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino, formyl, cyano, nitro, (di)[(1-4C)alkyl]aminocarboxy, (1-6C)alkylcarbonyl, (1-4C)alkoxycarbonyl, (di)[(1-4C)alkyl]amino, (di)[(1-4C)alkyl]aminocarbonylamino, (1-4C)alkoxycarbonylamino, (di)[(1-4C)alkyl]aminosulfonylamino, (1-6C)alkylthio or (1-4C)alkylsulfonylamino or
$R^9$ is (1-6C)alkyl, (1-6C)alkoxy or (2-6C)alkenyl. These latter three groups can all optionally be substituted with one or more substituents selected from halogen, hydroxy, amine, azide, (1-4C)alkoxy, (1-4C)alkoxycarbonylamino or (1-4C)alkylcarbonylamino or
$R^9$ is (1-5C)heteroaryl, phenyl, (2-5C)heteroaryloxy or phenoxy, all optionally substituted with one or more substituents selected from $R^{14}$ or
$R^9$ is (1-6C)alkylcarbonylamino, optionally substituted with hydroxy, amino, (2-5C)heterocycloalkyl or (di)[(1-4C)alkyl]amino.

In one aspect the invention relates to compounds of formula I wherein the C5-C6 bond is not saturated.

In another aspect the invention relates to compounds of Formula I wherein the C5-C6 bond is saturated.

The invention also relates to compounds according to Formula I wherein
$R^1$ is phenyl or (2-5C)heteroaryl, both optionally substituted with one or more substituents selected from $R^{13}$ or
$R^1$ is (1-6C)alkyl;
$R^3$ is (di)[(1-6C)alkyl]amino, optionally substituted with hydroxy or
$R^3$ is a group selected from

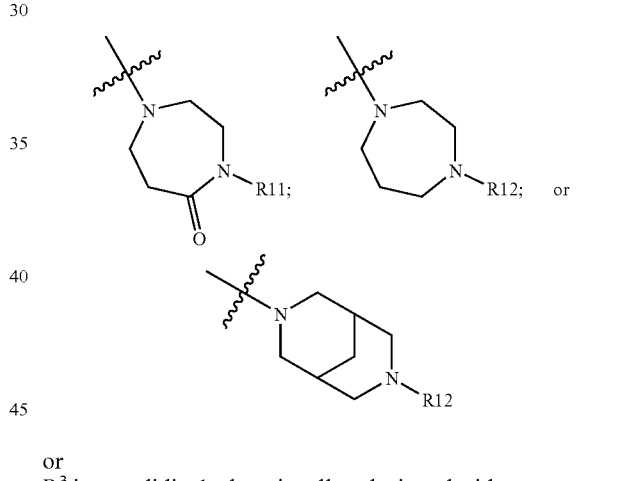

or
$R^3$ is pyrrolidin-1-yl, optionally substituted with one or more (1-4C)alkyl substituents
$R^8$ is H, (1-4C)alkyl, (1-4C)alkoxy or (2-4C)alkenyl;
$R^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino or (1-6C)alkylthio or
$R^9$ is (1-6C)alkyl, (1-6C)alkoxy or (2-6C)alkenyl, all optionally substituted with one or more substituents selected from halogen, hydroxy, amine, azide, (1-4C)alkoxy, (1-4C)alkoxycarbonylamino or (1-4C)alkylcarbonylamino or
$R^9$ is (1-5C)heteroaryl or phenyl, both optionally substituted with one or more substituents selected from $R^{14}$ or
$R^9$ is (1-6C)alkylcarbonylamino, optionally substituted with hydroxy, amino, (2-5C)heterocycloalkyl or (di)[(1-4C)alkyl]amino and
$R^{10}$ is H or halogen;
$R^{11}$ is (1-4C)alkyl or (2-4C)alkenyl;

$R^{13}$ is halogen; and $R^{14}$ is amino, halogen, trifluoromethyl, cyano, (1-4C)alkyl, (1-4C)alkoxy, (di)[(1-4C)alkyl]amino, (2-5C)heteroaryl, (di)[(1-4C)alkyl]aminocarbonyl, (1-4C)alkylcarbonylamino or (1-4C)alkylsulfonyl or $R^{14}$ is (2-5C)heterocycloalkyl optionally substituted with (1-4C)alkoxycarbonyl.

In yet another aspect the invention concerns compounds of Formula I wherein $R^1$ is (2-5C)heteroaryl.

In another aspect the invention relates to compounds of Formula I wherein $R^1$ is thien-2-yl or thiazol-5-yl.

In yet another aspect the invention relates to compounds of Formula I wherein $R^1$ is thien-2-yl.

In yet another aspect the invention relates to compounds of Formula I wherein $R^3$ is (di)[(1-6C)alkyl]amino,

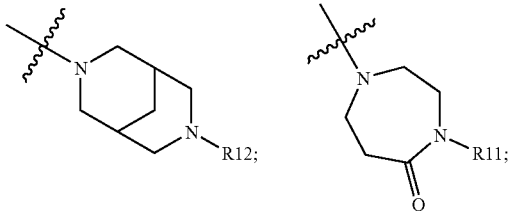

or pyrrolidin-1-yl, optionally substituted with one or more (1-4C)alkyl substituents.

In another aspect the invention relates to compounds of Formula I wherein $R^{12}$ is (3-6C)cycloalkylcarbonyl.

In another aspect the invention relates to compounds of Formula I wherein $R^8$ is (1-4C)alkoxy.

In yet another aspect the invention relates to compounds of Formula I wherein $R^9$ is (1-6C)alkoxy, optionally substituted with hydroxyl; or $R^9$ is (1-6C)alkyl; (2-4C)alkenyl; (2-5C)heteroarylaminocarbonyl; or $R^9$ is (1-6C)alkylcarbonylamino, optionally substituted with (2-5C)heterocycloalkyl; or $R^9$ is (1-5C)heteroaryl or phenyl, both optionally substituted with one or more substituents selected from $R^{14}$.

In another aspect the invention relates to compounds of Formula I wherein $R^{14}$ is amino, halogen, cyano, (1-4C)alkyl, (di)[(1-4C)alkyl]amino, (2-5C)heteroaryl, (1-4C)alkylcarbonylamino or (2-5C)heterocycloalkyl.

In yet another aspect the invention relates to compounds of Formula I wherein $R^{10}$ is H.

In yet another aspect the invention relates to compounds of Formula I wherein $R^{14}$ is amino, halogen, cyano, (1-4C)alkyl, (di)[(1-4C)alkyl]amino, (2-5C)heteroaryl, (1-4C)alkylcarbonylamino or (2-5C)heterocycloalkyl.

In another aspect the invention relates to compounds of Formula I wherein $R^1$ is thien-2-yl, $R^3$ is (di)[(1-6C)alkyl]amino and $R^8$ is (1-4C)alkoxy.

In yet another aspect the invention relates to compounds of Formula I wherein $R^8$ is methoxy.

The invention also relates to those compounds wherein all specific definitions for $R^1$ through $R^{15}$ in the various aspects of the invention as defined hereabove occur in any combination within the definition of the (dihydro)imidazoiso[5,1-a]quinoline compound of formula I.

All compounds of the invention have an $EC_{50}$ of at least 10 μM

In another aspect the invention relates to compounds of formula I which have an $EC_{50}$ of less than 100 nM. In yet another aspect the invention relates to compounds of formula I which have an $EC_{50}$ of less than 10 nM.

The term $EC_{50}$ means the concentration of the test compound that elicits half-maximal (50%) stimulation compared to the compound's maximally attainable effect. The values can be determined e.g. in a cell line transfected with a FSH receptor gene and cotransfected with a cAMP responsive element/promoter directing the expression of a reporter gene. Values can be determined using a software program such as MathIQ (version 2.0, ID Business Solutions Limited).

Suitable methods to prepare imidazoiso[5,1-a]quinoline and 5,6-dihydro-imidazoiso[5,1-a]quinoline compounds are described below.

The synthesis of the 5,6-dihydro-imidazo[5,1-a]-isoquinoline scaffold has been described in literature:

Chemical approaches to specific analogs include the double cyclization of appropriately functionalized diamides in acidic media to provide 5,6-dihydro-imidazo[5,1-a]-isoquinolines. Thus, treatment of N-{[2-(3,4-dimethoxy-phenyl)-ethylcarbamoyl]-methyl}-benzamide with phosphorous oxychloride, gives 3-phenyl-8,9-dimethoxy-dihydroimidazo[5,1-a]isoquinoline [Child et al. *J. Chem. Soc.*, 36 (1931)]. In a similar way the preparation of 1-methyl-3-phenyl-5,6-dihydro-imidazo[5,1-a]-isoquinoline was described [Elliott, *J. Org. Chem.* 27, 3302 (1962)], and 1-(3,4-methoxyphenyl)-5,6-dihydro-8,9-dimethoxy-imidazo[4,5-a]isoquinoline [Baxter et al. *J. Chem. Soc.* 3645 (1965)].

This approach was utilized to synthesize for example 3-nitrophenyl-5-alkyl-5,6-dihydro-imidazo[5,1-a]-isoquinolines and 3-furyl-, and 3-furylmethyl-5,6-dihydro-imidazo[5,1-a]-isoquinolines [Kametani et al. *Yakugaku Zasshi* 71, 325 (1951); Iida, *Yakugaku Zasshi* 80, 1127 (1960)] and for the preparation of 1-benzyl-3-phenyl-5,6-dihydro-imidazo[5,1-a]-isoquinoline [Nagarajan et al. *J. Chem. Res.* (S) 336 (1993)]. The methods described above were used for synthesis of specific 1-aminocarbonyl-3-methyl-5,6-dihydro-imidazo[5,1-a]-isoquinolines [EP0198227A2 (Boehringer Ingelheim KG)].

Alternatively, the construction of the 5,6-dihydro-imidazo[5,1-a]-isoquinoline skeleton is realized by stepwise synthesizing the rings, e.g. first formation of 3,4-dihydroisoquinoline, followed by annulations of the imidazo fragment. In this manner 3-amino-substituted 5,6-dihydro-imidazo[5,1-a]-isoquinolines [DE2742433A1 (1976) (Sandoz GmbH,); WO0021961 (The Procter & Gamble Company)] and 1-cyano-3-alkyl/phenyl-5,6-dihydro-imidazo[5,1-a]-isoquinolines [DE 2821226A (1978) (Chinoin Gyogyszer es Vegyeszeti Termemek Gyara RT)] were synthesized.

Another method includes the creation of an appropriately substituted 5-phenylimidazole first, followed by nucleophilic ring closure to the 5,6-dihydro-imidazo[5,1-a]-isoquinoline, leading to 3-phenylsulfonyl derivatives and hence 3-amino-5,6-dihydro-imidazo[5,1-a]-isoquinolines, as has been described [WO0069860; WO0069857 (The Procter & Gamble Company)]. Similarly, Heck-type ring closure was used to this end; 1-allyl-5-(2-bromophenyl)imidazoles can thus be converted to afford 1-phenyl-6-alkenyl-5,6-dihydro-imidazo[5,1-a]-isoquinolines [Beebe, et al. *Tetrahedron Letters* 47, 3225 (2006)].

Radical approaches have found limited use in order to obtain 5,6-dihydro-imidazo[5,1-a]-isoquinolines; 1-(2-bromophenyl)imidazole-4-carboxylate can be converted into 5,6-dihydro-imidazo[5,1-a]-isoquinoline-1-carboxylate [Allin et al. *Tetrahedron* 61, 2689 (2005)]. Identical approaches were employed to obtain 3-phenyl-5,6-dihydro-imidazo[5,1- a]-isoquinolines from 1-phenethyl-5-bromo-imidazole [Aldabbagh et al. *Letters Org. Chem.* 3, 510 (2006)].

The unsaturated imidazoiso[5,1-a]quinoline scaffold is known in literature:

For example, 3-(3,4-dimethoxyphenyl)-5-methyl-8,9-methylenedioxy-imidazo-iso[5,1-a]quinolines were synthesized [Kametani et al. *Yakugaku Zasshi* 71, 325 (1951)], by double cyclization-dehydration of suitable diamide precursors, along routes described above [Iida, *Yakugaku Zasshi* 80, 1127 (1960)]. Further synthetic procedures for related compounds start with the synthesis of isoquinolines containing an 1-aminomethyl function, which upon acylation and subsequent dehydration, can be converted to imidazoiso[5,1-a]quinolines. The synthesis of 3-alkyl and 3-aryl-imidazoiso[5,1-a]quinolines [Reimlinger et al. *Chem. Ber.* 108, 3771 (1975)], 1,3-di(fluoro)alkyl [Zimmer et al. *Tetrahedron Lett.* 2805 (1968)], as well as 6-alkoxy-3-(hetero)aryl imidazoiso[5,1-a]quinolines [WO0192258A1 (Neurogen Corp)] has been achieved in that way. Another approach uses a copper(II) catalyzed oxidative assembly from aminomethyl isoquinolines and aldehydes, resulting in the construction of 1-phenyl-3-(2-pyridyl)-imidazoiso[5,1-a]quinoline [Doering et al. *Angew. Chem. Int. Eng. Ed.* 41, (16) 2962 (2002)].

Here we describe compounds of formula I, and more specifically, 5,6-dihydro-imidazo[5,1-a]isoquinoline-3-carbonamides as well as their unsaturated analogs imidazoiso[5,1-a]quinoline-3-carbonamides (II). Imidazo[5,1-a]isoquinolines as well as their 5,6-dihydro-derivatives substituted with carbon amides at C3 have not been reported in literature.

We describe compounds of general formula I, the substituents of which correspond to the definitions in the claims.

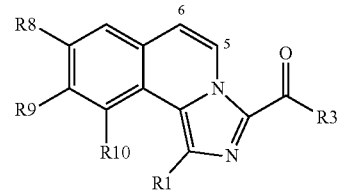

I

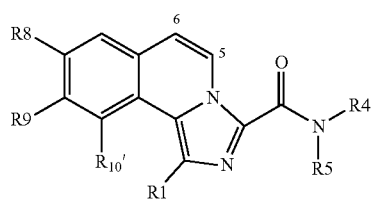

II

The synthesis of the 5,6-dihydro-imidazoiso[5,1-a]quinoline skeleton (IV) can be achieved by acid mediated ring closure of diamide precursors III. Reaction conditions become apparent from literature sources cited (vide supra) and are known to those skilled in the art for these type of procedures, like $P_2O_5$, $POCl_3$, polyphosphoric acid, methanesulphonic acid, and mixtures thereof, neat or in organic solvents, and potentially with heating.

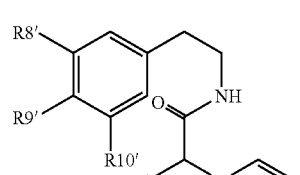

III

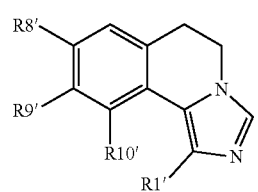

IV

The construction of diamides III can be achieved by means of condensation of suitably substituted phenethyl amines (V) with N-formyl glycines (method A). Appropriate phenethyl amines of the general formula V are either commercially available or readily prepared via e.g. chloromethylation of appropriately substituted benzenes, followed by cyanation and reduction. Another common method for the preparation of phenethyl amines is the Henry reaction, which converts aldehydes into nitrostyrenes, which upon reduction with hydride reagents provide the desired amines. Substituted glycines used are commercially available or can be synthesized via the well known Strecker reaction.

Method A

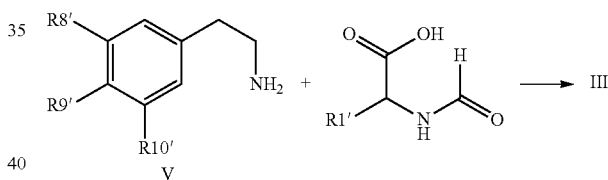

A complementary alternative approach to the diamides III employs a multicomponent reaction (in literature known as the Ugi reaction) of phenethyl isonitriles (VI), aldehydes and ammonium formate (method B). The appropriate isonitriles are easily available by dehydration of corresponding N-formylphenethylamines (prepared from phenethylamines of general formula V described before), according to standard literature procedures.

Method B

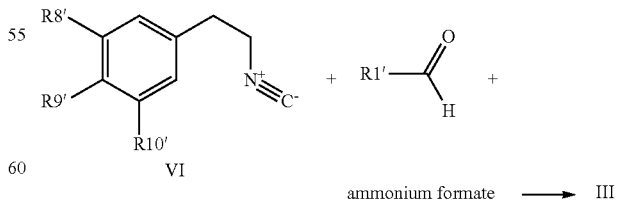

In order to introduce the amide functionality at C3, a regioselective lithiation of compounds with general formula IV, followed by in situ carboxylation and coupling of an amine can be performed, leading to 5,6-dihydro-imidazo[5,1-a]isoquinoline-3-carbonamides of general structure II. Selective lithiation at the C3 position of the scaffold can be achieved by alkyl lithium reagents like BuLi. In some cases alternative bases are used (like phenyl lithium or lithium amides like LDA, LTMP, or LiHMDS) depending on sensitivity of other substituents in the scaffold to the reaction conditions. A similar procedure may be used for introduction of ketones at the C3 position. After lithiation reaction, followed by teament with e.g. aldehydes and subsequent oxidation the required ketones are obtained.

Individual substituents of structure I, viz., R1, R8, R9, R10 may be present already at the beginning of the synthesis or can be formed at any stage estimated to be more suitable during the synthetic procedures by typical functional group transformations, which allow R1', R8', R9' and R10' to be converted separately into the desired R1, R8, R9 and R10.

In order to manipulate substituents at the C1, C8, C9, and C10 position, halogen atoms like bromine, iodine or triflates can be used. They can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles. Especially useful are these approaches for connecting heterocyclic structures to specific positions of the scaffold, e.g. by coupling of tailor made heterocyclic structures (like boronates, or stannanes).

Alternatively, the above mentioned functionalities like nitriles and carbon-carbon triple bond are further converted into heterocycles by cycloaddition reactions to afford tetrazoles and triazoles respectively [Suzuki *Chem. Comm.* 4759 (2005); Bach et al. *Tetrahedron* 61, 2245 (2005); Rossi et al. *Synthesis*, 2419 (2004); Muci and Buchwald, Practical Palladium Catalysts for C—N and C—O bond formation, in *Topics in current Chemistry-Cross coupling Reactions*, Vol 219, N. Miyaura., Ed., Springer Verlag, Heidelberg, 131-209, (2002); Hartwig, Palladium-catalyzed Amination of Aryl Halides and Related Reactions, in *Handbook of Organopalladium Chemistry for Organic Synthesis*, Vol 1, 1051-1096 (2002) E. Negishi Ed., J. Wiley & Sons: New York; Schlummer et al. *Advanced Synthesis and Catalysis,* 346, (13-15) 1599 (2004); Transition Metals for Organic Synthesis; M. Beller, C. Bolm Ed., Wiley-VCH Verlag GmbH & Co, Weinheim, Germany]. Carbon-carbon double bonds can be converted via dihydroxylation/oxidation to carboxylic acids, which can be further reacted to yield carbonamides. Alkoxy groups (like methoxy and isopropoxy) may be cleaved and reacted to give alternative ethers or reactive substituents like triflates (vide supra). Alkoxy groups (like methoxy and isopropoxy) can be dealkylated by well known electrophilic reagents (BBr$_3$, BCl$_3$, AlCl$_3$ etc) or concomitantly during cyclization conditions (III to IV, especially when R9' is isopropoxy) with methane sulfonic acid. In this last case, the product generally comprised the R9'-methylsulfonates. Saponification of the sulfonate moiety provides free phenol, which can be easily reacted to give reactive intermediates (like triflates, vide supra) or can be treated with e.g. boronic acids in the presence of copper salts to create diaryl ether bonds.

A modification of the above described approach consists of synthesis of structures IVa in which R$_1$' is H. These analogs IVa can easily be converted to 1,3-dibromo derivatives IVb by reaction with brominating agents such as bromine or NBS. These 1,3-dibromo compounds can be submitted to regioselective halogen-lithium exchange to provide 1-bromo-3-lithio compounds which undergo carboxylation/amidation to provide structures of general formula IIa (R1'=Br). The residing bromine atom can be further manipulated along the principles described above.

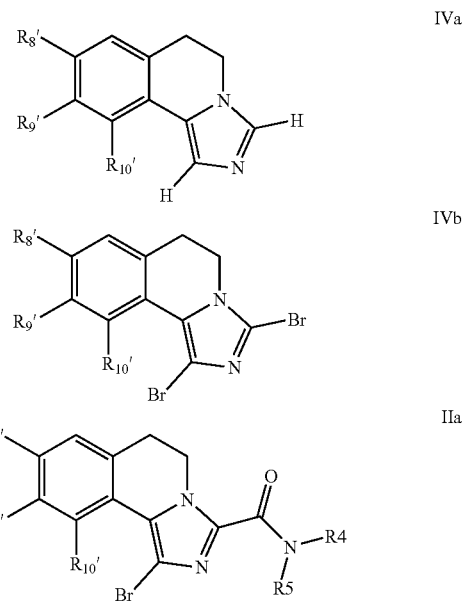

The unsaturated imidazoiso[5,1-a]quinoline-3-carbonamides of general structure VIII can be accessed by dehydrogenation of their 5,6-dihydro analogs (VII), which were prepared according to the methods described above, by means of oxidation with DDQ in appropriate solvents.

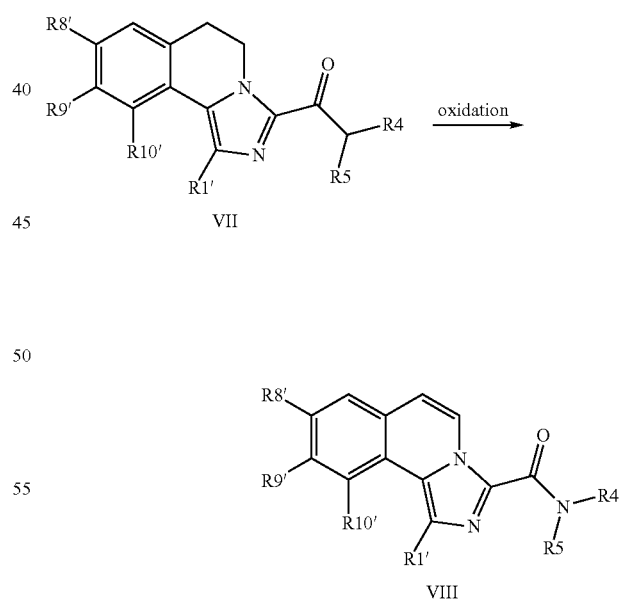

This method is not generally applicable to all desired derivatives. An efficient alternative entails the creation of suitably functionalized imidazoiso[5,1-a]quinolines (IX), which after selective lithiation and carboxylation (vide supra) can be converted into imidazoiso[5,1-a]isoquinoline-3-carbonamides VIII.

IX

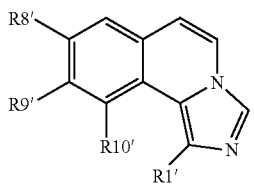

The imidazoiso[5,1-a]quinolines (IX) can be synthesized according to the method described below: 3,4-dihydro-isoquinolines (X), available by Bischler-Napieralsky type reactions [Orito et al. *J. Org. Chem.* 64, 6583 (1962); Bermejo et al. *J. Med. Chem.* 45, 5058, (2002)], are oxidized at the α-imine position to give ketones XI. A number of methods have been described for related systems, such as base catalyzed [Bermejo et al. *J. Med. Chem.* 45, 5058, (2002); Cho, et al. *J. Het. Chem.*, 36, 1151 (1999)] or palladium catalyzed air oxidation [Andreu et al. *Tetrahedron Lett.* 43, 757 (2002)], the use of dichromate [Weisbach et al. *Med. Chem.*, 11, 752 (1968)] or singlet oxygen [Martin et al. *Helv. Chim. Acta.*, 64, 2189 (1981)]. Subsequently, dehydrogenation to XII is performed by heating in the presence of Pd on carbon in high boiling solvents. Conversion of compounds XII to oximes is followed by reduction to give the desired aminomethyl derivatives XIII. Such functional group transformations to amino derivatives are well known to those skilled in the art. This reduction can be accomplished with the use of catalytic reduction with RaNi [Reimlinger et al. *Chem. Ber.* 108, 3771 (1975)] or the use of dissolving metal reduction with Zn [Niemers et al. Synthesis 593 (1976)]. Formylation of compounds with the general formula XIII to give XIV, followed by dehydration affords the desired derivatives of formula IX.

The desired substituents can be introduced by following identical strategies as indicated here above for the related 5,6-dihydro analogs.

X

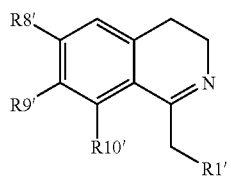

XI

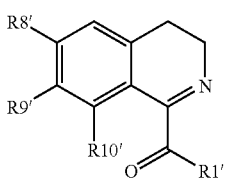

XII

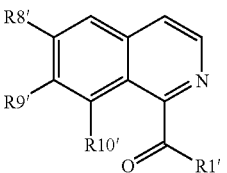

-continued

XIII

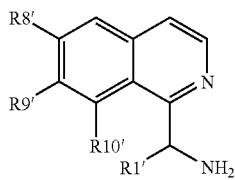

XIV

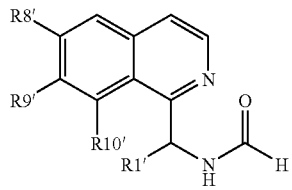

XV

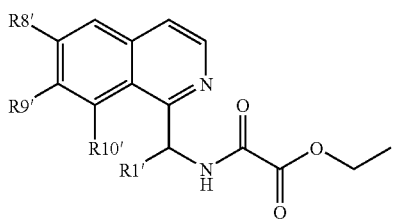

An alternative approach is the construction of imidazoiso[5,1-a]quinoline-3-carboxylates XVI directly by ring closure of appropriately functionalized N-oxalates (XV) instead of N-formates XIV. These can be converted directly in the desired derivatives of general structure II and I by reaction with appropriate amidation reagents.

XVI

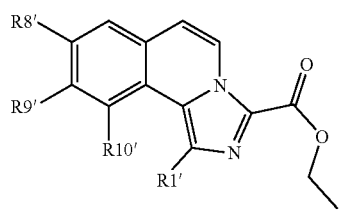

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{11}C$, $^{13}C$, $^{14}C$, $^{15}N$, $^{18}O$, $^{17}O$, $^{35}S$, $^{18}F$, and $^{36}Cl$, respectively.

Certain isotopically-labelled compounds of Formula (I) (e.g., those labeled with $^3H$, $^{14}C$, $^{18}F$ and $^{11}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The (dihydro)imidazoiso[5,1-a]quinoline compounds of the invention were found to stimulate the FSH receptor. Methods to determine receptor binding, as well as in vitro and in vivo assays to determine biological activity, of gonadotropins are well known. In general, expressed receptor is incubated with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, *Mol. Endocrin.*, 5, 759-776, (1991)).

Methods to construct recombinant FSH receptor expressing cell lines are well known in the art (Sambrook et al., Molecular Cloning: a Laboratory Manual, Cold Spring Harbor Laboratory Press, Cold Spring Harbor). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding of the test compound, or stimulation of a functional response.

Alternatively, isolated cell membranes containing the expressed receptor may be used to measure binding of the test compound.

For measurement of binding, radioactive or fluorescent compounds may be used. Such compounds are also part of the invention.

In the alternative also competition binding assays may be performed.

Another assay involves screening for FSH receptor agonistic compounds by determining stimulation of receptor mediated cAMP accumulation. Thus, such a method involves expression of the receptor in a host cell and exposing the cell to the test compound. The amount of cAMP is then measured. The level of cAMP will be increased, by the stimulating effect of the test compound upon binding to the receptor.

For the measurement of intrinsic activity human recombinant FSH can be used as a reference compound.

In addition to direct measurement of e.g. cAMP levels in the exposed cell, cells lines can be used which in addition to transfection of DNA encoding the FSH receptor are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., *Curr. Opin. Biotechnol.*, 6, 574-581 (1995).

The present invention also relates to a pharmaceutical composition comprising a (dihydro)imidazoiso[5,1-a]quinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, pulmonary, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The compounds according to the invention can be used in therapy. They can be used for the same clinical purposes as the native FSH.

A further aspect of the invention resides in the use of (dihydro)imidazoiso[5,1-a]quinoline compounds having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of (dihydro)imidazoiso[5,1-a]quinoline compounds having the general formula I for the manufacture of a medicament to be used for the treatment of infertility. In particular the compounds can be used to induce ovulation (OI) or in controlled ovarian stimulation (COS) protocols.

The invention is illustrated by the following examples:

EXAMPLES

General Comments

The following abbreviations are used in the examples: DIPEA=N,N-diisopropylethylamine, TFA=trifluoroacetic acid, HATU=O-(7-azabenzotriazole-1-yl)-N,N,N',N'-tetramethyl-uronium hexafluorophosphate, DMF=N,N-dimethyl-formamide, DME=1,2-dimethoxyethane, DMSO=dimethylsulfoxide, DCC=dicyclohexylcarbodiimide, LiHMDS=lithium hexamethyldisilazide, MOMCl=methoxymethylchloride, THF=tetrahydrofuran, NMP=N-methylpyrrolidone, TBTU=O-benzotriazol-1-yl-N,N,N,N'-tetrabutyluronium tetrafluoroborate, BOP=(benzotriazol-1-yloxy)tris(dimethylamino)-phosphonium hexafluorophosphate, HOBt=1-hydroxybenzotriazole hydrate, DMAP=4-(dimethylamino)pyridine, PS—PPh$_3$=solid-phase-triphenylphosphine. BuLi=butyl lithium.

Unless stated otherwise, all final products of the examples below were lyophilized from water/1,4-dioxane, water/tert-butanol or water/acetonitrile mixtures. If the compound was prepared as a TFA salt, the acid was added in an appropriate amount to the solvent mixture before lyophilization.

The names of the final products described in the examples were generated using the Beilstein Autonom program (version: 2.02.304).

The following preparative HPLC system was used for purification:
5 μm Luna C18(2) 150×21.2 mm column with water/acetonitrile mixtures, optionally in the presence of 0.1% aqueous TFA, using the indicated gradient. Flow: 20 ml/min: detection: 210 nm: runtime: 30 minutes.

Microwave reactions were carried out on a Biotage (model: Initiator) microwave oven with autosampler.

Thin Layer Chromatograpy (TLC) was conducted on Merck TLC plates (5×10 cm) silica gel 60 F$_{254}$.

Example 1

9-Bromo-8-methoxy-1-thiophen-2-yl-5,6-dihydro-imidazo[5,1-a]isoquinoline-3-carboxylic acid tert-butyl-methyl-amide (a). 3-Methoxy-4-nitro-benzaldehyde A mixture of 3-hydroxy-4-nitrobenzaldehyde (51.3 g), iodomethane (38.3 ml) and K$_2$CO$_3$ (85 g) in DMF (250 ml) was stirred at 60° C. for 1 h. The reaction mixture was cooled to room temperature and poured into water (600 ml). The solids were collected by filtration and dried in vacuo (50° C.).
Yield: 49.7 g. $^1$H-NMR (CDCl$_3$) δ 4.04 (s, 3H, OCH$_3$), 7.55, 7.6, 7.9 (m, 3H, ArH), 10.08 (s, 1H, CHO).

(b). 4-Amino-3-methoxy-benzaldehyde

Iron powder (112 g) was added to a mixture of the product of example 1a (49.7 g) and ammonium chloride (103 g) in aqueous ethanol (1000 ml 50%). After stirring with a mechanical stirrer at 78° C. for 2 h, the reaction mixture was cooled to room temperature and extracted with diethyl ether (3×500 ml). The combined organic layers were concentrated in vacuo and water (400 ml) was added to the residue. The solids were collected by filtration and dried in vacuo (50° C.).
Yield: 38.3 g. $^1$H-NMR (CDCl$_3$): δ 3.9 (s, 3H, OCH$_3$), 4.5 (br. s, 2H, NH$_2$), 6.75-7.3 (m, 3H, ArH), 9.75 (s, 1H, CHO).

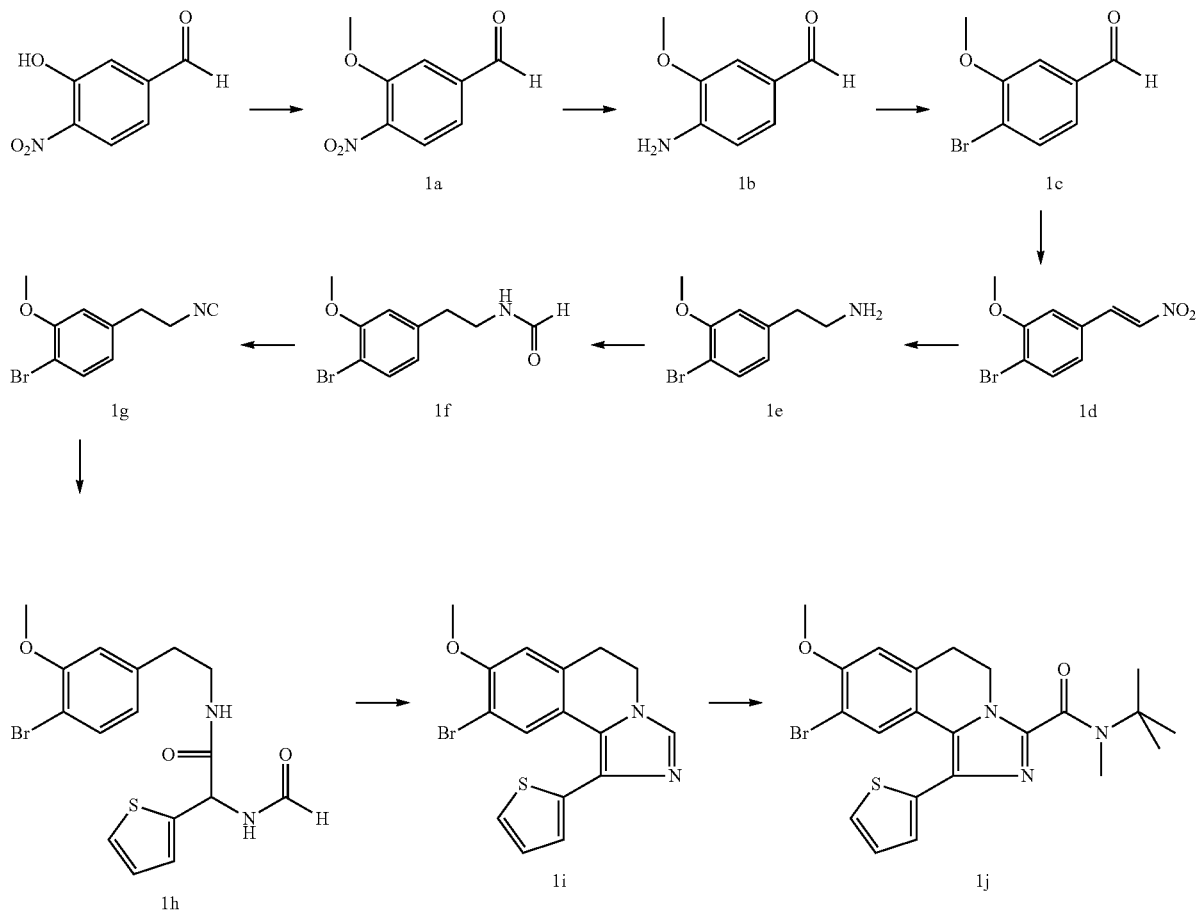

(c). 4-Bromo-3-methoxy-benzaldehyde

A solution of the product of example 1b (38.3 g) in acetonitrile (600 ml) was added drop wise to a mixture of n-butyl nitrite (43.1 ml) and copper(I) bromide (63.6 g) in acetonitrile (1.3 l). After stirring for 18 h at room temperature, the reaction mixture was diluted with ethyl acetate and washed with an aqueous HCl solution (1 N). The organic layer was separated and washed with brine, dried ($MgSO_4$), filtered and concentrated in vacuo. The residue was purified by chromatography on silica gel in heptane/ethyl acetate [1:1 (v/v)].

Yield: 27.4 g. LC/MS-ESI: $[M+H]^+$=215.1/217.0; $^1$H-NMR ($CDCl_3$): δ 3.98 (s, 3H, OMe), 7.32, 7.4, 7.75 (m, 3H, ArH), 9.95 (s, 1H, CHO).

(d). 1-Bromo-2-methoxy-4-((E)-2-nitro-vinyl)-benzene

A mixture of the product of example 1c (27.4 g), ammonium acetate (10.8 g) and nitromethane (35 ml) in acetic acid (125 ml) was stirred at 80° C. for 18 h. The reaction mixture was cooled to room temperature and poured into water (1 l). The solids were collected by filtration and dissolved in dichloromethane (2 l). The organic layer was washed with brine, dried ($MgSO_4$), filtered and concentrated in vacuo.

Yield: 29.8 g. $^1$H-NMR ($CDCl_3$): δ 3.95 (s, 3H, $OCH_3$), 7.0-7.95 (m, 5H, ArH+CH=CH).

(e). 2-(4-Bromo-3-methoxy-phenyl)-ethylamine

At 0° C. and under a nitrogen atmosphere, a solution of borane-THF complex (262 ml 1M) was added drop wise to a solution of the product of example 1d (15 g) in THF (250 ml). After the addition, the ice bath was removed. Sodium borohydride (0.11 g) was added (a slight exothermic reaction took place). After stirring for 18 h at 65° C. ($N_2$), the reaction mixture was cooled to room temperature and poured in an HCl solution (250 ml 2 N). After stirring for 1.5 h at 70° C., the reaction mixture was cooled to room temperature and extracted twice with diethyl ether. The aqueous layer was made basic with solid NaOH until pH=10 and extracted three times with ethyl acetate. The combined organic layers were washed with brine, dried ($MgSO_4$), filtered and concentrated in vacuo.

Yield: 13.5 g. LC/MS-ESI: $[M+H]^+$=230.1/232.1; $^1$H-NMR ($CDCl_3$): δ 2.92 (t, 2H, —$CH_2$), 2.97 (q, 2H, —$CH_2$N), 3.9 (s, 3H, $OCH_3$), 6.68, 6.72, 7.43 (m, 3H, ArH).

(f). N-[2-(4-Bromo-3-methoxy-phenyl)-ethyl]-formamide

The product of example 1e (21.0 g) was heated at 70° C. in ethyl formate (150 ml) for 5 h. The reaction mixture was concentrated in vacuo affording the crude product which was used as such in the next step.

Yield: 21.2 g. $^1$H-NMR ($CDCl_3$): δ 2.82 (t, 2H, —$CH_2$), 3.58 (q, 2H, —$CH_2$N), 3.9 (s, 3H, $OCH_3$), 5.6 (br.s, 1H, —NH), 6.69, 6.75, 7.45 (m, 3H, ArH), 8.15 (s, 1H, CHO).

(g). 1-Bromo-4-(2-isocyano-ethyl)-2-methoxy-benzene

To the solution of the product of example 1f (5.0 g) in dry THF (35 ml) and was added triethylamine (13.5 ml). The solution was cooled to −10° C. A solution of $POCl_3$ (1.8 ml) in dry THF (6 ml) was added drop wise in 10 min. After stirring for 1 h at −10° C., ice water (100 ml) was added. The mixture was stirred at room temperature for 1.5 h. The reaction mixture was extracted twice with ethyl acetate. The organic layer was washed with brine, dried ($MgSO_4$), filtered and concentrated in vacuo. The residue was purified by chromatography on silica gel with heptane/ethyl acetate [2:1 (v/v)] as eluent.

Yield: 4.06 g. MS-ESI: $[M+H]^+$=240.1/242.1; TLC $R_f$=0.50 (heptane/ethyl acetate, 1/1); $^1$H-NMR ($CDCl_3$) δ 2.95 (t, 2H, —$CH_2$), 3.6 (t, 2H, —$CH_2$N), 3.9 (s, 3H, $OCH_3$), 6.7, 6.78, 7.5 (m, 3H, ArH).

(h). N-[2-(4-Bromo-3-methoxy-phenyl)-ethyl]-2-formylamino-2-thiophen-2-yl-acetamide A mixture of the product of example 1g (4.0 g), thiophene-2-carbaldehyde (1.8 g) and ammonium formate (2.22 g) in methanol (40 ml) was refluxed for 4 h. At room temperature, the mixture was concentrated to a small volume. Water (100 ml) and warm ethyl acetate (200 ml) were added. The product was extracted twice with warm ethyl acetate (100 ml). The organic layers were washed with water, brine, dried ($MgSO_4$), filtered and concentrated in vacuo. The crude product was crystallized from cold ethyl acetate and dried in vacuo (50° C.).

Yield: 3.43 g. MS-ESI: $[M+H]^+$=397.1/399.1; TLC $R_f$=0.66 (dichloromethane/acetone 1:1); Mp: 153-154° C.; $^1$H-NMR (DMSO-$d_6$) δ 2.7 (t, 2H, —$CH_2$), 3.32 (m, 2H, —$CH_2$N), 3.79 (s, 3H, $OCH_3$), 5.7-8.86 (m, 10H, ArH+NH+CHO).

(i). 9-Bromo-8-methoxy-1-thiophen-2-yl-5,6-dihydro-imidazo[5,1-a]isoquinoline $P_2O_5$ (10.0 g) was added with stirring to methanesulfonic acid (50 ml). The mixture was stirred at 75° C. until most of the $P_2O_5$ had dissolved (30 min). The product of example 1h (5.8 g) was added as a powder in one portion. The reaction mixture was stirred at 75° C. for 1.5 h. A dark green solution appeared. At room temperature, the reaction mixture was poured on to solid $NaHCO_3$ (150 g), diluted with water and extracted with ethyl acetate. The organic layer was washed with brine, dried ($MgSO_4$), filtered and concentrated in vacuo. The residue was purified by chromatography on silica gel with a gradient of toluene/acetone as eluent. The fractions containing product were collected, concentrated in vacuo and dissolved in hot ethanol (60 ml). Norit (350 mg) was added. After filtration, the filtrate was concentrated in vacuo and triturated with diethyl ether. The solid was collected and dried in vacuo (50° C.).

Yield: 3.9 g. Mp: 170-173° C.; $^1$H-NMR ($CDCl_3$) δ 3.05 (t, 2H, C(6)$H_2$), 3.9 (s, 3H, $OCH_3$), 4.1 (t, 2H, C(5)$H_2$), 6.8 (s, 1H, ArH7), 7.1, 7.35 (m, 3H, thiophene), 7.52 (s, 1H, ArH10), 8.05 (s, 1H, —NCHN—).

(j). 9-Bromo-8-methoxy-1-thiophen-2-yl-5,6-dihydro-imidazo[5,1-a]isoquinoline-3-carboxylic acid tert-butyl-methyl-amide A solution of diisopropylamine (0.67 g) in freshly distilled THF (5 ml) was cooled to −60° C. An n-BuLi solution (3.81 ml, 1.6 M in hexanes) was added drop wise. The mixture was stirred for 15 min at −60° C. A solution of the product of example 1i (1.0 g) in freshly distilled THF (10 ml) was added drop wise at −78° C. The mixture was allowed to warm to 0° C. After stirring at 0° C. for 30 min, the reaction mixture was cooled again to −60° C. and poured on $CO_2$ pellets. The mixture was stirred for additional 15 min and concentrated in vacuo. The remaining solid was dissolved in dry DMF (15 ml). N-methyl-tert-butylamine (0.48 g), N-ethylmorpholine (0.96 g), 1-hydroxybenzotriazole (0.22 g) and TBTU (1.33 g) were successively added. The reaction mixture was stirred at room temperature for 4 h. The mixture was poured to an aqueous NH$_4$Cl solution (5%) and extracted with ethyl acetate (80 ml). The combined organic layers were washed with water (100 ml), brine (100 ml), dried (Na$_2$SO$_4$), filtered and concentrated in vacuo. The residue was purified by chromatography on silica gel in heptane/ethyl acetate [1:1 (v/v)] as eluent. The fractions containing product were combined and concentrated in vacuo. The crude product was triturated with diisopropylether/heptane [1:1 (v/v)].

Yield: 0.9 g. UPLC/MS: [M+H]$^+$=474.3/476.3; Mp: 160-161° C.; TLC R$_f$=0.65 (toluene/ethyl acetate 1:1); $^1$H-NMR (CDCl$_3$) δ 1.5 (s, 9H, tert-butyl), 3.0 (t, 2H, C(6)H$_2$), 3.25 (s, 3H, NCH$_3$), 3.92 (s, 3H, OCH$_3$), 4.4 (t, 2H, C(5)H$_2$), 6.8 (s, 1H, ArH7), 7.1, 7.3, 7.35 (m, 3×1H, thiophene), 7.92 (s, 1H, ArH10); hFSHRago (CHO luc) EC$_{50}$=36 nM.

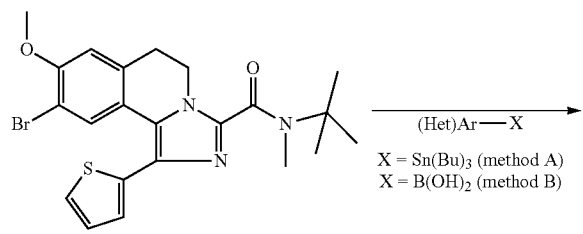

1j

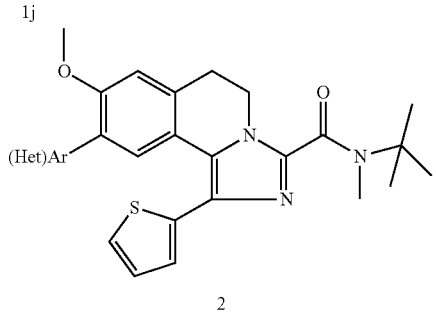

2

Example 2

8-Methoxy-9-pyridin-3-yl-1-thiophen-2-yl-5,6,6a,10a-tetrahydro-imidazo[5,1-a]isoquinoline-3-carboxylic acid tert-butyl-methyl-amide, 8-methoxy-9-pyridin-2-yl-1-thiophen-2-yl-5,6-dihydro-imidazo[5,1-a]isoquinoline-3-carboxylic acid tert-butyl-methyl-amide, 9-(6-fluoro-pyridin-2-yl)-8-methoxy-1-thiophen-2-yl-5,6-dihydro-imidazo[5,1-a]isoquinoline-3-carboxylic acid tert-butyl-methyl-amide, 8-methoxy-9-(6-morpholin-4-yl-pyridin-2-yl)-1-thiophen-2-yl-5,6-dihydro-imidazo[5,1-a]isoquinoline-3-carboxylic acid tert-butyl-methyl-amide, 8-ethoxy-1-thiophen-2-yl-9-(3-trifluoromethyl-phenyl)-5,6-dihydro-imidazo[5,1-a]isoquinoline-3-carboxylic acid tert-butyl-methyl-amide, 9-(3-acetylamino-phenyl)-8-methoxy-1-thiophen-2-yl-5,6-dihydro-imidazo[5,1-a]isoquinoline-3-carboxylic acid tert-butyl-methyl-amide, 8-methoxy-9-(3-pyrazol-1-yl-phenyl)-1-thiophen-2-yl-5,6-dihydro-imidazo[5,1-a]isoquinoline-3-carboxylic acid tert-butyl-methyl-amide, 8-methoxy-9-(3-morpholin-4-yl-phenyl)-1-thiophen-2-yl-5,6-dihydro-imidazo[5,1-a]isoquinoline-3-carboxylic acid tert-butyl-methyl-amide, 9-(3-fluoro-phenyl)-8-methoxy-1-thiophen-2-yl-5,6-dihydro-imidazo[5,1-a]isoquinoline-3-carboxylic acid tert-butyl-methyl-amide, 9-(2-cyano-phenyl)-8-methoxy-1-thiophen-2-yl-5,6-dihydro-imidazo[5,1-a]isoquinoline-3-carboxylic acid tert-butyl-methyl-amide, 9-(3-amino-phenyl)-8-methoxy-1-thiophen-2-yl-5,6-dihydro-imidazo[5,1-a]isoquinoline-3-carboxylic acid tert-butyl-methyl-amide, 9-(3-dimethylamino-phenyl)-8-methoxy-1-thiophen-2-yl-5,6-dihydro-imidazo[5,1-a]isoquinoline-3-carboxylic acid tert-butyl-methyl-amide, 9-(3,5-dimethyl-isoxazol-4-yl)-8-methoxy-1-thiophen-2-yl-5,6-dihydro-imidazo[5,1-a]isoquinoline-3-carboxylic acid tert-butyl-methyl-amide, 9-(3-dimethylcarbamoyl-phenyl)-8-methoxy-1-thiophen-2-yl-5,6-dihydro-imidazo[5,1-a]isoquinoline-3-carboxylic acid tert-butyl-methyl-amide, 4-{3-[3-(tert-butyl-methyl-carbamoyl)-8-methoxy-1-thiophen-2-yl-5,6-dihydro-imidazo[5,1-a]isoquinolin-9-yl]-phenyl}-piperazine-1-carboxylic acid tert-butyl ester, 9-(3-methanesulfonyl-phenyl)-8-methoxy-1-thiophen-2-yl-5,6-dihydro-imidazo[5,1-a]isoquinoline-3-carboxylic acid tert-butyl-methyl-amide, 8-methoxy-9-(2-methoxy-phenyl)-1-thiophen-2-yl-5,6-dihydro-imidazo[5,1-a]isoquinoline-3-carboxylic acid tert-butyl-methyl-amide and 9-benzo[1,3]dioxol-5-yl-8-methoxy-1-thiophen-2-yl-5,6-dihydro-imidazo[5,1-a]isoquinoline-3-carboxylic acid tert-butyl-methyl-amide (a). 8-Methoxy-9-pyridin-3-yl-1-thiophen-2-yl-5,6,6a,10a-tetrahydro-imidazo[5,1-a]isoquinoline-3-carboxylic acid tert-butyl-methyl-amide General Method A:

A mixture of the product of example 1j (0.5 g) and 3-(tributylstannyl)-pyridine (116 mg) were dissolved in dry degassed (N$_2$ sparging) toluene (2 ml). Pd(PPh$_3$)$_4$ (12.2 mg) was added and the reaction mixture was stirred under nitrogen atmosphere at 100° C. for 18 h. The reaction mixture was cooled to room temperature and diluted with ethyl acetate. The organic layer was washed with water, brine, dried (MgSO$_4$), filtered and concentrated in vacuo. The residue was purified by chromatography on silica gel (toluene/ethyl acetate as eluent). The fractions containing product were combined, concentrated in vacuo and crystallized from diethyl ether.

Yield: 30 mg. UPLC/MS: [M+H]$^+$=473.3; Mp: 241° C.; $^1$H-NMR (DMSO-d$_6$) δ 1.48 (s, 9H, tert-butyl), 3.08 (s, 3H, NCH$_3$), 3.15 (t, 2H, C(6)H$_2$), 3.84 (s, 3H, OCH$_3$), 4.23 (t, 2H, C(5)H$_2$), 7.1-8.5 (m, 9H, thiophene+pyridine); hFSHRago (CHO luc) EC$_{50}$=1 nM.

(b). 8-Methoxy-9-pyridin-2-yl-1-thiophen-2-yl-5,6-dihydro-imidazo[5,1-a]isoquinoline-3-carboxylic acid tert-butyl-methyl-amide (c). 9-(6-Fluoro-pyridin-2-yl)-8-methoxy-1-thiophen-2-yl-5,6-dihydro-imidazo[5,1-a]isoquinoline-3-carboxylic acid tert-butyl-methyl-amide (d). 8-Methoxy-9-(6-morpholin-4-yl-pyridin-2-yl)-1-thiophen-2-yl-5,6-dihydro-imidazo[5,1-a]isoquinoline-3-carboxylic acid tert-butyl-methyl-amide Example 2b-2d was prepared in a similar manner as described for example 2a starting from the product of example 1j.

| Example | | Method | Mp (° C.) | [M + H]+ | hFSHRago (CHO luc) EC$_{50}$ (nM) | NMR δ (ppm) |
|---|---|---|---|---|---|---|
| 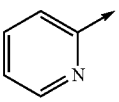 | 2b | A | 176-177 | 473.3 | 13 | 1.55(s, 3H, tert-butyl), 3.18(t, 2H, C(6)H$_2$), 3.26(s, 3H, NMe), 3.89(s, 3H, OCH$_3$), 4.43(t, 2H, C(5)H$_2$), 6.68-8.0 (m, 9H, Ar—H) |
| 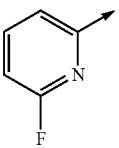 | 2c | A | 161-162 | 491.1 | 3 | 1.55(s, 3H, tert-butyl), 3.12(t, 2H, C(6)H$_2$), 3.26(s, 3H, NMe), 3.89(s, 3H, OCH$_3$), 4.43(t, 2H, C(5)H$_2$), 6.68-8.3 (m, 9H, Ar—H) |
| 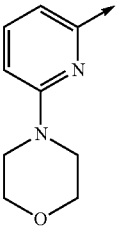 | 2d | A | | 558.3 | 100 | 1.48(s, 9H, tert-butyl),, 3.07(s, 3H, CH3N), 3.15(t, 2H, H6), 4.23(t, 2H, H5), 3.35(bm, 4H, morpholine CH2N), 3.69(m, 4H, morpholine CH2O), 3.90(s, 3H, OCH$_3$), 7.08, 7.38, 7.59(3 × m, 3H, thiophene), 6.82(s, 1H, pyrH5), 7.25(m, 1H, H7), 7.28 s, 1H, pyrH3), 7.63(s, 1H, pyrH4), 8.25(s, 1H, H10) |

(e). 8-Methoxy-1-thiophen-2-yl-9-(3-trifluoromethyl-phenyl)-5,6-dihydro-imidazo[5,1-a]isoquinoline-3-carboxylic acid tert-butyl-methyl-amide General Method B:

A mixture of the product of example 1j (50 mg), 3-(trifluoromethyl)phenylboronic acid (40 mg) and K$_2$CO$_3$ (44 mg) in 4 ml of degassed (N2-sparging) aqueous DME solution (10%). Pd(PPh$_3$)$_4$ (12.2 mg) was added. The reaction mixture was stirred under N$_2$ at 90° C. for 4.5 h. At room temperature, the reaction mixture was diluted with ethyl acetate. The organic layer was washed with an aqueous NaOH solution (1 M), water, brine, dried (MgSO$_4$), filtered and concentrated in vacuo. The residue was purified by preparative HPLC (20→100% acetonitrile; with 2% TFA). The fractions containing product were combined and extracted with dichloromethane (2×50 ml). The organic layer was washed with a saturated NaHCO$_3$ solution, water, and brine, dried (MgSO$_4$), filtered and concentrated in vacuo. The remaining product was crystallized from diisopropylether.

Yield: 27.5 mg. UPLC/MS: [M+H]+=540.3. Mp: 185-186° C.; $^1$H-NMR (DMSO-d$_6$) δ 1.48 (s, 9H, tert-butyl), 3.09 (s, 3H, NCH$_3$), 3.25 (t, 2H, C(6)H$_2$), 3.85 (s, 3H, OCH$_3$), 4.23 (t, 2H, C(5)H$_2$), 7.09, 7.41, 7.55 (m, 3×1H, thiophene), 7.25-7.7 (m, 6×1H, ArH); hFSHRago (CHO luc) EC$_{50}$=65 nM.

(f). 9-(3-Acetylamino-phenyl)-8-methoxy-1-thiophen-2-yl-5,6-dihydro-imidazo[5,1-a]isoquinoline-3-carboxylic acid tert-butyl-methyl-amide (g). 8-Methoxy-9-(3-pyrazol-1-yl-phenyl)-1-thiophen-2-yl-5,6-dihydro-imidazo[5,1-a]isoquinoline-3-carboxylic acid tert-butyl-methyl-amide (h). 8-Methoxy-9-(3-morpholin-4-yl-phenyl)-1-thiophen-2-yl-5,6-dihydro-imidazo[5,1-a]isoquinoline-3-carboxylic acid tert-butyl-methyl-amide (i). 9-(3-Fluoro-phenyl)-8-methoxy-1-thiophen-2-yl-5,6-dihydro-imidazo[5,1-a]isoquinoline-3-carboxylic acid tert-butyl-methyl-amide (j). 9-(2-Cyano-phenyl)-8-methoxy-1-thiophen-2-yl-5,6-dihydro-imidazo[5,1-a]isoquinoline-3-carboxylic acid tert-butyl-methyl-amide (k). 9-(3-Amino-phenyl)-8-methoxy-1-thiophen-2-yl-5,6-dihydro-imidazo[5,1-a]isoquinoline-3-carboxylic acid tert-butyl-methyl-amide (l). 9-(3-Dimethylamino-phenyl)-8-methoxy-1-thiophen-2-yl-5,6-dihydro-imidazo[5,1-a]isoquinoline-3-carboxylic acid tert-butyl-methyl-amide (m). 9-(3,5-Dimethyl-isoxazol-4-yl)-8-methoxy-1-thiophen-2-yl-5,6-dihydro-imidazo[5,1-a]isoquinoline-3-carboxylic acid tert-butyl-methyl-amide (n). 9-(3-Dimethylcarbamoyl-phenyl)-8-methoxy-1-thiophen-2-yl-5,6-dihydro-imidazo[5,1-a]iso-quinoline-3-carboxylic acid tert-butyl-methyl-amide (o). 4-{3-[3-(tert-Butyl-methyl-carbamoyl)-8-methoxy-1-thiophen-2-yl-5,6-dihydro-imidazo[5,1-a]isoquinolin-9-yl]-phenyl}-piperazine-1-carboxylic acid tert-butyl ester (p). 9-(3-Methanesulfonyl-phenyl)-8-methoxy-1-thiophen-2-yl-5,6-dihydro-imidazo[5,1-a]isoquinoline-3-carboxylic acid tert-butyl-methyl-amide (q). 8-Methoxy-9-(2-methoxy-phenyl)-1-thiophen-2-yl-5,6-dihydro-imidazo[5,1-a]isoquinoline-3-carboxylic acid tert-butyl-methyl-amide (r). 9-Benzo[1,3]dioxol-5-yl-8-methoxy-1-thiophen-2-yl-5,6-dihydro-imidazo[5,1-a]isoquinoline-3-carboxylic acid tert-butyl-methyl-amide

| Example | | Method | Mp (° C.) | [M + H]+ | hFSHRago (CHO luc) EC$_{50}$ (nM) | NMR δ (ppm) |
|---|---|---|---|---|---|---|
| 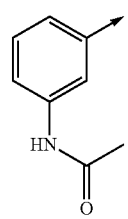 | 2f | B | 123 | 529.2 | 1 | 1.55(s, 3H, tert-butyl), 2.2(s, 3H, Me), 3.1(t, 2H, C(6)H$_2$), 3.26(s, 3H, NCH$_3$), 3.85(s, 3H, OCH$_3$), 4.43(t, 2H, C(5)H$_2$), 6.68-7.7(m, 9H, Ar—H) |

-continued

| Example | | Method | Mp (° C.) | [M + H]+ | hFSHRago (CHO luc) EC50 (nM) | NMR δ (ppm) |
|---|---|---|---|---|---|---|
| 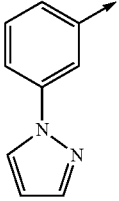 | 2g | B | 180 | 538.2 | 2 | 1.52(s, 9H, tert-butyl), 3.12(t, 2H, C(6)H2), 3.28 (s, 3H, NCH3), 3.87(s, 3H, OCH3), 4.45(t, 2H, C(5)H2), 6.5-7.9(m, 12H, Ar—H) |
| 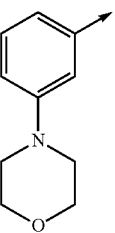 | 2h | B | 85-90 | 557.2 | 2 | 1.55(s, 9H, tert-butyl), 3.15(m, 3 × 2H, C(6)H2, NCH2), 3.25(s, 3H, NCH3), 3.82(s, 3H, OCH3), 3.9(m, 2 × 2H, NCH2), 4.43(t, 2H, C(5)H2), 6.85-7.72(m, 9H, Ar—H) |
| 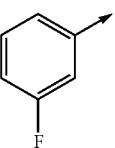 | 2i | B | 165 | 490.5 | 3 | 1.55(s, 9H, tert-butyl), 3.14(t, 2H, C(6)H2), 3.28 (s, 3H, NCH3), 3.85(s, 3H, OCH3), 4.45(t, 2H, C(5)H2), 6.9-7.7(m, 9H, Ar—H) |
| 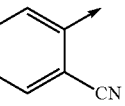 | 2j | B | — | 497.2 | 5 | 1.55(s, 9H, tert-butyl), 3.15(t, 2H, C(5)H2), 3.25 (s, 3H, NCH3), 3.87(s, 3H, OCH3), 4.45(br.s. 2H, C(6)H2), 6.92-7.7 (m, 9H, Ar—H) |
| 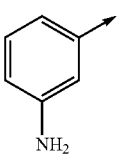 | 2k | B | 213 | 487.2 | 8 | 1.52(s, 9H, tert-butyl), 3.1(t, 2H, C(6)H2), 3.25 (s, 3H, NCH3), 3.64 (br.s, 2H, NH2), 3.83(s, 3H, OCH3), 4.43(t, 2H, C(5)H2), 6.62-7.7(m, 9H, Ar—H) |
| 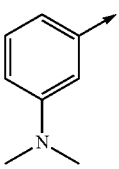 | 2l | B | 149 | 515.2 | 9 | 1.52(s, 3H, tert-butyl), 2.0, 2.2(s, 2 × 3H, Me), 3.05(s, 6H, NCH3), 3.08 (t, 2H, C(6)H2), 3.83(s, 3H, OCH3), 4.23(t, 2H, C(5)H2), 7.1-7.6(m, 9H, Ar—H) |
| 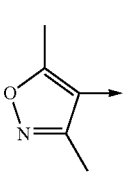 | 2m | B | 183-184 | 491.3 | 9 | 1.52(s, 3H, tert-butyl), 2.95(s, 6H, NCH3), 3.1 (t, 2H, C(6)H2), 3.25(s, 3H, NCH3), 3.83(s, 3H, OCH3), 4.43(t, 2H, C(5)H2), 6.7-7.77(m, 9H, Ar—H) |
| 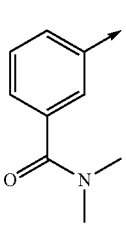 | 2n | B | 151 | 543.4 | 11 | 1.55(s, 9H, tert-butyl), 2.96(br.s, 3H, NCH3), 3.14(m, 5H, NCH3, C(6)H2), 3.25(s, 3H, NCH3), 3.84(s, 3H, OCH3), 4.45(t, 2H, C(5)H2), 6.9-7.7(m, 9H, Ar—H) |

-continued

| Example | | Method | Mp (° C.) | [M + H]+ | hFSHRago (CHO luc) EC50 (nM) | NMR δ (ppm) |
|---|---|---|---|---|---|---|
| 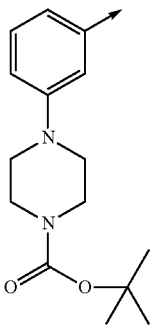 | 2o | B | — | 656.4 | 14 | 1.5(d, 18H, tert-butyl), 3.1(t, 3 × 2H, C(6)H2, NCH2), 3.25(s, 3H, NCH3), 3.6(t, 2 × 2H, NCH2), 3.83(s, 3H, OCH3), 4.43(t, 2H, C(5)H2), 6.85-7.7(m, 9H, Ar—H) |
| 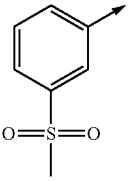 | 2p | B | 216 | 550.4 | 15 | 1.52(s, 9H, tert-butyl), 3.05(s, 3H, NCH3), 3.15 (t, 2H, C(6)H2), 3.28(s, 3H, —SO2CH3), 3.86(s, 3H, OCH3), 4.45(t, 2H, C(5)H2), 6.9-8.0(m, 9H, Ar—H) |
| 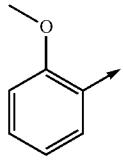 | 2q | B | 188-189 | 502.3 | 50 | 1.48(s, 9H, tert-butyl), 3.05(s, 3H, NCH3), 3.1 (t, 2H, C(6)H2), 3.75(d, 2 × 3H, 2 × OCH3), 4.2(t, 2H, C(5)H2), 6.9-7.55 (m, 9H, Ar—H) |
| 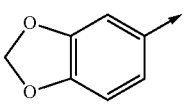 | 2r | B | 162 | 516.3 | 167 | 1.48(s, 9H, tert-butyl), 3.05(s, 3H, NCH3), 3.1 (t, 2H, C(6)H2), 3.8(s, 3H, OCH3), 4.2(t, 2H, C(5)H2), 6.02(s, 2H, —OCH2), 6.8-7.6(m, 8H, Ar—H) |

Method A = Stille reaction;
Method B = Suzuki reaction

Example 2f-2r were prepared in a similar manner as described for example 2e starting from the product of example 1j.

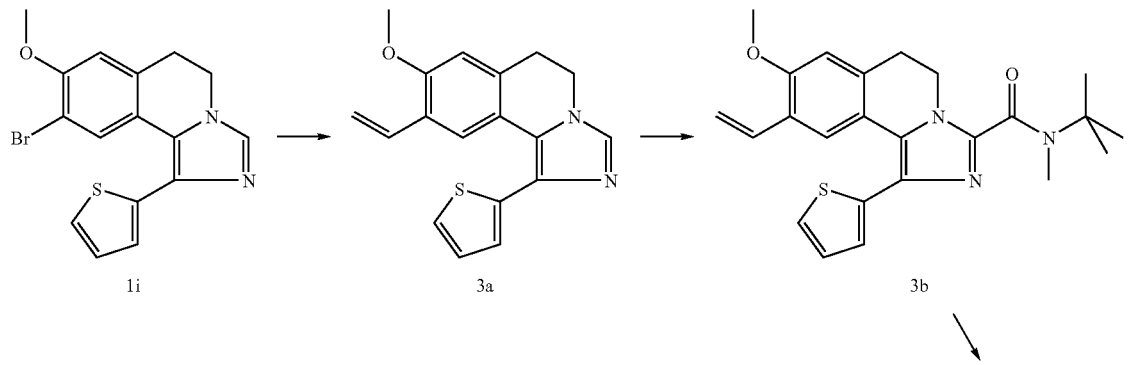

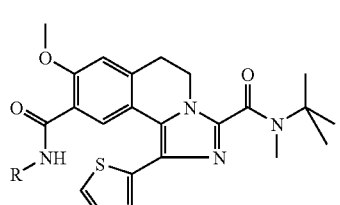 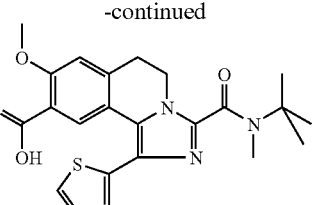 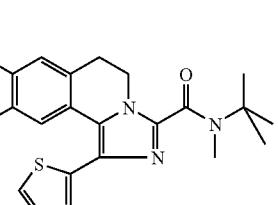

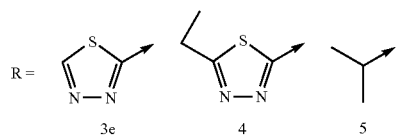

Example 3

8-Methoxy-1-thiophen-2-yl-5,6-dihydro-imidazo[5,1-a]isoquinoline-3,9-dicarboxylic acid 3-(tert-butyl-methyl-amide) 9-[1,3,4]thiadiazol-2-ylamide

(a). 8-Methoxy-1-thiophen-2-yl-9-vinyl-5,6-dihydro-imidazo[5,1-a]isoquinoline A mixture of the product of example 1i (2.7 g), 2,4,6-trivinyl-cycloriboroxane pyridine (3 g), $K_2CO_3$ (3 g) and $Pd(PPh_3)_4$ (150 mg) in an aqueous DME degassed solution (80 ml 90%) was stirred under $N_2$ at 90° C. for 24 h. At room temperature, the reaction mixture was poured in an aqueous $NH_4Cl$ solution (5%) and extracted with ethyl acetate. The organic layer was dried ($MgSO_4$), filtered and concentrated in vacuo. The residue was purified by chromatography on silica gel in toluene/dioxane [1:1 (v/v)] as eluent. The fractions with product were combined and concentrated in vacuo. The residue was triturated with diethyl ether to give off-white crystalline product.

Yield: 650 mg. LC/MS-ESI: [M+H]$^+$=309.1; Mp: 195° C.; $R_f$=0.20 (toluene/ethyl acetate 1:1); $^1$H-NMR (DMSO-d$_6$) δ 3.05 (t, 2H, C(6)H$_2$), 3.84 (s, 3H, OCH$_3$), 4.15 (t, 2H, C(5)H$_2$), 5.18, 5.4 (dd, 2H, =CH$_2$), 6.9 (m, 1H, =CH), 7.05 (s, 1H, ArH7), 7.12, 7.3, 7.52 (m, 3H, thiophene), 7.78 (s, 1H, ArH10), 7.85 (s, 1H, —NCHN—).

(b). 8-Methoxy-1-thiophen-2-yl-9-vinyl-5,6-dihydro-imidazo[5,1-a]isoquinoline-3-carboxylic acid tert-butyl-methyl-amide To a suspension of the product of example 3a (650 mg) in dry THF (10 ml) was added at −40° C. n-BuLi (1.4 ml; 1.6 M in heptane). After stirring for 10 min at −40° C., the reaction mixture was poured on $CO_2$ pellets, stirred for 15 min and concentrated in vacuo at 35° C. To a solution of the residue in DMF (7 ml) and N-ethylmorpholine (300 μl) were added N-methyl-tert-butylamine (300 μl) and TBTU (800 mg). After stirring at room temperature for 2 h, the reaction mixture was poured into an aqueous $NH_4Cl$ solution (5%) and extracted with ethyl acetate. The organic layer was dried ($MgSO_4$), filtered and concentrated in vacuo. The residue was purified by chromatography on silica gel in toluene/ethyl acetate [1:1 (v/v)] as eluent. The fractions with product combined and concentrated in vacuo. The residue was triturated with diethyl ether and the solid was dried in vacuo (50° C.).

Yield: 290 mg. LC/MS-ESI: [M+H]$^+$=422.1; $R_f$=0.73 (toluene/ethyl acetate 1:1); Mp: 154-155° C.; $^1$H-NMR (DMSO-d$_6$) δ 1.48 (s, 9H, tert-butyl), 3.05 (t, 2H, C(6)H$_2$), 3.33 (s, 3H, NCH$_3$), 3.85 (s, 3H, OCH$_3$), 4.2 (t, 2H, C(5)H$_2$), 5.2, 5.4 (dd, 2H, =CH$_2$), 6.9 (m, 1H, =CH), 7.08 (s, 1H, ArH7), 7.15, 7.32, 7.6 (m, 3H, thiophene), 7.81 (s, 1H, ArH10); hFSHRago (CHO luc) EC$_{50}$=28 nM.

(c). 9-Formyl-8-methoxy-1-thiophen-2-yl-5,6-dihydro-imidazo[5,1-a]isoquinoline-3-carboxylic acid tert-butyl-methyl-amide An aqueous solution of osmium tetroxide (300 μl 14%) was added to a solution of the product of example 3b (270 mg) in THF (10 ml), followed by the addition of a solution of sodium periodate (600 mg) in water (2 ml). After stirring at 55° C. for 30 min, the reaction was poured in water, treated with a sat. aqueous $Na_2S_2O_3$ solution and extracted with ethyl acetate. The organic layer was washed with brine, dried ($MgSO_4$), filtered and concentrated in vacuo. The residue was purified by chromatography on silica gel (toluene/ethyl acetate) as eluent.

Yield: 160 mg. LC/MS-ESI: [M+H]$^+$=424.1; $R_f$=0.5 (toluene/ethyl acetate 1:1); Mp: 108-110° C.; $^1$H-NMR (DMSO-d$_6$): δ 1.48 (s, 9H, tert-butyl), 3.17 (t, 2H, C(6)H$_2$), 3.33 (s, 3H, NCH$_3$), 3.97 (s, 3H, OCH$_3$), 4.2 (t, 2H, C(5)H$_2$), 7.12, 7.3, 7.59 (m, 3H, thiophene), 7.34 (s, 1H, ArH7), 8.12 (s, 1H, ArH10), 10.28 (s, 1H, —CHO).

(d). 3-(tert-butyl-methyl-carbamoyl)-8-methoxy-1-thiophen-2-yl-5,6-dihydro-imidazo[5,1-a]isoquinoline-9-carboxylic acid A mixture of the product of example 3c (150 mg), 2-methyl-but-2-ene (0.5 ml) and $NaH_2PO_4$ (270 mg) in water (5 ml) and t-butanol (12 ml) was treated with an aqueous $NaClO_2$ solution (270 mg in 3 ml water). The reaction mixture was stirred at room temperature for 1.5 h, concentrated in vacuo to a small volume and diluted with water (15 ml). The aqueous layer was adjusted to pH=5 with an aqueous HCl solution (1N) and extracted with ethyl acetate. The organic layer was dried ($MgSO_4$), filtered and concentrated in vacuo. The residue was purified by chromatography on silica gel [toluene/acetone (v/v)] as eluent.

Yield: 130 mg. LC/MS-ESI: [M+H]$^+$=440.1; TLC $R_f$=0.20 (toluene/acetone 1:1); Mp: 125-128° C.; $^1$H-NMR (DMSO-d$_6$): δ 1.48 (s, 9H, tert-butyl), 3.10 (t, 2H, C(6)H$_2$), 3.33 (s, 3H, NCH$_3$), 3.86 (s, 3H, OCH$_3$), 4.2 (t, 2H, C(5)H$_2$), 7.10, 7.3, 7.55 (m, 3H, thiophene), 7.2 (s, 1H, ArH7), 8.12 (s, 1H, ArH10), 12.55 (br.s., 1H, COOH).

(e). 8-Methoxy-1-thiophen-2-yl-5,6-dihydro-imidazo[5,1-a]isoquinoline-3,9-dicarboxylic acid 3-(tert-butyl-methyl-amide) 9-[1,3,4]thiadiazol-2-ylamide A mixture of the product of example 3d (40 mg), [1,3,4]thiadiazol-2-ylamine (20 mg), TBTU (40 mg) and N-ethylmorpholine (20 μl) in DMF (0.6 ml) was stirred at room temperature for 5 h. The reaction mixture was diluted with water and extracted with ethyl acetate. The organic layer was washed with brine, dried (MgSO$_4$), filtered and concentrated in vacuo. The residue was purified by chromatography on silica gel in toluene/acetone [1:1 (v/v)] as eluent. The fractions with product were combined, concentrated in vacuo. The isolated product was treated with diethyl ether. The solids were collected and dried in vacuo (50° C.).

Yield: 22 mg. LC/MS-ESI: [M+H]$^+$=523.1; TLC R$_f$=0.40 (toluene/acetone 1:1); Mp: 154-156° C.; $^1$H-NMR (DMSO-d$_6$) δ 1.48 (s, 9H, tert-butyl), 3.08 (s, 3H, NCH$_3$), 3.18 (t, 2H, C(6)H$_2$), 4.0 (s, 3H, OCH$_3$), 4.22 (t, 2H, C(5)H$_2$), 7.12, 7.35, 7.55 (m, 3×1H, thiophene), 7.31 (s, 1H, H7-Ar), 8.15 (s, 1H, H10-Ar), 9.2 (s, 1H, thiadiaz.-H), δ 12.2 (br s, 1H, NH); hFSHRago (CHO luc) EC$_{50}$=3 nM.

Example 4

8-Methoxy-1-thiophen-2-yl-5,6-dihydro-imidazo[5,1-a]isoquinoline-3,9-dicarboxylic acid 3-(tert-butyl-methyl-amide) 9-[(5-ethyl-[1,3,4]thiadiazol-2-yl)-amide]

Coupling of the product of example 3d (40 mg) with 5-ethyl-2-aminothiadiazole (20 mg) was performed according to the method described for example 3e.

Yield: 24 mg. LC/MS-ESI: [M+H]$^+$=551.1; TLC R$_f$=0.40 (toluene/acetone 1:1); Mp: 238-240° C.; $^1$H-NMR (DMSO-d$_6$) δ 1.3 (m, 3H, CH$_3$) 1.48 (s, 9H, tert-butyl), 3.0 (q, 2H, CH$_2$), 3.08 (s, 3H, NCH$_3$), 3.18 (t, 2H, C(6)H$_2$), 3.9 (s, 3H, OCH$_3$), 4.22 (t, 2H, C(5)H$_2$), 7.12, 7.35, 7.55 (m, 3×1H, thiophene), 7.31 (s, 1H, H7-Ar), 8.14 (s, 1H, H10-Ar), 12.2 (br s, 1H, NH); hFSHRago (CHO luc) EC$_{50}$=58 nM.

Example 5

8-Methoxy-1-thiophen-2-yl-5,6-dihydro-imidazo[5,1-a]isoquinoline-3,9-dicarboxylic acid 3-(tert-butyl-methyl-amide) 9-isopropylamide Coupling of the product of example 3d (40 mg) with isopropylamine (20 μl) was performed according to the method described for example 3e.

Yield: 25 mg. LC/MS-ESI: [M+H]$^+$=481.2; TLC R$_f$=0.64 (toluene/acetone 1:1); Mp: 197-198° C.; $^1$H-NMR (DMSO-d$_6$) δ 1.13 (d, 6H, CH$_2$), 1.48 (s, 9H, tert-butyl), 3.08 (s, 3H, NCH$_3$), 3.18 (t, 2H, C(6)H$_2$), 3.92 (s, 3H, OCH$_3$), 4.0 (m, 1H, CH), 4.19 (t, 2H, C(5)H$_2$), 7.1, 7.34, 7.5 (m, 3×1H, thiophene), 7.2 (s, 1H, H7-Ar), 8.21 (s, 1H, H10-Ar), 7.88 (d, 1H, NH); hFSHRago (CHO luc) EC$_{50}$=18 nM.

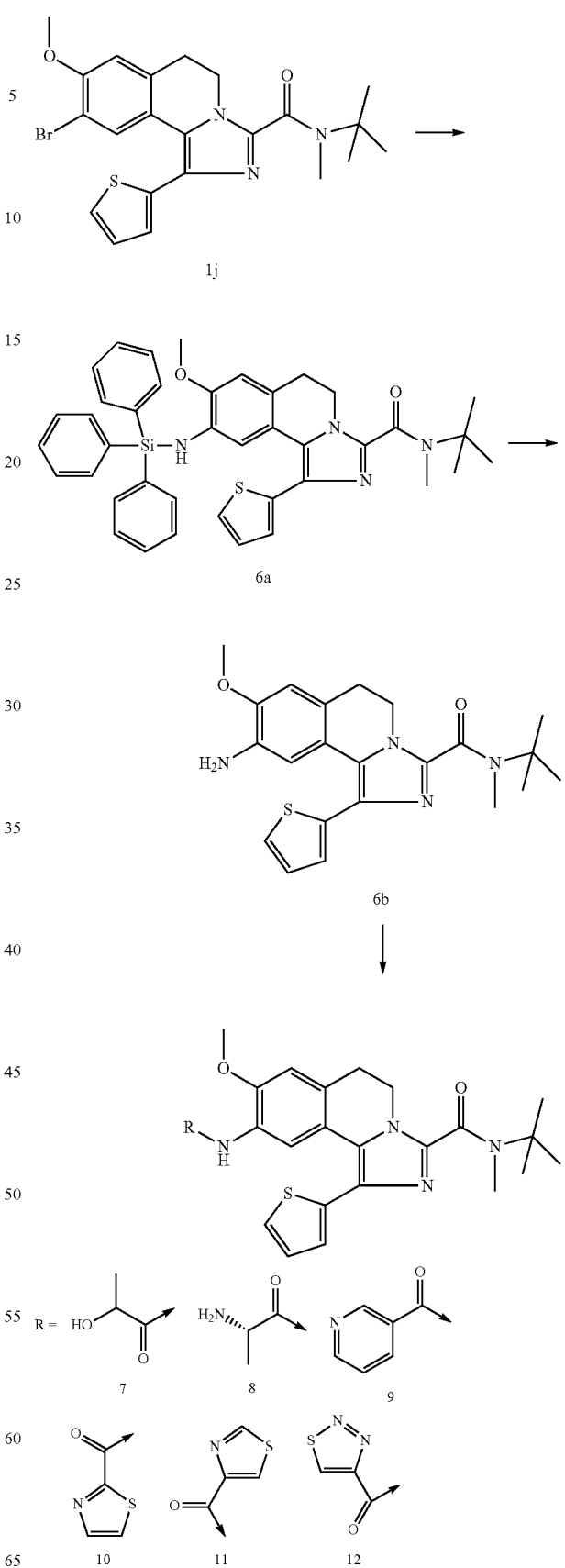

Example 6

9-Amino-8-methoxy-1-thiophen-2-yl-5,6-dihydro-imidazo[5,1-a]isoquinoline-3-carboxylic acid tert-butyl-methyl-amide; hydrochloric acid salt (a). 8-Methoxy-1-thiophen-2-yl-9-(triphenylsilanyl-amino)-5,6-dihydro-imidazo[5,1-a]isoquinoline-3-carboxylic acid tert-butyl-methyl-amide A degassed solution of the product of example 1j (560 mg), triphenylsilylamine (370 mg), Pd$_2$(dba)$_3$ (26 mg), 2-(dicyclohexylphosphino)biphenyl (26 mg) and a LiHMDS solution (1.2 ml 1M solution in THF)) in dry toluene (10 ml) was stirred under nitrogen atmosphere at 100° C. for 2 h. At room temperature, the mixture was diluted with a saturated aqueous NH$_4$Cl solution and extracted with ethyl acetate. The organic layer was washed with brine, dried (MgSO$_4$), filtered and concentrated in vacuo. The residue was purified by chromatography on silica gel in heptane/ethyl acetate [1:1 (v/V)] as eluent. The fractions with product were combined and concentrated in vacuo. The remaining residue was treated with ether/diisopropylether and the solids were collected and dried in vacuo (50° C.).

Yield: 420 mg. TLC R$_f$=0.40 (heptane/ethyl acetate 1:1); Mp: 210° C.; $^1$H-NMR (DMSO-d$_6$) δ 1.41 (s, 9H, tert-butyl), 2.9 (t, 2H, C(6)H$_2$), 2.85 (s, 3H, NCH$_3$), 3.88 (s, 3H, OCH$_3$), 4.0 (t, 2H, C(5)H$_2$), 4.84 (s, 1H, NH), 5.9, 6.59, 7.17 (m, 3H, thiophene), 6.96, 7.01 (s, 2H, ArH7+ArH10), 7.35-7.5 (m, 15H, ArH).

(b). 9-Amino-8-methoxy-1-thiophen-2-yl-5,6-dihydro-imidazo[5,1-a]isoquinoline-3-carboxylic acid tert-butyl-methyl-amide; hydrochloric acid salt To the product of example 6a (130 mg) was added a solution of HCl in dioxane (900 μl 0.4 M) and methanol (900 μl). After stirring at room temperature for 10 min, diethyl ether (5 ml) was added. The remaining solids were collected and dried in vacuo (50° C.).

Yield: 87 mg. TLC R$_f$=0.30 (heptane/ethyl acetate 1:1); Mp: 182-184° C.; $^1$H-NMR (DMSO-d$_6$) δ 1.47 (s, 9H, tert-butyl), 3.1 (t, 2H, C(6)H$_2$), 3.05 (s, 3H, NCH$_3$), 3.92 (s, 3H, OCH$_3$), 4.19 (t, 2H, C(5)H$_2$), 7.1, 7.34, 7.6 (3×m, 3H, thiophene), 7.28 (s, 1H, ArH7), 7.76 (s, 1H, ArH10); hFSHRago (CHO luc) EC$_{50}$=740 nM.

Example 7

9-(2-Hydroxy-propionylamino)-8-methoxy-1-thiophen-2-yl-5,6-dihydro-imidazo[5,1-a]isoquinoline-3-carboxylic acid tert-butyl-methyl-amide A mixture of the product of example 6b (21.9 mg), DIPEA (85 μl), TBTU (78.0 mg) and 2-hydroxy-propionic acid (18 μl) in dichloromethane (4 ml) was stirred at room temperature for 2 h. The reaction mixture was diluted with dichloromethane. The organic layer was washed with water, brine, dried (MgSO$_4$), filtered and concentrated in vacuo. The residue was purified by preparative HPLC (10→90% acetonitrile) and freeze dried from acetonitrile/water.

Yield: 14 mg. LC/MS-ESI: [M+H]$^+$=483.2; $^1$H-NMR (CDCl$_3$) δ 1.45 (d, 3H, CH$_3$), 1.53 (s, 9H, tert-butyl), 3.0 (t, 2H, C(6)H$_2$), 3.22 (s, 3H, NCH$_3$), 3.55 (br.s, 1H, OH), 3.85 (s, 3H, OCH$_3$), 4.3 (m, 3H, C(5)H$_2$ and CH(OH)), 6.7 (s, 1H, H7-Ar), 8.7 (s, 1H, H10-Ar), 7.1, 7.32, 7.43 (3×m, 3H, thiophene); hFSHRago (CHO luc) EC$_{50}$=35 nM.

Example 8

9-((S)-2-Amino-propionylamino)-8-methoxy-1-thiophen-2-yl-5,6-dihydro-imidazo[5,1-a]isoquinoline-3-carboxylic acid tert-butyl-methyl-amide A mixture of the product of example 6b (50 mg), DIPEA (100 μl), TBTU (120 mg) and (S)-2-(9H-fluoren-9-yl-methoxycarbonylamino)-propionic acid (150 mg) in dichloromethane (4 ml) was stirred at room temperature for 4 h. The reaction mixture was diluted with dichloromethane. The organic layer was washed with water, brine, dried (MgSO$_4$), filtered and concentrated in vacuo. To a solution of the residue in DMF (3 ml) was added piperidine (120 μl). The mixture was stirred at room temperature for 10 min and concentrated in vacuo. The residue was purified by preparative HPLC (10→90% acetonitrile).

Yield: 8 mg. LC/MS-ESI: [M+H]$^+$=482.2; $^1$H-NMR (CDCl$_3$) δ 1.39 (d, 3H, CH$_3$), 1.53 (s, 9H, tert-butyl), 3.03 (t, 2H, C(6)H$_2$), 3.22 (s, 3H, NCH$_3$), 3.6 (q, 1H, CHNH2), 3.91 (s, 3H, OCH$_3$), 4.32, 4.42 (2×m, 2H, C(5)H$_2$), 6.78, 8.82 (s, 2×1H, Ar—H), 7.14, 7.32, 7.5 (3×m, 3H, thiophene), 9.68 (s, 1H, NH); hFSHRago (CHO luc) EC$_{50}$=49 nM.

Example 9

8-Methoxy-9-[(pyridine-3-carbonyl)-amino]-1-thiophen-2-yl-5,6-dihydro-imidazo[5,1-a]isoquinoline-3-carboxylic acid tert-butyl-methyl-amide A mixture of the product of example 6b (35 mg), TBTU (50 mg) and nicotinic acid (35 mg) in pyridine (2 ml) was stirred at room temperature for 1 h. The reaction mixture was poured into water and extracted with ethyl acetate. The organic layer was washed with brine, dried (MgSO$_4$), filtered and concentrated in vacuo. The residue was purified by chromatography on silica gel in toluene/acetone [0→40% (v/v)] as eluent. The fractions with product combined and concentrated in vacuo. The residue was crystallized from acetonitrile and dried in vacuo (50° C.).

Yield: 29 mg. LC/MS-ESI: [M+H]$^+$=516.3; Mp: 159-161° C.; $^1$H-NMR (CDCl$_3$) δ 1.52 (s, 9H, tert-butyl), 3.05 (t, 2H, C(6)H$_2$), 3.26 (s, 3H, NCH$_3$), 3.96 (s, 3H, OCH$_3$), 4.42 (t, 2H, C(5)H$_2$), 6.83 (s, 1H, H7-Ar), 8.9 (s, 1H, H10-Ar), 7.18, 7.37, 7.52 (3×m, 3H, thiophene), 7.43, 8.19, 8.75, 9.05 (4×m, 4H, pyridine), 8.35 (br.s, 1H, NH); hFSHRago (CHO luc) EC$_{50}$=224 nM.

Example 10

8-Methoxy-9-[(thiazole-2-carbonyl)-amino]-1-thiophen-2-yl-5,6-dihydro-imidazo[5,1-a]isoquinoline-3-carboxylic acid tert-butyl-methyl-amide To a cooled solution of thiazole (30 μl) in dry THF (1 ml) at −60° C. was added an n-BuLi solution (1.6 M in hexane; 100 μl). After stirring for 10 min at −60° C., the mixture was quenched by addition of a CO$_2$ pellets and subsequently concentrated in vacuo at 35° C. To a solution of the residue in DMF (1 ml) and TBTU (50 mg), were added N-ethylmorpholine (40 μl) and the product of example 6b (60 mg). After stirring for 2 h, water was added and the mixture was extracted with ethyl acetate. The organic layer was washed with water, brine, dried (MgSO$_4$), filtered and concentrated in vacuo. The residue was purified by chromatography on silica gel in dichloromethane/ethyl acetate [1:1 (v/v)] as eluent, followed by trituration with diethyl ether.

Yield: 65 mg. LC/MS-ESI: [M+H]$^+$=522.1; Mp: 185-186° C.; TLC R$_f$=0.15 (heptane/ethyl acetate 1:1); $^1$H-NMR (CDCl$_3$) δ 1.5 (s, 3H, tert-butyl), 3.03 (t, 2H, C(6)H$_2$), 3.32 (s, 3H, NCH$_3$), 3.97 (s, 3H, OCH$_3$), 4.18 (t, 2H, C(5)H$_2$), 7.1, 7.45 and 7.51 (3×m, 3H, thiophene), 7.23 (s, 1H, ArH7), 8.1, 8.17 (2×dd, 2H, thiazole), 8.7 (s, 1H, ArH10), 9.71 (s, 1H, NH); hFSHRago (CHO luc) EC$_{50}$=12 nM.

Example 11

8-Methoxy-9-[(thiazole-4-carbonyl)-amino]-1-thiophen-2-yl-5,6-dihydro-imidazo[5,1-a]isoquinoline-3-carboxylic acid tert-butyl-methyl-amide A mixture of the product of example 6b (60 mg), thiazole-4-carboxylic acid (25 mg), N-ethylmorpholine (40 μl) and TBTU (50 mg) in DMF (1 ml) was stirred at room temperature for 2 h. The reaction mixture was poured in an aqueous NaHCO$_3$ solution (5%). The mixture was extracted with ethyl acetate. The organic layers were washed with brine, dried (MgSO$_4$), filtered and concentrated in vacuo. The residue was purified by chromatography on silica gel in dichloromethane/ethyl acetate as eluent. The fractions with product were combined and concentrated in vacuo. The residue was treated with diethyl ether and dried in vacuo (50° C.).

Yield: 45 mg. LC/MS-ESI: [M+H]$^+$=522.1; TLC R$_f$=0.16 (heptane/ethyl acetate 1:1); Mp: 240-242° C.; $^1$H-NMR (DMSO-d$_6$) δ 1.48 (s, 9H, tert-butyl), 3.05 (m, 3H+2H, NCH$_3$+C(6)H$_2$), 3.97 (s, 3H, OCH$_3$), 4.18 (t, 2H, C(5)H$_2$), 7.1, 7.48 and 7.51 (3×m, 3H, thiophene), 7.21 (s, 1H, H7-Ar), 8.90 (s, 1H, H10-Ar), 8.52, 9.25 (2×d, H2 and H5-thiaz), 9.78 (s, 1H, NH); hFSHRago (CHO luc) EC$_{50}$=13 nM.

Example 12

8-Methoxy-9[([1,2,3]thiadiazole-4-carbonyl)-amino]-1-thiophen-2-yl-5,6-dihydro-imidazo[5,1-a]isoquinoline-3-carboxylic acid tert-butyl-methyl-amide Coupling of the product of example 6b (80 mg) with [1,2,3]thiadiazole-4-carboxylic acid (30 mg) was performed according to the method described for example 11.

Yield: 55 mg. LC/MS-ESI: [M+H]$^+$=523.0; Mp: 210-212° C.; TLC R$_f$=0.18 (heptane/ethyl acetate 1:1); $^1$H-NMR (DMSO-d$_6$) δ 1.5 (s, 9H, tert-butyl), 3.08 (t, 2H, C(6)H$_2$), 3.32 (s, 3H, NCH$_3$), 3.98 (s, 3H, OCH$_3$), 4.2 (t, 2H, C(5)H$_2$), 7.1, 7.48, 7.52 (3×m, 3H, thiophene), 7.21 (s, 1H, ArH7), 8.90 (s, 1H, ArH10), 8.52 and 9.25 (2×d, 2H, thiadiazole), 10.0 (br.s, 1H, NH); hFSHRago (CHO luc) EC$_{50}$=15 nM.

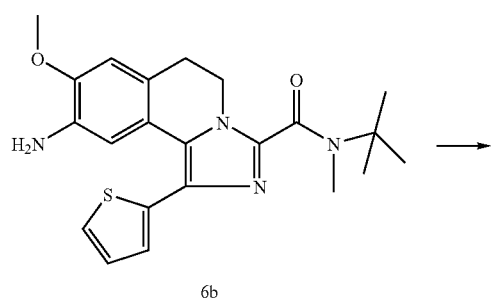

6b

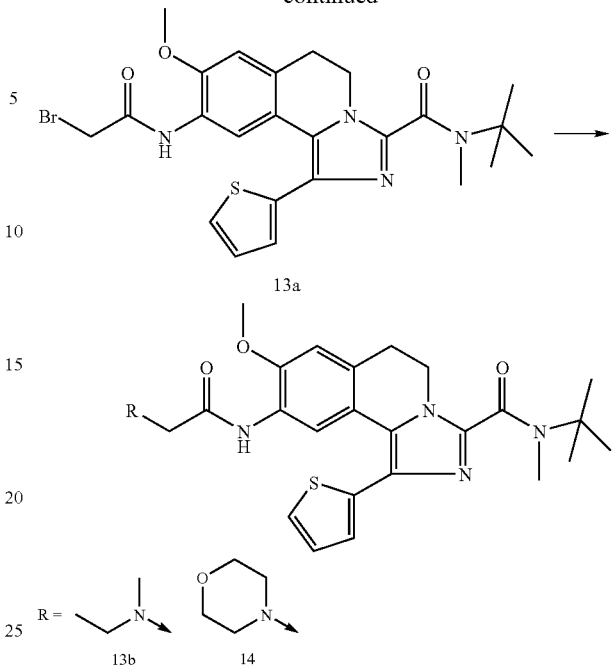

13a 13b  14

Example 13

9-[2-(Ethyl-methyl-amino)-acetylamino]-8-methoxy-1-thiophen-2-yl-5,6-dihydro-imidazo[5,1-a]isoquinoline-3-carboxylic acid tert-butyl-methyl-amide (a). 9-(2-Bromo-acetylamino)-8-methoxy-1-thiophen-2-yl-5,6-dihydro-imidazo[5,1-a]isoquinoline-3-carboxylic acid tert-butyl-methyl-amide To a solution of the product of example 6b (75 mg) and DIPEA (0.16 ml) in dichloromethane (8 ml) was added bromoacetyl bromide (48 μl). After stirring at room temperature for 15 h, the reaction mixture was concentrated in vacuo. The residue was purified by chromatography on silica gel in toluene/acetone [0→50% (v/v)] as eluent.

Yield: 52 mg. LC/MS-ESI: [M+H]$^+$=533.11.

(b). 9-[2-(Ethyl-methyl-amino)-acetylamino]-8-methoxy-1-thiophen-2-yl-5,6-dihydro-imidazo[5,1-a]isoquinoline-3-carboxylic acid tert-butyl-methyl-amide A solution of the product of example 13a (19 mg), DIPEA (19 μl) and N-ethylmethylamine (6.4 μl) in dichloromethane was stirred at room temperature for 2 h. The reaction mixture was concentrated in vacuo. The residue was purified by chromatography on silica gel in toluene/ethyl acetate [0→80% (v/v)] as eluent.

Yield: 8 mg. LC/MS-ESI: [M+H]$^+$=510.3; $^1$H-NMR (CDCl$_3$) δ 1.1 (t, 3H, CH$_3$), δ 1.52 (s, 9H, tert-butyl), 2.35 (s, 3H, NCH$_3$), 2.51 (q, 2H, NCH$_2$), 3.03 (t, 2H, C(6)H$_2$), 3.09 (s, 2H, NCH$_2$), 3.25 (s, 3H, NCH$_3$), 3.9 (s, 3H, OCH$_3$), 4.4 (t, 2H, C(5)H$_2$), 6.78 (s, 1H, H7-Ar), 8.75 (s, 1H, H10-Ar), 7.15, 7.35, 7.5 (m, 3×1H, thiophene), 9.65 (br s, 1H, NH); hFSHRago (CHO luc) EC$_{50}$=26 nM.

Example 14

8-Methoxy-9-(2-morpholin-4-yl-acetylamino)-1-thiophen-2-yl-5,6-dihydro-imidazo[5,1-a]isoquinoline-3-carboxylic acid tert-butyl-methyl-amide

A solution of the product of example 13a (25 mg), DIPEA (49 μl) and morpholine (25 μl) in dichloromethane was stirred at room temperature for 72 h. The reaction mixture was concentrated in vacuo. The residue was purified by preparative HPLC (20→100% acetonitrile) and freeze dried from acetonitrile/water.

Yield: 24 mg. $^1$H-NMR (CDCl$_3$) δ 1.53 (s, 9H, tert-butyl), 2.6 (t, 4H, CH$_2$N morpholine), 3.03 (t, 2H, C(6)H$_2$), 3.1 (s, 2H, CH$_2$N), 3.24 (s, 3H, NCH$_3$), 3.78 (t, 4H, CH$_2$O morpholine), 3.92 (s, 3H, OCH$_3$), 4.38 (m, 2H, C(5)H$_2$), 6.80 (s, 1H, H7-Ar), 8.75 (s, 1H, H10-Ar), 7.15, 7.35, 7.48 (m, 3×1H, thiophene), 9.65 (br s, 1H, NH); hFSHRago (CHO luc) EC$_{50}$=10 nM.

(81 ml) in DMF (500 ml) was stirred at 65° C. for 2 h. The reaction mixture was poured into water and extracted with ethyl acetate. The organic layer was washed with water and brine. The organic layer was dried (MgSO$_4$), filtered and concentrated in vacuo.

Yield: 124 g. $^1$H NMR (CDCl$_3$) δ 1.40 (s, 6H), 3.95 (s, 3H), 4.7 (m, 1H), 6.98 (d, 1H), 7.43 (m, 2H), 9.85 (s, 1H).

(b). 1-Isopropoxy-2-methoxy-4-((E)-2-nitro-vinyl)-benzene

A mixture of the product of example 15a (16.1 g), nitromethane (120 ml) and ammonium acetate (6.1 g) was stirred at 70° C. for 18 h. At room temperature the precipitate was filtered and washed with water and cold ethanol. The solid was dissolved in dichloromethane and washed with brine. The organic layer was dried (MgSO$_4$), filtered and concentrated in vacuo.

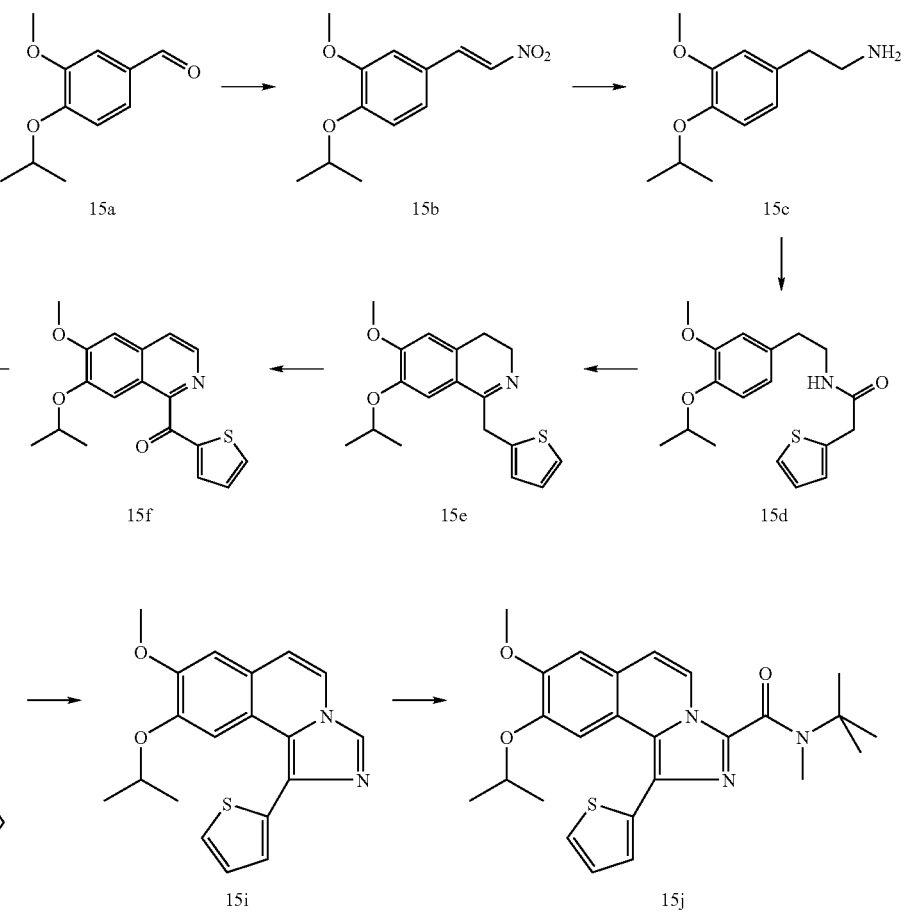

Example 15

9-Isopropoxy-8-methoxy-1-thiophen-2-yl-imidazo[5,1-a]isoquinoline-3-carboxylic acid tert-butyl-methyl-amide

(a). 4-Isopropoxy-3-methoxy-benzaldehyde

A mixture of 4-hydroxy-3-methoxybenzaldehyde (100 g), anhydrous potassium carbonate (182 g) and 2-bromopropane Yield: 13.54 g. $^1$H NMR (CDCl$_3$) δ 1.40 (s, 6H), 3.9 (s, 3H), 4.65 (m, 1H), 6.9 (d, 1H), 7.0 (d, 1H), 7.15 (dd, 1H), 7.52 (d, 1H), 7.95 (d, 1H).

(c). 2-(4-Isopropoxy-3-methoxy-phenyl)-ethylamine

A solution of the product of example 15b (20 g) in THF (80 ml) was added drop wise to a mixture of lithium aluminum hydride (12.8 gram) in dry ether (70 ml) and dry THF (70 ml). The reaction mixture was heated under reflux for 2 h. The reaction mixture was quenched by the addition of water (15 ml) in THF (50 ml) followed by the addition of an aqueous NaOH solution (18 ml, 4 N) and H$_2$O (40 ml). The resulting mixture was filtered. The filtrate was concentrated in vacuo. The residue was taken up in ethyl acetate and washed with an aqueous HCl solution (2 N). Solid NaOH was added to the water layer until pH=10. The water layer was extracted with ethyl acetate. The organic layer was washed with brine, dried (MgSO$_4$), filtered and concentrated in vacuo.

Yield: 13.8 g. LC/MS-ESI: [M+H]$^+$=210.1

(d). N-[2-(4-Isopropoxy-3-methoxy-phenyl)-ethyl]-2-thiophen-2-yl-acetamide

To a mixture of the product of example 15c (20.0 g) and DIPEA (30 ml) in dichloromethane (200 ml) at 0° C. was slowly added 2-thiopheneacetyl chloride (13.0 ml). After stirring at room temperature for 18 h, the reaction mixture was concentrated in vacuo and subsequently dissolved in toluene. The solids were removed by filtration. The filtrate was concentrated in vacuo. The residue was purified by chromatography on silica gel in heptane/ethyl acetate [0→90% (v/v)] as eluent. The fractions with product were combined, concentrated in vacuo and the product was recrystallized from diethyl ether. The solids were collected and dried in vacuo (50° C.).

Yield: 7.6 g. LC/MS-ESI: [M+H]$^+$=334.6

(e). 7-Isopropoxy-6-methoxy-1-thiophen-2-ylmethyl-3,4-dihydro-isoquinoline

Phosphorus oxychloride (8.5 ml) was added slowly to a solution of the product of example 15d (7.6 g) in acetonitrile (75 ml). The reaction mixture was stirred at 50° C. for 4 h. The mixture was cooled in an ice-bath and poured carefully into water. The mixture was treated with an aqueous NaOH solution (2 M) until pH≧10. The aqueous layer was extracted with dichloromethane. The organic layer was dried (MgSO$_4$), filtered and concentrated in vacuo. The residue was purified by chromatography on silica gel in dichloromethane/methanol [0→20% (v/v)] as eluent.

Yield: 7.2 g. LC/MS-ESI: [M+H]$^+$=316.2

(f). (7-Isopropoxy-6-methoxy-isoquinolin-1-yl)-thiophen-2-yl-methanone

To a suspension of the product of example 15e (7.2 g) in acetonitrile (200 ml) was added Pd/C (10%; 2.7 g). Air was bubbled through the suspension for 2 h. The suspension was stirred for 18 h. The reaction mixture was concentrated in vacuo. The residue was taken up in xylene (250 ml) and additional Pd/C (4.1 g 10%) was added. After stirring at 140° C. for 18 h, the reaction mixture was filtered, washed with ethyl acetate and dichloromethane. The filtrate was concentrated in vacuo and the residue was purified by chromatography on silica gel in heptane/ethyl acetate [0→60% (v/v)] as eluent.

Yield: 2.5 g. LC/MS-ESI: [M+H]$^+$=330.1

(g). (7-Isopropoxy-6-methoxy-isoquinolin-1-yl)-thiophen-2-yl-methanone oxime

Hydroxylamine.HCl (1.17 g) was added to a solution of the product of example 15f (2.5 g) in pyridine (75 ml). The reaction mixture was stirred at 80° C. for 18 h. The reaction mixture was concentrated in vacuo. The residue was suspended in water. The solid was filtered, washed with water and cold acetone, and dried in vacuo (50° C.) to give an off white solid.

Yield: 2.3 g. LC/MS-ESI: [M+H]$^+$=343.1

(h). C-(7-Isopropoxy-6-methoxy-isoquinolin-1-yl)-C-thiophen-2-yl-methylamine

Zinc powder (2.2 g) was added in portions to a mixture of the product of example 15g (2.25 g), ammonia (60 ml), and ammonium chloride (0.3 g) in ethanol (60 ml). After stirring at 60° C. for 30 min (gas evolution), the reaction mixture was filtered. The solids were washed with ethanol. The filtrate was concentrated in vacuo and co-evaporated three times with ethanol.

Yield: 3.2 g. LC/MS-ESI: [M+H]$^+$=329.4

(i). 9-Isopropoxy-8-methoxy-1-thiophen-2-yl-imidazo[5,1-a]isoquinoline

A mixture of the product of example 15h (2.2 g) and acetic acid diethoxymethyl ester (1.8 ml) in toluene (200 ml) was stirred at 110° C. for 4 h. The reaction mixture was concentrated in vacuo. The residue was purified by chromatography on silica gel in dichloromethane/ethyl acetate [0→25% (v/v)] as eluent Yield: 630 mg. LC/MS-ESI: [M+H]$^+$=339.1

(j). 9-Isopropoxy-8-methoxy-1-thiophen-2-yl-imidazo[5,1-a]isoquinoline-3-carboxylic acid tert-butyl-methyl-amide To a suspension of the product of example 15i (348 mg) in dry THF (6 ml) was added at −40° C. n-BuLi (0.7 ml 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (5 ml) and N-ethylmorpholine (340 µl) were added N-methyl-tert-butylamine (247 µl) and TBTU (528 mg). After stirring at room temperature for 2 h, the reaction mixture was poured in an aqueous NH$_4$Cl solution (5%). The mixture was extracted with ethyl acetate. The organic layer was dried (MgSO$_4$), filtered and concentrated in vacuo. The residue was purified by chromatography on silica gel in toluene/ethyl acetate [0→50%] as eluent. The fractions with product combined and concentrated in vacuo and the residue was triturated with diethyl ether and dried in vacuo (50° C.).

Yield: 145 mg. MS-ESI: [M+H]$^+$=452.3; Mp: 163-164° C.; $^1$H-NMR (CDCl$_3$) δ 1.29 (d, 6H, isopropoxy CH$_3$), 1.58 (s, 9H, tert-butyl), 3.31 (s, 3H, NCH$_3$), 3.95 (s, 3H, OCH$_3$), 4.23 (m, 1H, —CH), 6.85 (d, 1H, H6), 7.03 (s, 1H7), 7.18, 7.33, 7.47 (3×m, 3H, thiophene), 7.52 (s, 1H, H10-Ar), 8.62 (d, 1, H5 (CHO luc) EC$_{50}$=6.5 nM.

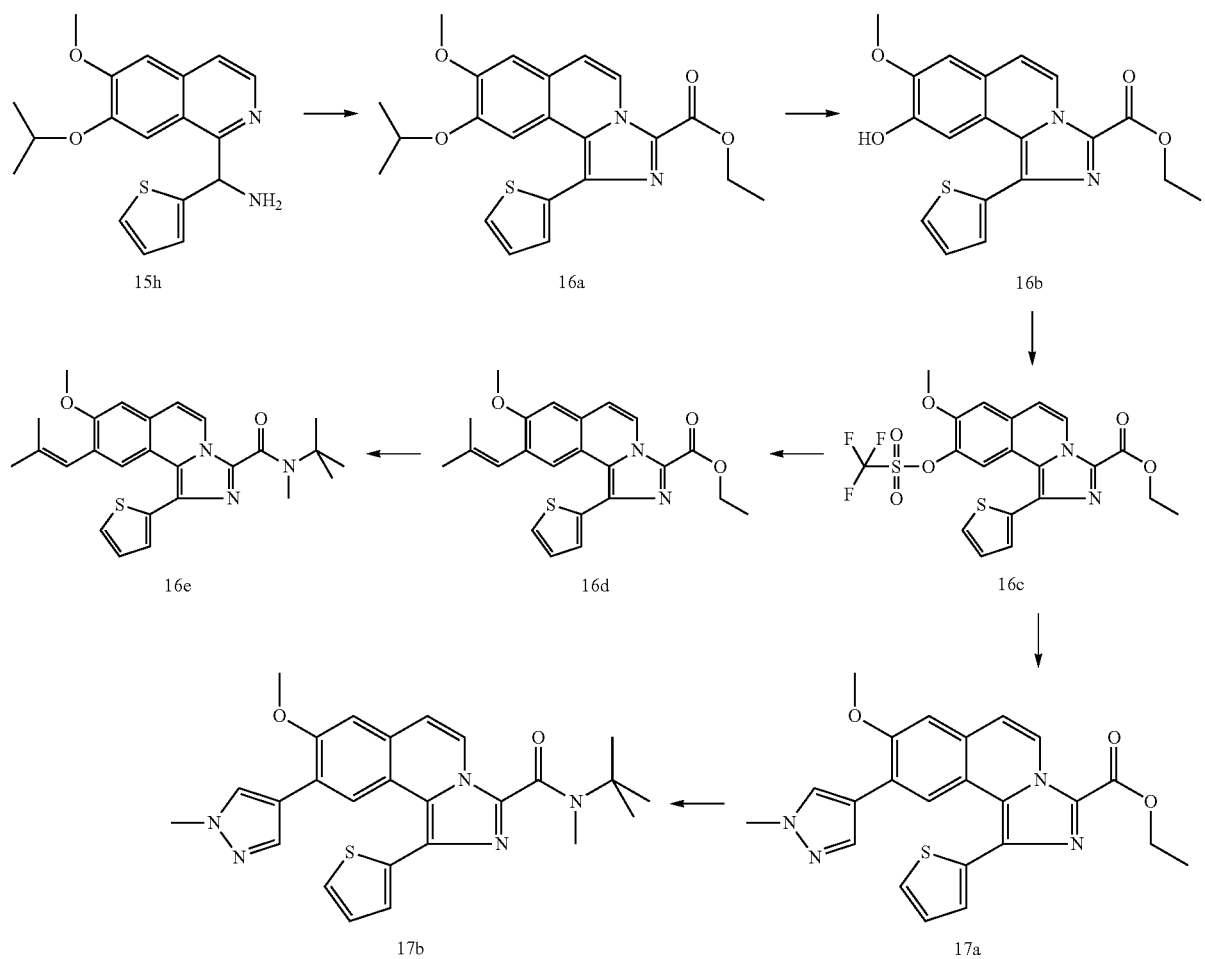

Example 16

8-Methoxy-9-(2-methyl-propenyl)-1-thiophen-2-yl-imidazo[5,1-a]isoquinoline-3-carboxylic acid tert-butyl-methyl-amide (a). 9-Isopropoxy-8-methoxy-1-thiophen-2-yl-imidazo[5,1-a]isoquinoline-3-carboxylic acid ethyl ester Ethyl oxalyl chloride (6.81 ml) was added drop wise to a mixture of the product of example 15h (5.0 g) and pyridine (38 ml) in dichloromethane (180 ml). After stirring at room temperature for 4 h, the reaction mixture was poured in water and extracted with dichloromethane. The organic layer was washed with water, brine, dried (MgSO$_4$), filtered and concentrated in vacuo. The residue was purified by chromatography on silica gel in toluene/ethyl acetate [0→90% (v/v)] as eluent. The fractions with product were combined, concentrated in vacuo and recrystallized from heptane/ethyl acetate. The solids were collected and dried in vacuo (50° C.).

Yield: 907 mg. LC/MS-ESI: [M+H]$^+$=411.2; Mp: 157° C.

(b). 9-Hydroxy-8-methoxy-1-thiophen-2-yl-imidazo [5,1-a]isoquinoline-3-carboxylic acid ethyl ester To a solution of the product of example 16a (4.7 g) in dichloromethane (70 ml) was added methanesulfonic acid (12.0 ml). The yellow solution was stirred at room temperature for 48 h. The reaction mixture was poured in a saturated aqueous NaHCO$_3$ solution. The solids were filtered and washed with water. The solids were dissolved in dichloromethane/methanol. The solution was dried (MgSO$_4$), filtered and concentrated in vacuo. The residue was purified by chromatography on silica gel in dichloromethane/methanol [0→3% (v/v)] as eluent.

Yield: 3.85 g. LC/MS-ESI: [M+H]$^+$=369.1

(c). 8-Methoxy-1-thiophen-2-yl-9-trifluoromethanesulfonyloxy-imidazo[5,1-a]isoquinoline-3-carboxylic acid ethyl ester Trifluoromethanesulfonic anhydride (1.43 ml) was added to a suspension of the product of example 16b (1.04 g) in pyridine (14 ml). The reaction mixture was stirred at room temperature for 2 h. After the addition of water, the mixture was extracted with dichloromethane. The organic layer was washed with water, brine, dried (MgSO$_4$), filtered and concentrated in vacuo. The residue was purified by chromatography on silica gel in toluene/ethyl acetate [0→80% (v/v)] as eluent.

Yield: 850 mg. LC/MS-ESI: [M+H]$^+$=501.1; TLC R$_f$=0.27 (heptane/ethyl acetate 1:1).

(d). 8-Methoxy-9-(2-methyl-propenyl)-1-thiophen-2-yl-imidazo[5,1-a]isoquinoline-3-carboxylic acid ethyl ester A suspension of the product of example 16c (400 mg), 18a (389 mg) and K$_2$CO$_3$ (168 mg) in DME (5 ml) and water (1 ml) was deoxygenated by sparging N$_2$ for several minutes. Pd(PPh$_3$)$_4$ (92 mg) was added and the mixture was stirred at 90° C. for 3 h. The reaction mixture was cooled, poured in water and extracted with ethyl acetate. The organic layers were washed with brine, dried (MgSO$_4$), filtered and concentrated in vacuo. The residue was purified by chromatography on silica gel in toluene/ethyl acetate [0→50% (v/v)] as eluent.

Yield: 260 mg. LC/MS-ESI: [M+H]$^+$=407.1; TLC R$_f$=0.48 (toluene/ethyl acetate 3:2);

(e). 8-Methoxy-9-(2-methyl-propenyl)-1-thiophen-2-yl-imidazo[5,1-a]isoquinoline-3-carboxylic acid tert-butyl-methyl-amide To a suspension of sodium hydride (60% dispersion in oil; 22.1 mg) in DMSO (2 ml) was added N-methyl-tert-butylamine (147 µl) (gas evolution). After stirring at room temperature for 10 min, a solution of the product of example 16d (250 mg) in DMSO/DMF [4 ml 1:1 (v/v)] was added. The mixture was stirred at 70° C. for 72 h. DIPEA (250 µl) and TBTU (400 mg) were added. The reaction mixture was stirred at room temperature for 1 h. The mixture was poured slowly into water and extracted with ethyl acetate. The organic layer was washed with a saturated aqueous NH$_4$Cl solution, brine, dried (MgSO$_4$), filtered and concentrated in vacuo. The residue was purified by chromatography on silica gel in heptane/ethyl acetate [0→40% (v/v)] as eluent. The fractions with product were combined, concentrated in vacuo and recrystallized from ethanol/water. The solids were collected and dried in vacuo (50° C.).

Yield: 70 mg. LC/MS-ESI: [M+H]$^+$=448.2; Mp: 121-123° C.; $^1$H-NMR (CDCl$_3$) δ 1.55 (m, 9H, tert-butyl), 1.63, 1.9 (2×d, 6H, 2×-CH$_3$), 3.3 (s, 3H, NCH$_3$), 3.93 (s, 3H, OCH$_3$), 6.3-8.65 (m, 8H, Ar—H); hFSHRago (CHO luc) EC$_{50}$=9 nM.

Example 17

8-Methoxy-9-(1-methyl-1H-pyrazol-4-yl)-1-thiophen-2-yl-imidazo[5,1-a]isoquinoline-3-carboxylic acid tert-butyl-methyl-amide (a). 8-Methoxy-9-(1-methyl-1H-pyrazol-4-yl)-1-thiophen-2-yl-imidazo[5,1-a]isoquinoline-3-carboxylic acid ethyl ester A mixture of the product of example 16c (140 mg), K$_2$CO$_3$ (100 mg) and 1-methyl-4-(4,4,5,5-tetramethyl-1,3,2-dioxaborolan-2-yl)-1H-pyrazole (150 mg) in DME was deoxygenated by passing through N$_2$ for several minutes. Pd(PPh$_3$)$_4$ (30 mg) was added. The reaction mixture was stirred in a microwave oven at 120° C. for 15 min. The reaction mixture was cooled, poured into water and extracted with ethyl acetate. The organic layer was washed with brine, dried (MgSO$_4$), filtered and concentrated in vacuo. The residue was purified by chromatography on silica gel in toluene/ethyl acetate [0→70% (v/v)] as eluent.

Yield: 65 mg. LC/MS-ESI: [M+H]$^+$=433.1; TLC R$_f$=0.24 (toluene/ethyl acetate 3:2).

(b). 8-Methoxy-9-(1-methyl-1H-pyrazol-4-yl)-1-thiophen-2-yl-imidazo[5,1-a]isoquinoline-3-carboxylic acid tert-butyl-methyl-amide To a solution of the product of example 17a (60 mg) in NMP (3 ml) was added solid NaOH (20 mg). After stirring at 70° C. for 5 h, the reaction mixture was cooled to room temperature. N-methyl-tert-butylamine (50 µl), DIPEA (121 µl) and TBTU (89 mg) were added. The reaction mixture was stirred at room temperature for 2 h. The mixture was poured in a saturated NH$_4$Cl solution and extracted with ethyl acetate. The organic layer was washed with brine, dried (MgSO$_4$), filtered and concentrated in vacuo. The residue was purified by chromatography on silica gel in heptane/ethyl acetate [0→50% (v/v)] as eluent. The fractions containing product were combined and concentrated in vacuo. The remaining residue was crystallized from heptane/ethyl acetate. The solids were collected and dried in vacuo (50° C.).

Yield: 33 mg. LC/MS-ESI: [M+H]$^+$=474.2; Mp: 239-241° C.; TLC R$_f$=0.22 (heptane/ethyl acetate); $^1$H-NMR (CDCl$_3$) δ 1.55 (s, 9H, tert-butyl), 3.34 (s, 3H, NCH$_3$), 3.92, 4.02 (s, 2×3H, OCH$_3$+NCH$_3$-pyrrazole), 6.89 (d, 1, H6), 7.09 (s, 1, H7-Ar), 7.61 (s, 1, H10-Ar), 8.39 (s, 1, H5), 7.62 and 7.80 (2×s, 2H, pyrazole), 7.24, 7.41 and 7.52 (3×m, 3, thiophene); hFSHRago (CHO luc) EC$_{50}$=23 nM.

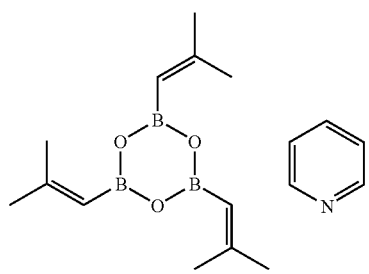

18a

↓

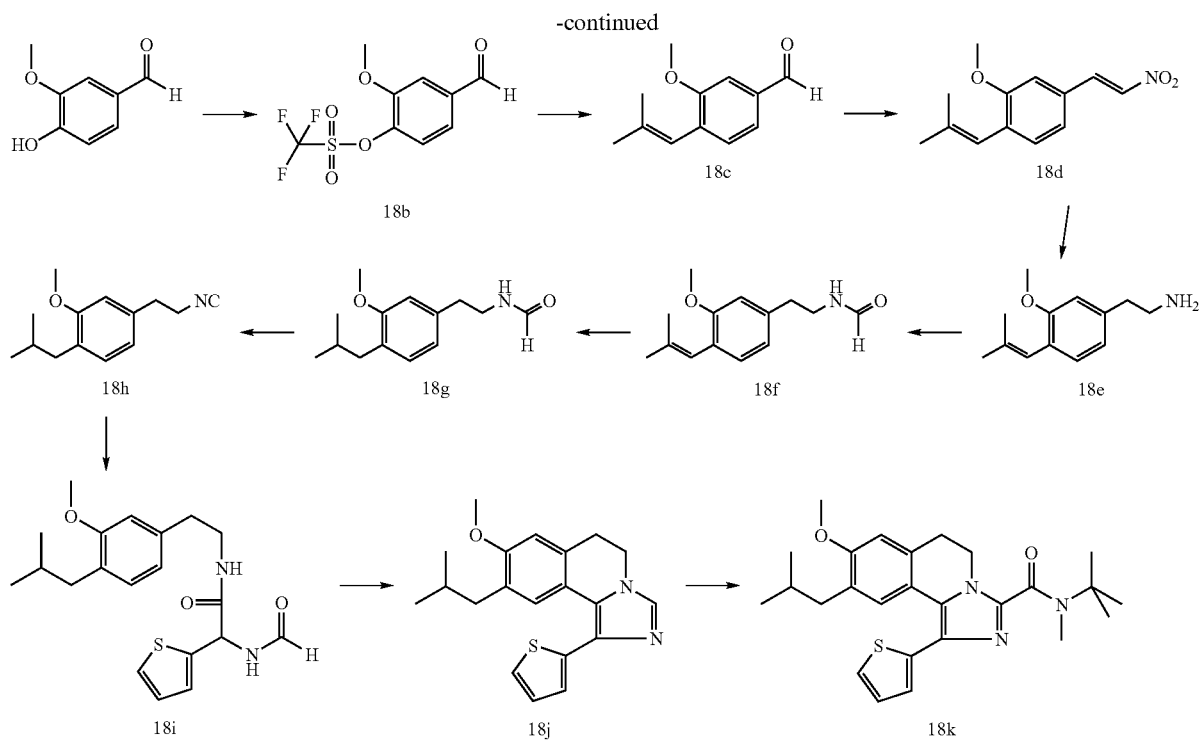

Example 18

9-Isobutyl-8-methoxy-1-thiophen-2-yl-5,6-dihydro-imidazo[5,1-a]isoquinoline-3-carboxylic acid tert-butyl-methyl-amide (a). 2,4,6-Tris-(2-methyl-propenyl)-cyclotriboroxane pyridine 2-Methyl-1-propenylmagnesium bromide in THF (536 ml 0.5 M) was added drop wise to a solution of trimethyl borate (54 ml) in THF (320 ml) at −70° C. The reaction mixture was stirred at −70° C. for 30 min. An aqueous HCl solution (2N) was added. The reaction mixture was stirred at room temperature for 1 h. The pH was adjusted to 4 by adding an aqueous HCl solution (2N). The reaction mixture was extracted with ether. The organic layer was washed with brine, dried (MgSO$_4$), filtered and concentrated in vacuo. A solution of the residue in pyridine (80 ml) was stirred overnight at room temperature. The reaction mixture was concentrated in vacuo. Residual pyridine was removed by co-evaporation with toluene. The residue was dried at room temperature in vacuo (3 mm) for 1 h.

Yield: 27.5 g. Mp: 57-68° C.; $^1$H-NMR (CDCl$_3$) δ 1.9, 2.1 (2×s, 2×3H, —CH$_3$), 5.22 (s, 1H, —CH), 7.2-8.7 (m, 5H, pyridine).

(b). Trifluoro-methanesulfonic acid 4-formyl-2-methoxy-phenyl ester

To a stirred solution of 4-hydroxy-3-methoxybenzaldehyde (30.0 g) and pyridine (39.2 g) in dichloromethane (200 ml) was added drop wise at −30° C. a solution of trifluoromethanesulfonic anhydride (66.8 g) in dichloromethane (100 ml) over a period of 10 min. The temperature was raised to −20° C. and kept there for 15 min. The reaction mixture was poured in ice water (2 l) and extracted with dichloromethane. The combined organic layers were washed with an aqueous HCl solution (2 N), water, a saturated sodium bicarbonate solution, brine, dried (MgSO$_4$), filtered and concentrated in vacuo. The residue was purified by chromatography on silica gel with heptane/ethyl acetate [1:1 (v/v)] as eluent.

Yield: 54.5 g. MS-ESI: [M+H]$^+$=153.3; TLC R$_f$=0.65 (heptane/ethyl acetate 1:1).

(c). 3-Methoxy-4-(2-methyl-propenyl)-benzaldehyde

A mixture of the product of example 18a (22.0 g) and example 18b (15.8 g) in DME (350 ml) and water (70 ml) was degassed by bubbling N$_2$ through the mixture for 5 min. K$_2$CO$_3$ (12.6 g) and Pd(PPh$_3$)$_4$ (2.4 g) were added. The reaction mixture was heated at 90° C. for 4 h. The reaction mixture was concentrated in vacuo and diluted with water. The aqueous layer was extracted with ethyl acetate. The combined organic layers were washed with brine, dried (MgSO$_4$), filtered and concentrated in vacuo. The residue was purified by chromatography on silica gel with heptane/ethyl acetate [9:1 (v/v)] as eluent.

Yield: 15.3 g. NMR (CDCl$_3$) δ 1.83, 1.97 (2×s, 6, CH$_3$), 3.90 (s, 3, OCH$_3$), 6.35 (br s, 1, CH=C), 9.95 (s, CHO).

(d). 2-Methoxy-1-(2-methyl-propenyl)-4-((E)-2-nitro-vinyl)-benzene

This product was prepared in a similar manner as described for example 1d starting from the product of example 18c (13.9 g).

Yield: 17.0 g. Mp 100-101° C.; NMR (CDCl$_3$) δ 1.83, 1.96 (2×s, 6, CH$_3$), 3.87 (s, 3, OCH$_3$), 6.33 (br s, 1, CH=), 7.58 and 7.98 (2×dd, 2, CH=CH), 6.97, 7.13, 7.25 (3H, ArH), 7.58, 7.98 (2×d, olefin-H).

(e). 2-[3-Methoxy-4-(2-methyl-propenyl)-phenyl]-ethylamine

This product was prepared in a similar manner as described for example 1e starting from the product of example 18d (13.0 g).

Yield: 8.5 g. NMR (CDCl$_3$) δ 2.73, 2.97 (2×t, CH2-CH2), 3.82 (s, 3, OCH$_3$), 1.80 and 1.83 (2×d, 6, (CH3)$_2$C=), 6.28 (br s, 1, CH=), 6.68, 6.77, 7.11 (3H, Ar—H).

(f). N-{2-[3-Methoxy-4-(2-methyl-propenyl)-phenyl]-ethyl}-formamide

The product of example 18e (7.7 g) was heated at 70° C. in ethyl formate (100 ml) for 8 h. The reaction mixture was concentrated in vacuo. The residue was purified by chromatography on silica gel in dichloromethane/ethyl acetate [2:1→1:1(v/v)] as eluent.

Yield: 5 g. $^1$H-NMR (CDCl$_3$) δ 1.8, 1.9 (2×s, 6H, CH$_3$), 2.83 (t, 2H, CH$_2$), 3.6 (q, 2H, CH$_2$), 3.82 (s, 3H, OCH$_3$), 5.55 (br.s, 1H, NH), 6.27 (s, 1H, —CH), 6.7-7.13 (m, 3H, ArH), 8.15 (s, 1H, CHO).

(g). N-[2-(4-Isobutyl-3-methoxy-phenyl)-ethyl]-formamide

To a solution of the product of example 18f (5 g) in ethyl acetate (100 ml) was added Pd/C (1 g 10%). The mixture was hydrogenated in a Parr apparatus for 18 h. The reaction mixture was filtered over decalite and washed with ethyl acetate. The filtrate was concentrated in vacuo to give the product which is used as is in the next reaction.

Yield: 5 g. $^1$H-NMR (CDCl$_3$) δ 0.8 (d, 6H, 2×CH$_3$), 1.8 (m, 1H, CH), 2.39 (d, 2H, ArCH$_2$), 2.73 (t, 2H, CH$_2$), 3.5 (q, 2H, CH$_2$), 3.72 (s, 3H, OCH$_3$), 5.55 (br.s, 1H, NH), 6.7-6.95 (m, 3H, ArH), 8.08 (s, 1H, CHO).

(h). 1-Isobutyl-4-(2-isocyano-ethyl)-2-methoxy-benzene

The product of example 18g (5.0 g) was dissolved in dry THF (100 ml) and Et$_3$N (14.8 ml) was added. The solution was cooled to −20° C. POCl$_3$ (1.98 ml) was added drop wise in approximately 10 min. After stirring for 1 h at −20° C., ice water (200 ml) was added. The mixture was stirred at room temperature for 1.5 h. The reaction mixture was extracted with ethyl acetate (150 ml). The organic layer was washed with brine, dried (MgSO$_4$), filtered and concentrated in vacuo. The residue was purified by chromatography on silica gel (heptane/ethyl acetate 2/1(v/v)) as eluent.

Yield: 4 g. $^1$H-NMR (CDCl$_3$) δ 0.88 (d, 6H, 2×CH$_3$), 1.88 (m, 1H, CH), 2.45 (d, 2H, ArCH$_2$), 2.95 (t, 2H, CH$_2$), 3.6 (t, 2H, CH$_2$), 3.8 (s, 3H, OCH$_3$), 6.7, 7.03 (m, 3H, ArH).

(i). 2-Formylamino-N-[2-(4-isobutyl-3-methoxy-phenyl)-ethyl]-2-thiophen-2-yl-acetamide A mixture of the product of example 18h (4.0 g), 2-thiophenecarboxaldehyde (1.92 g) and ammonium formate (2.55 g) in methanol (40 ml) was refluxed for 18 h. At room temperature, the mixture was concentrated to a small volume. Water (150 ml) was added. The product was extracted with ethyl acetate (100 ml). The organic layer was washed with water, brine, dried (MgSO$_4$), filtered and concentrated in vacuo. The residue was purified by chromatography on silica gel in toluene/ethyl acetate [1:1 (v/v)] as eluent. The product was crystallized from diisopropylether/heptane.

Yield: 4.0 g. Mp: 69-71° C.; $^1$H-NMR (CDCl$_3$) δ 0.88 (d, 6H, 2×CH$_3$), 1.88 (m, 1H, CH), 2.45 (d, 2H, ArCH$_2$), 2.75 (m, 2H, CH$_2$), 3.48, 3.62 (2×m, 2H, CH$_2$), 3.75 (s, 3H, OCH$_3$), 5.7 (d, 1H, CH), 5.78 (br.s, 1H, NH), 6.5-7.02 (m, ArH), 8.2 (s, 1H, CHO).

(j). 9-Isobutyl-8-methoxy-1-thiophen-2-yl-5,6-dihydro-imidazo[5,1-a]isoquinoline Phosphoruspentoxide (7.2 g) was added to a stirred mixture of methanesulfonic acid (76 ml). The mixture was heated at 75° C. for 30 min (most of the P$_2$O$_5$ had dissolved). The product of example 18i (3.8 g) was added drop wise. The reaction mixture was stirred at 75° C. for 2 h. At room temperature, the reaction mixture was poured to a NaHCO$_3$/water mixture. The mixture was extracted with ethyl acetate. The organic layer was washed with brine, dried (MgSO$_4$), filtered and concentrated in vacuo. The residue was purified by chromatography on silica gel in toluene/acetone [3:1→1:1 (v/v)] as eluent. The fractions containing product were collected and concentrated in vacuo. The residue was crystallized from diisopropylether, filtered and dried in vacuo (50° C.).

Yield: 1.6 g. Mp: 140° C.; $^1$H-NMR (CDCl$_3$) δ 0.87 (d, 6H, 2×CH$_3$), 1.85 (m, 1H, CH), 2.39 (d, 2H, ArCH$_2$), 3.05 (t, 2H, C(6)H$_2$), 3.83 (s, 3H, OCH$_3$), 4.1 (t, 2H, C(5)H$_2$), 6.72 (s, 1H, ArH7), 7.03, 7.3, 7.37 (m, 3H, thiophene), 7.5 (s, 1H, ArH10), 7.6 (s, 1H, —NCHN—).

(k). 9-Isobutyl-8-methoxy-1-thiophen-2-yl-5,6-dihydro-imidazo[5,1-a]isoquinoline-3-carboxylic acid tert-butyl-methyl-amide To a suspension of the product of example 18j (1.0 g) in dry THF (20 ml) was added at −40° C. an n-BuLi solution (2.07 ml, 1.6 M in heptane). After stirring for 10 min at −40° C., the reaction mixture was poured on CO$_2$ pellets, stirred for 15 min and concentrated in vacuo at 35° C. To a solution of the residue in DMF (20 ml) and N-ethylmorpholine (0.7 ml), were added N-methyl-tert-butylamine (0.7 ml) and TBTU (1.52 g). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel in heptane/ethyl acetate [2:1 (v/v)] as eluent. The fractions with product combined and concentrated in vacuo. The residue was triturated with heptane and dried in vacuo (50° C.).

Yield: 890 mg. UPLC/MS: [M+H]$^+$=452.5; Mp: 124° C.; $^1$H-NMR (CDCl$_3$) δ 0.82 (d, 6H, isopropyl), 1.52 (s, 9H, tert-butyl), 1.8 (m, 1H, —CH), 2.35 (d, 2H, —CH$_2$), 3.04 (t, 2H, C(6)H$_2$), 3.25 (s, 3H, NCH$_3$), 3.82 (s, 3H, OCH$_3$), 4.4 (t, 2H, C(5)H$_2$), 6.72 (s, 1H, ArH7), 7.03, 7.3 (m, 3H, thiophene), 7.42 (s, 1H, ArH10); hFSHRago (CHO luc) EC$_{50}$=8 nM.

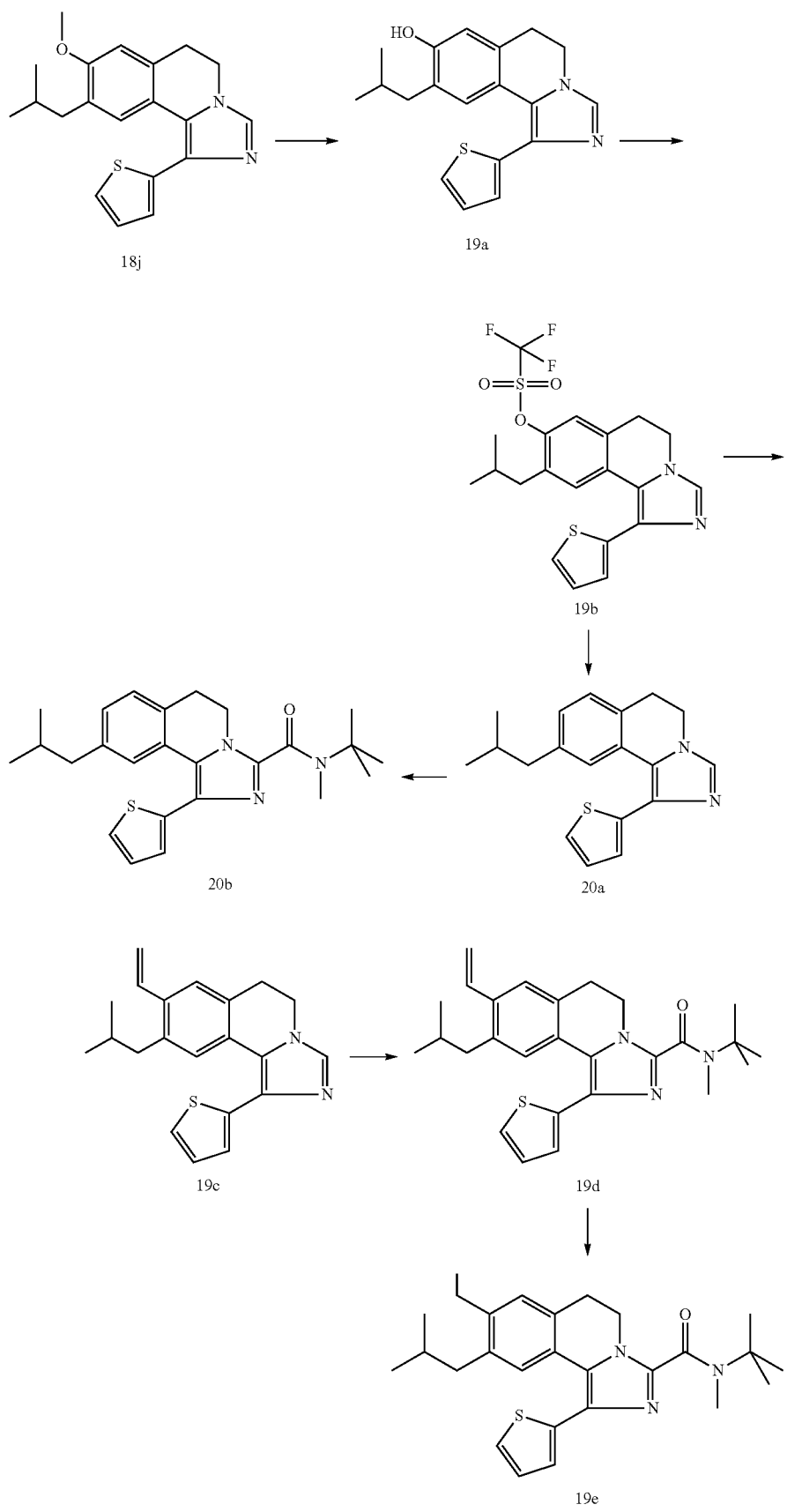

Example 19

8-Ethyl-9-isobutyl-1-thiophen-2-yl-5,6-dihydro-imidazo[5,1-a]isoquinoline-3-carboxylic acid tert-butyl-methyl-amide 9-Isobutyl-1-thiophen-2-yl-8-vinyl-5,6-dihydro-imidazo[5,1-a]isoquinoline-3-carboxylic acid tert-butyl-methyl-amide hydrochloride (a). 9-Isobutyl-1-thiophen-2-yl-5,6-dihydro-imidazo[5,1-a]isoquinolin-8-ol A solution of the product of example 18j (200 mg) in dichloromethane (7 ml) was treated at −50° C. with $BBr_3$ (0.3 ml). After stirring at room temperature for 30 min, the reaction mixture was poured in cold methanol (−50° C.; 10 ml) and subsequently concentrated in vacuo. Ethyl acetate (20 ml) and water (20 ml) were added. The mixture was neutralized with solid $NaHCO_3$. The organic layer was washed with water, dried ($MgSO_4$), filtered and concentrated in vacuo. The residue was triturated with ethyl acetate. The solids were collected and dried in vacuo (50° C.).

Yield: 100 mg. MS-ESI: $[M+H]^+$=325.4; TLC $R_f$=0.15 (toluene/ethyl acetate 1:1); Mp: 281° C.; $^1$H-NMR (DMSO-$d_6$) δ 0.82 (d, 6H, 2×$CH_3$), 1.8 (m, 1H, CH), 2.3 (d, 2H, $ArCH_2$), 2.9 (t, 2H, C(6)$H_2$), 4.08 (t, 2H, C(5)$H_2$), 6.75 (s, 1H, ArH7), 7.05, 7.25, 7.48 (m, 3H, thiophene), 7.4 (s, 1H, ArH10), 7.7 (s, 1H, —NCHN—), 9.48 (s, 1H, OH).

(b). Trifluoromethanesulfonic acid 9-isobutyl-1-thiophen-2-yl-5,6-dihydro-imidazo[5,1-a] isoquinolin-8-yl ester To a suspension of the product of example 19a (100 mg) in dichloromethane (2 ml) was added at −20° C. pyridine (100 μl) followed by trifluoromethanesulfonic anhydride (200 μl). After stirring at room temperature for 1 h, water was added. The mixture was extracted with ethyl acetate. The organic layer was washed with brine, dried ($MgSO_4$), filtered and concentrated in vacuo. The residue was purified by chromatography on silica gel in dichloromethane/ethyl acetate [2:1 (v/v)] as eluent. The combined fractions with product were concentrated in vacuo. The product was treated with heptane to give a white crystalline material.

Yield: 105 mg. MS-ESI: $[M+H]^+$=457.0; Mp: 101-102° C.; TLC $R_f$=0.26 (toluene/ethyl acetate 1:1); $^1$H-NMR ($CDCl_3$) δ 0.9 (d, 6H, 2×$CH_3$), 1.85 (m, 1H, CH), 2.48 (d, 2H, $ArCH_2$), 3.1 (t, 2H, C(6)$H_2$), 4.18 (t, 2H, C(5)$H_2$), 7.15 (s, 1H, ArH7), 7.05, 7.32, 7.38 (m, 3H, thiophene), 7.58 (s, 1H, ArH10), 7.72 (s, 1H, —NCHN—).

(c). 9-Isobutyl-1-thiophen-2-yl-8-vinyl-5,6-dihydro-imidazo[5,1-a]isoquinoline

A mixture of the product of example 19b (100 mg), $K_2CO_3$ (70 mg), Pd(PPh$_3$)$_4$ (10 mg) and 2,4,6-trivinylcyclotriboroxane pyridine complex (130 mg) in an aqueous degassed DME solution (3 ml 10%) was stirred under a $N_2$ atmosphere at 90° C. for 7 h. At room temperature, the reaction mixture was poured in an aqueous $NH_4Cl$ solution (5%). The mixture was extracted with ethyl acetate. The residue was purified by chromatography on silica gel in toluene/ethyl acetate [1:1 (v/v)] as eluent.

Yield: 60 mg. MS-ESI: $[M+H]^+$=335.0; Mp: 118-120° C.; TLC $R_f$=0.28 (toluene/ethyl acetate 1:1); $^1$H-NMR ($CDCl_3$) δ 0.9 (d, 6H, 2×$CH_3$), 1.8 (m, 1H, CH), 2.45 (d, 2H, $ArCH_2$), 3.1 (t, 2H, C(6)$H_2$), 4.13 (t, 2H, C(5)$H_2$), 5.28, 5.66 (2×d, 2H, =$CH_2$), 6.95 (q, 1H, =CH), 7.4 (s, 1H, ArH7), 7.05, 7.32, 7.38 (m, 3H, thiophene), 7.52 (s, 1H, ArH10), 7.6 (s, 1H, —NCHN—).

(d). 9-Isobutyl-1-thiophen-2-yl-8-vinyl-5,6-dihydro-imidazo[5,1-a]isoquinoline-3-carboxylic acid tert-butyl-methyl-amide; hydrochloride salt To a suspension of the product of example 19c (55 mg) in dry THF (1 ml) was added at −40° C. n-BuLi (120 μl 1.6 M in heptane). After stirring for 10 min at −40° C., the reaction mixture was poured on $CO_2$ pellets. The mixture was stirred for 15 min and concentrated in vacuo at 35° C. To a solution of the residue in DMF (1 ml) and N-ethylmorpholine (120 μl), were added N-methyl-tert-butylamine (120 μl) and TBTU (170 mg). After stirring at room temperature for 2 h, the reaction mixture was poured in an aqueous $NH_4Cl$ solution (5%). The mixture was extracted with ethyl acetate. The organic layer was dried ($MgSO_4$), filtered and concentrated in vacuo. The residue was purified by chromatography on silica gel in heptane/ethyl acetate [4:1 (v/v)] as eluent. The fractions with product were combined and concentrated in vacuo. The residue was triturated diethyl ether/HCl and subsequently with ethyl acetate, to provide a white powder, which dried in vacuo (50° C.).

Yield: 30 mg. LC/MS-ESI: $[M+H]^+$=448.3; Mp: 130° C. TLC $R_f$=0.65 (heptane/ethyl acetate 1:1); $^1$H-NMR (DMSO-$d_6$) δ 0.82 (d, 6H, 2×$CH_3$), 1.48 (s, 9H, tert-butyl), 1.68 (m, 1H, —CH), 2.4 (d, 2H, —$CH_2$), 3.08 (m, 5H, C(6)$H_2$+NMe), 4.2 (t, 2H, C(5)$H_2$), 5.3, 5.8 (m, 3H, —CH=$CH_2$), 6.9-7.6 (m, 5H, ArH); hFSHRago (CHO luc) $EC_{50}$=76 nM.

(e). 8-Ethyl-9-isobutyl-1-thiophen-2-yl-5,6-dihydro-imidazo[5,1-a]isoquinoline-3-carboxylic acid tert-butyl-methyl-amide The product of example 19d (83 mg) in ethanol (6 ml) was hydrogenated over Pd/C (120 mg; 10%). After stirring for 2 h at room temperature, the reaction mixture was filtered, washed with ethanol and ethyl acetate. The filtrate was concentrated in vacuo. The residue was purified by preparative HPLC (30→100% acetonitrile).

Yield: 37 mg. LC/MS-ESI: $[M+H]^+$=450.3; $^1$H-NMR ($CDCl_3$) δ 0.88 (d, 6H, iso-butyl), 1.22 (t, 3H, —$CH_3$), 1.52 (s, 9H, tert-butyl), 1.74 (m, 1H, —CH), 2.35 (d, 2H, —$CH_2$), 2.6 (q, 2H, —$CH_2$), 3.03 (t, 2H, C(6)$H_2$), 3.23 (s, 3H, NMe), 4.38 (t, 2H, C(5)$H_2$), 7.08 (s, 1H, ArH7), 7.44 (s, 1H, ArH10), 7.05, 7.3 (m, 3×1H, thiophene); hFSHRago (CHO luc) $EC_{50}$=200 nM.

Example 20

9-Isobutyl-1-thiophen-2-yl-5,6-dihydro-imidazo[5,1-a]isoquinoline-3-carboxylic acid tert-butyl-methyl-amide (a). 9-Isobutyl-1-thiophen-2-yl-5,6-dihydro-imidazo[5,1-a]isoquinoline A mixture of the product of example 19b (450 mg), formic acid (400 μl), tributylamine (3 ml), bis(diphenylphosphino)propane (120 mg), PdCl$_2$.(PPh$_3$)$_2$ (180 mg) in degassed DMF (5 ml) was stirred under $N_2$ at 80° C. for 18 h. At room temperature, the reaction mixture was poured into an aqueous $NaHCO_3$ solution (5%). The mixture was extracted with ethyl acetate. The residue was purified by chromatography on silica gel in heptane/dioxane [1:1 (v/v)] as eluent. The fractions with product were combined, concentrated in vacuo. The remaining residue was triturated with diisopropyl ether to give an off-white solid after drying in vacuo (50° C.).

Yield: 260 mg. MS-ESI: [M+H]$^+$=309.1; TLC R$_f$=0.50 (heptane/dioxane 1:1); Mp: 136° C.; $^1$H-NMR (CDCl$_3$) δ 0.88 (d, 6H, 2×CH$_3$), 1.8 (m, 1H, CH), 2.38 (d, 2H, ArCH$_2$), 3.05 (t, 2H, C(6)H$_2$), 4.13 (t, 2H, C(5)H$_2$), 6.95-7.67 (m, 7H, ArH+thiophene).

(b). 9-Isobutyl-1-thiophen-2-yl-5,6-dihydro-imidazo[5,1-a]isoquinoline-3-carboxylic acid tert-butyl-methyl-amide To a suspension of the product of example 20a (150 mg) in dry THF (2 ml) was added at −40° C. a n-BuLi solution (350 μl, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (2 ml) and N-ethylmorpholine (150 μl), were added N-methyl-tert-butylamine (150 μl) and TBTU (200 mg). After stirring at room temperature for 2 h, the reaction mixture was poured in an aqueous NH$_4$Cl solution (5%). The mixture was extracted with ethyl acetate. The organic layer was dried (MgSO$_4$), filtered and concentrated in vacuo. The residue was purified by chromatography on silica gel in heptane/ethyl acetate as eluent. The fractions with product combined and concentrated in vacuo. The residue was treated with heptane, to provide a white powder and dried in vacuo (50° C.).

Yield: 110 mg. MS-ESI: [M+H]$^+$=422.1; TLC R$_f$=0.50 (heptane/ethyl acetate 2:1); Mp: 126° C.; $^1$H-NMR (CDCl$_3$) δ 0.85 (d, 6H, 2×CH$_3$), 1.53 (s, 9H, tert-butyl), 1.75 (m, 1H, —CH), 2.35 (d, 2H, ArCH$_2$), 3.05 (t, 2H, C(6)H$_2$), 3.22 (s, 3H, NCH$_3$), 4.38 (t, 2H, C(5)H$_2$), 7.06 (m, 1, thiophene), 7.33 (m, 2, thiophene), 6.98 (dd, 1, H8), 7.17 (d, 1, H7), 7.50 (d, 1, H10); hFSHRago (CHO luc) EC$_{50}$=407 nM.

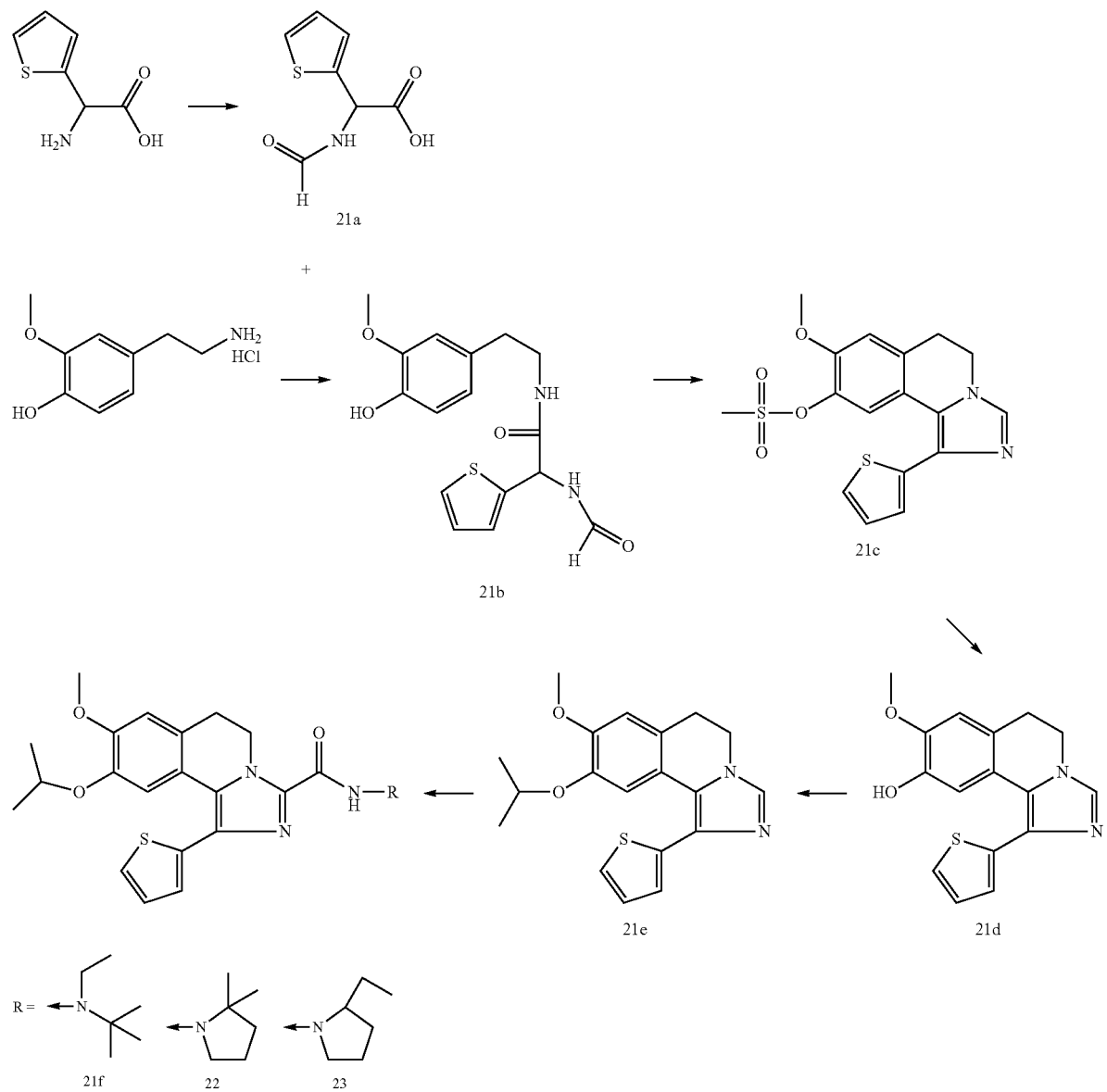

Example 21

9-Isopropoxy-8-methoxy-1-thiophen-2-yl-5,6-dihydro-imidazo[5,1-a]isoquinoline-3-carboxylic acid tert-butyl-ethyl-amide; trifluoro-acetic acid salt

(a). Formylamino-thiophen-2-yl-acetic acid

To a solution of amino-thiophen-2-yl-acetic acid (5 g) in formic acid (50 ml) was added acetic acid (18 ml). After stirring at room temperature for 6 h, water (25 ml) was added. The reaction mixture was stirred for 30 min. The mixture was concentrated in vacuo and triturated with water. The solids were collected by filtration and dried in vacuo (50° C.).

Yield: 3.0 g. Mp: 147-149° C.; $^1$H-NMR (DMSO-$d_6$) δ 5.63 (d, 1H), 7.01, 7.11, 7.50 (3×m, 3H, thiophene), 8.08 (s, 1H, CHO), 9.02 (d, 1H, NH).

(b). 2-Formylamino-N-[2-(4-hydroxy-3-methoxy-phenyl)-ethyl]-2-thiophen-2-yl-acetamide A mixture of the product of example 21a (900 mg), 4-(2-amino-ethyl)-2-methoxy-phenol hydrochloride (1.0 g), N-ethylmorpholine (2 ml), TBTU (2.2 g) and HOBT (50 mg) in DMF (4 ml) was stirred at room temperature for 6 h. The reaction mixture was acidified with an aqueous HCl solution (1 M) and extracted with ethyl acetate. The organic layer was washed with an aqueous NaHCO$_3$ solution, brine, dried (MgSO$_4$), filtered and concentrated in vacuo. The residue was triturated with ethyl acetate and the solids were dried in vacuo (50° C.).

Yield: 1.3 g. ESI-MS: [M+H]$^+$=335.3; TLC R$_f$=0.58 (dichloromethane/acetone 1:1); Mp: 147-149° C.; $^1$H-NMR (DMSO-$d_6$) δ 2.6 (t, 2H, CH$_2$), 3.25 (m, 2H, CH$_2$N), 3.7 (s, 3H, OCH$_3$), 5.73 (d, 1H, —CH), 6.50 (dd, 1H, Ar—H), 6.40 (d, 1H, Ar—H), 6.73 (d, 1H, Ar—H), 6.94 (m, 2H, thiophene), 7.42 (m, 1H, thiophene), 8.20 (s, 1H, CHO), 8.44 (t, 1, NH), 8.69 (s, 1H, OH), 8.85 (d, 1, NH).

(c). Methanesulfonic acid 8-methoxy-1-thiophen-2-yl-5,6-dihydro-imidazo[5,1-a]isoquinolin-9-yl ester The product of example 21b (1.3 g) was stirred in methanesulfonic acid (30 ml) and P$_2$O$_5$ (3 g) at 75° C. for 45 min. At room temperature, the reaction mixture was poured in ice-water and neutralized with solid NaHCO$_3$. The aqueous layer was extracted with ethyl acetate. The organic layer was washed with brine, dried (MgSO$_4$), filtered and concentrated in vacuo. The product was purified by chromatography on silica gel with toluene/acetone as eluent. The isolated material was triturated with ethyl acetate/ether (1/1).

Yield: 0.9 g. MS-ESI: [M+H]$^+$=377.1; TLC R$_f$=0.45 (dichloromethane/methanol 9/1); Mp 206-208° C.; NMR (DMSO-$d_6$) δ 3.08 (t, 2, (6)CH$_2$), 4.18 (t, 2, (5)CH$_2$), 3.90 (s, 3, OCH$_3$), 3.30 (s, 3, CH$_3$SO$_2$), 7.28 (s, 1, H7), 7.60 (s, 1, H10), 7.70 (s, 1, H$_3$), 7.06, 7.51, and 7.30 (3×m, 3, thiophene).

(d). 8-Methoxy-1-thiophen-2-yl-5,6-dihydro-imidazo[5,1-a]isoquinolin-9-ol

A mixture of the product of example 21c (850 mg) and an aqueous solution of NaOH (1.2 g in 5 ml) in methanol (30 ml) was stirred at 65° C. for 2 h. The reaction mixture was concentrated in vacuo to afford a volume of 10 ml. The mixture was neutralized with an aqueous HCl solution (4 M) to pH=7. After stirring at room temperature for 30 min, the solids were collected and dried in vacuo (50° C.).

Yield: 615 mg. MS-ESI: [M+H]=299.3; Mp: 223-224° C.; TLC R$_f$=0.64 (dichloromethane/acetone 1:1). NMR (DMSO) δ 2.93 (t, 2H, H6), 3.80 (s, 1, OCH$_3$), 4.10 (t, 2H, H5), 6.92 (s, 1, H7), 7.26 (s, 1, H10), 7.70 (s, 1, H3), 7.10, 7.27, and 7.47 (3×m, 3, thiophene), 9.0 (s, 1, OH).

(e). 9-Isopropoxy-8-methoxy-1-thiophen-2-yl-5,6-dihydro-imidazo[5,1-a]isoquinoline A mixture of the product of example 21d (400 mg), K$_2$CO$_3$ (2.0 g) and 2-bromo-propane (200 μl) in dry DMF (2.5 ml) was stirred at 60° C. for 6 h. The reaction mixture was diluted with water (20 ml) and a saturated aqueous NH$_4$Cl solution (10 ml). The mixture was extracted with ethyl acetate. The organic layer was washed with water, brine, dried (MgSO$_4$), filtered and concentrated in vacuo. The residue was triturated with isopropyl ether and the solids were collected and dried in vacuo (50° C.).

Yield: 370 mg. TLC R$_f$=0.58 (toluene/acetone 1:1); Mp: 129-130° C.; $^1$H-NMR (DMSO) δ 1.18 (d, 6H, 2×CH$_3$), 2.98 (t, 2H, C(6)H$_2$), 3.78 (s, 3H, OCH$_3$), 4.1 (t, 2H, C(5)H$_2$), 4.18 (m, 1H, CH), 6.98 (s, 1H, ArH7), 7.2 (s, 1H, ArH10), 7.1, 7.25, 7.55 (m, 3H, thiophene), 7.75 (s, 1H, H3).

(f). 9-Isopropoxy-8-methoxy-1-thiophen-2-yl-5,6-dihydro-imidazo[5,1-a]isoquinoline-3-carboxylic acid tert-butyl-ethyl-amide; trifluoro-acetic acid salt To a suspension of the product of example 21e (100 mg) in dry THF (2 ml) was added at −40° C. a n-BuLi solution (239 μl 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (1 ml) and N-ethylmorpholine (100 μl), were added N-ethyl-tert-butylamine (205 μl) and TBTU (141 mg). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by reverse phase preparative HPLC with water/acetonitrile and 2% TFA as eluent.

Yield: 75.1 mg. MS-ESI: [M+H]$^+$=468.5; TLC R$_f$=0.55 (heptane/ethyl acetate 1:1); $^1$H-NMR (CDCl$_3$) δ 1.2 (t, 3H, CH$_3$), 1.25 (d, 9H, 2×CH$_3$), 1.58 (s, 9H, tert-butyl), 3.05 (t, 2H, C(6)H$_2$), 3.75 (q, 2H, CH$_2$), 3.89 (s, 3H, OCH$_3$), 4.18 (m, 1H, CH), 4.3 (t, 2H, C(5)H$_2$), 6.77 (s, 1H, ArH7), 7.15 (s, 1H, ArH10), 7.1, 7.4 (m, 3×1H, thiophene); hFSHRago (CHO luc) EC$_{50}$=0.9 nM.

Example 22

(2,2-Dimethyl-pyrrolidin-1-yl)-(9-isopropoxy-8-methoxy-1-thiophen-2-yl-5,6-dihydro-imidazo[5,1-a]isoquinolin-3-yl)-methanone; trifluoro-acetic acid salt To a suspension of the product of example 21e (100 mg) in dry THF (2 ml) was added at −40° C. a n-BuLi solution (238 μl 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (1 ml) and N-ethylmorpholine (100 μl) were added 2,2-dimethyl-pyrrolidine (159 mg) and TBTU (141 mg). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by reverse phase preparative HPLC with water/acetonitrile and 2% TFA as eluent.

Yield: 61.1 mg. MS-ESI: [M+H]⁺=466.3; TLC $R_f$=0.44 (heptane/ethyl acetate 1:1); ¹H-NMR (CDCl₃) δ 1.25 (d, 9H, 2×CH₃), 1.58 (s, 6H, 2×CH₃), 1.9 (m, 4H, 2×CH₂-pyrrolidine), 3.08 (t, 2H, C(6)H₂), 3.89 (s, 3H, OCH₃), 3.9 (t, 2H, —NCH₂-pyrrolidine), 4.18 (m, 1H, CH), 4.45 (t, 2H, C(5) H₂), 6.77 (s, 1H, ArH7), 7.08 (s, 1H, ArH10), 7.12, 7.38, 7.44 (3×m, 3H, thiophene); hFSHRago (CHO luc) EC₅₀=3 nM.

Example 23

(2-Ethyl-pyrrolidin-1-yl)-(9-isopropoxy-8-methoxy-1-thiophen-2-yl-5,6-dihydro-imidazo[5,1-a] isoquinolin-3-yl)-methanone; trifluoro-acetic acid salt To a suspension of the product of example 21e (100 mg) in dry THF (2 ml) was added at −40° C. a n-BuLi solution (238 μl, 1.6 M in heptane). After stirring for 10 min at −40° C., the reaction mixture was poured on CO₂ pellets. The mixture was stirred for 15 min and concentrated in vacuo at 35° C. To a solution of the residue in DMF (1 ml) and N-ethylmorpholine (100 μl), were added 2-ethyl-pyrrolidine (146 mg) and TBTU (141 mg). After stirring at room temperature for 2 h, the reaction mixture was poured in an aqueous NH₄Cl solution (5%) and extracted with ethyl acetate. The organic layer was dried (MgSO₄), filtered and concentrated in vacuo. The residue was purified by reverse phase preparative HPLC with water/acetonitrile and 2% TFA as eluent.

Yield: 83.7 mg. MS-ESI: TLC $R_f$=0.48 (heptane/ethyl acetate 1:1); [M+H]⁺=466.5; ¹H-NMR (DMSO-d₆) δ 0.82, 0.88 [2×t, 3H, ethyl (rotamers)], 1.15 (2×dd, 6H, isopropoxy), 2.96 (t, 2H, H6), 3.90 (t, 2H, H5), 3.78 (s, 3H, OCH₃), 7.0 (2×s, 1H, H7), 7.12, 7.21 (2×s, 1H, H10), 7.12 (m, 1H, H-thiophene), 7.31 (ddm 1H, H-thiophene), 7.59 (m, 1H, H-thiophene); hFSHRago (CHO luc) EC₅₀=63 nM.

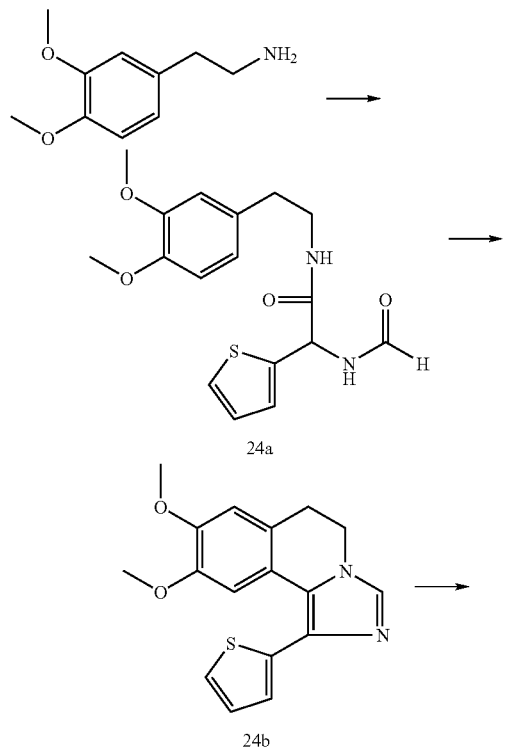

24a

24b

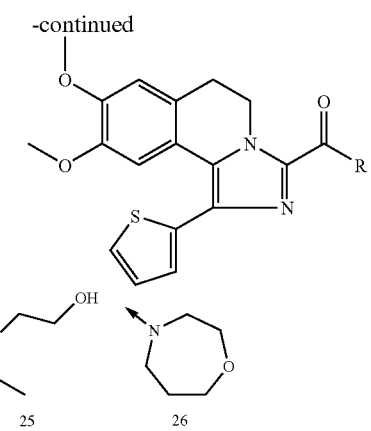

24c  25  26

Example 24

(2-Methyl-pyrrolidin-1-yl)-(9-methoxy-8-methoxy-1-thiophen-2-yl-5,6-dihydro-imidazo[5,1-a]isoquinolin-3-yl)-methanone; hydrochloride salt (a). N-[2-(3,4-Dimethoxy-phenyl)-ethyl]-2-formylamino-2-thiophen-2-yl-acetamide A mixture of the product of example 21a (900 mg), 2-(3, 4-dimethoxy-phenyl)-ethylamine (1 ml), N-ethylmorpholine (0.75 ml) and TBTU (1.7 g) in DMF (5 ml) was stirred at room temperature for 4 h. The reaction mixture was poured in ice water and extracted with ethyl acetate. The organic layer was washed with water, brine, dried (MgSO₄), filtered and concentrated in vacuo. The residue was treated with tert-butyl-methyl ether to give a white powder.

Yield: 1.2 g. Mp: 147-150° C.; TLC $R_f$=0.66 (dichloromethane/acetone 1:1); ¹H-NMR (DMSO-d₆) δ 2.65 (t, 2H, CH₂), 3.27 (m, 2H, CH₂), 3.7 (2×s, 6H, 2×OCH₃), 5.73 (d, 1H, CH), 6.65 (dd, 1, Ar—H), 6.78 (d, 1, Ar—H), 6.82 (d, 1, Ar—H), 6.95 (m, 2, thiophene), 7.42 (m, 1, thiophene), 8.03 (s, 1, CHO), 8.45 (t, 1, NH), 8.85 (d, 1, NH).

(b). 8,9-Dimethoxy-1-thiophen-2-yl-5,6-dihydro-imidazo[5,1-a]isoquinoline

The product of example 24a (1.2 g) was stirred in methanesulfonic acid (30 ml) and P₂O₅ (3 g) at 75° C. for 45 min. At room temperature, the reaction mixture was poured in ice-water and neutralized with solid NaHCO₃. The aqueous layer was extracted with ethyl acetate. The organic layer was washed with brine, dried (MgSO₄), filtered and concentrated in vacuo. The residue was purified by chromatography on silica gel in toluene/acetone [1:1 (v/v)] as eluent.

Yield: 680 mg. MS-ESI: [M+H]⁺=313.0; Mp: 146-147° C.; TLC $R_f$=0.50 (toluene/acetone 1:1); ¹H-NMR (CDCl₃) δ 3.05 (t, 2H, C(6)H₂), 3.7, 3.9 (2×s, 6H, 2×OCH₃), 4.13 (t, 2H, C(5)H₂), 6.76 (s, 1H, ArH7), 7.07, 7.33, 7.38 (3×m, 3H, thiophene), 7.39 (s, 1H, ArH10), 7.52 (s, 1H, NCHN).

(c). (2-Methyl-pyrrolidin-1-yl)-(9-methoxy-8-methoxy-1-thiophen-2-yl-5,6-dihydro-imidazo-[5,1-a] isoquinolin-3-yl)-methanone; hydrochloride salt To a suspension of the product of example 24b (171 mg) in dry THF (2 ml) was added at −40° C. a n-BuLi solution (342 μl, 1.6 M in heptane). After stirring for 10 min at −40° C., the reaction mixture was poured on CO₂ pellets. The mixture was stirred for 15 min and concentrated in vacuo at 35° C. To a solution of the residue in DMF (2 ml) and N-ethylmorpholine (214 µl), were added 2-methyl-pyrrolidine (318 µl) and TBTU (320 mg). After stirring at room temperature for 2 h, the reaction mixture was poured in an aqueous NH₄Cl solution (5%) and extracted with ethyl acetate. The organic layer was dried (MgSO₄), filtered and concentrated in vacuo. The residue was purified by chromatography on silica gel with heptane/ethyl acetate as eluent. The fractions with product combined and concentrated in vacuo. The residue was treated with heptane, to provide a white powder and dried in vacuo (50° C.).

Yield: 71.0 mg. MS-ESI: [M+H]⁺=424.3; ¹H-NMR (DMSO-d₆) [mixture of rotamers] δ 1.18, 1.24 (2×d, 3H, CH₃ pyrrolidine), 1.52-2.10 (m, 4H, CH₂CH₂ pyrrolidine), 2.98 (m, 2H, H6), 3.55, 3.57 (2×s, 3H, OCH₃), 3.80 (s, 3H, OCH₃), 3.90 (m, 2H, NCH₂), 4.38, 4.46 (2×m, 2H, H5), 4.23, 4.93 [2×m, 1H, CH(CH₃)], 7.01 (2×s, 1H, H7), 7.13 (m, 1H, thienyl), 7.30 (2×s, 1H, H10), 7.38, 7.41 (2×d, 1H, thienyl), 7.57 (m, 1H, thienyl); hFSHRago (CHO luc) EC₅₀=333 nM.

Example 25

8,9-Dimethoxy-1-thiophen-2-yl-5,6-dihydro-imidazo[5,1-a]isoquinoline-3-carboxylic acid (2-hydroxy-ethyl)-isopropyl-amide; hydrochloride salt Coupling of the product of example 24a (180 mg) with 2-isopropylamino-ethanol (100 mg) was performed according to the method described in example 24c.

Yield: 42.0 mg. MS-ESI: [M+H]⁺=442.5; ¹H-NMR (DMSO-d₆) [mixture of rotamers] δ 1.20-1.30 (m, 6H, 2×CH₃ isopropyl), 2.98, 3.06 (2×m, 2H, H6), 3.40-3.70 (m, 2H, CH₂CH₂OH), 3.58, 3.80 (2×s, 6H, OCH₃), 4.18, 4.58 (2×m, 2H, H5), 4.33, 4.72 [2×m, 1HCH(CH₃)₂], 7.02, 7.05 (2×s, 1H, H7), 7.13, 7.16 (2×m, 1H, thienyl), 7.28 (2×s, 1H, H10), 7.40 (d, 1H, thienyl), 7.55, 7.63 (2×d, 1H, thienyl); hFSHRago (CHO luc) EC₅₀=138 nM.

Example 26

(8,9-Dimethoxy-1-thiophen-2-yl-5,6-dihydro-imidazo[5,1-a]isoquinolin-3-yl)-[1,4]oxazepan-4-yl-methanone; hydrochloride salt Coupling of the product of example 24a (150 mg) with [1,4]oxazepane hydrochloride (200 mg) was performed according to the method described in example 24c.

Yield: 35 mg. MS-ESI: [M+H]⁺=440.2; NMR (CDCl₃) δ 1.90 (2×m, 4, oxazepam), 3.00 (m, 2, H6), 3.70 (m, 4, oxazepam), 3.80 (m, 2, oxazepam), 3.95 (m, 2, oxazepam), 3.60, 3.80 (2×s, 6, OCH₃), 4.25 (m, 2, H5), 7.01 (s, 1, H7), 7.28 (d, 1, H10, rotamers), 7.12, 7.40, 7.58 (3×m, 3, thiophene); hFSHRago (CHO luc) EC₅₀=314 nM.

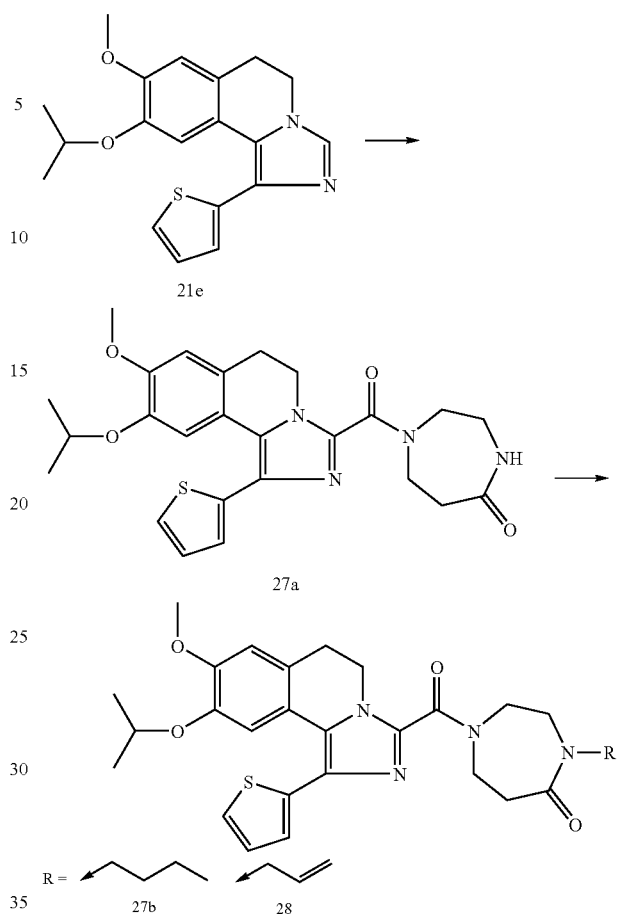

Example 27

4-Butyl-1-(9-isopropoxy-8-methoxy-1-thiophen-2-yl-5,6-dihydro-imidazo[5,1-a]isoquinoline-3-carbonyl)-[1,4]diazepan-5-one; trifluoro-acetic acid salt (a). 1-(9-Isopropoxy-8-methoxy-1-thiophen-2-yl-5,6-dihydro-imidazo[5,1-a]isoquinoline-3-carbonyl)-[1,4]diazepan-5-one To a suspension of the product of example 21e (250 mg) in dry THF (5 ml) was added at −40° C. a n-BuLi solution (482 µl, 1.6 M in heptane). After stirring for 10 min at −40° C., the reaction mixture was poured on CO₂ pellets. The mixture was stirred for 15 min and concentrated in vacuo at 35° C. To a solution of the residue dissolved in DMF (1 ml) and N-ethylmorpholine (252 µl), were added [1,4]diazepan-5-one (335 mg) and TBTU (353 mg). After stirring at room temperature for 2 h, the reaction mixture was poured in an aqueous NH₄Cl solution (5%) and extracted with ethyl acetate. The organic layer was dried (MgSO₄), filtered and concentrated in vacuo. The residue was purified by chromatography on silica gel in dichloromethane/methanol [9:1 (v/v)] as eluent. The fractions with product combined and concentrated in vacuo. The residue was treated with heptane, to provide a white powder and dried in vacuo (50° C.).

Yield: 210 mg. TLC R_f=0.18 (toluene/acetone 1/1). Mp 193-195° C.; NMR CDCl₃) δ 1.27 (m, 6H, isopropyl rotamers), 2.75, 3.42, 3.57 (3×m, 3H, diazepanone), 3.03 (t, 2H, H6), 3.88 (t, 3H, OCH$_3$), 4.25 (m, 2H, CH$_2$), 4.25 (m, 2H, CH$_2$), 4.30 (m, 1H, CH), 4.47 (m, 2H, CH$_2$), 6.15 (m, 1H, NH), 6.78 (s, 1H, H7), 6.78 (s, 1H, H7), 7.08 (m, 1H, thiophene), 7.30 (m, 3H, thiophene+H10).

(b). 4-Butyl-1-(9-isopropoxy-8-methoxy-1-thiophen-2-yl-5,6-dihydro-imidazo[5,1-a]isoquinoline-3-carbonyl)-[1,4]diazepan-5-one; trifluoro-acetic acid salt A mixture of the product of example 27a (70 mg), NaH (15 mg 60% dispersion in oil) and 1-iodo-butane (1 mmol) was stirred at room temperature for 4 h. The reaction mixture was poured in water and extracted with ethyl acetate. The organic layer was washed with water, brine, dried (MgSO$_4$), filtered and concentrated in vacuo. The residue was purified by preparative HPLC (20→100% acetonitrile; with TFA).

Yield: 63 mg. MS-ESI: [M+H]$^+$=537.5; $^1$H-NMR (CDCl$_3$) δ 0.95 (br m, 6, CH3 butyl), 1.30 (br m, 2, CH$_2$-butyl), 1.40 (br m, 2, CH$_2$ butyl), 1.26 (d, 6, isopropyl), 3.03 (t, 2, CH2C6), 4.42 (br m, 2, (C5)CH$_2$), 6.78 (s, 1, H7), 7.23 (br s, 1, H10), 7.28, 7.33, 7.38 (3×m, 3, thiophene); hFSHRago (CHO luc) EC$_{50}$=0.6 nM.

Example 28

4-Allyl-1-(9-isopropoxy-8-methoxy-1-thiophen-2-yl-5,6-dihydro-imidazo[5,1-a]isoquinoline-3-carbonyl)-[1,4]diazepan-5-one; trifluoro-acetic acid salt To a solution of the product of example 27a (144 mg) in 1 ml of DMF (N$_2$) was added NaH (50 mg 60% dispersion in oil). The mixture was heated at 60° C. for 15 min. After cooling to room temperature, the mixture was treated with allyl bromide (35 µl). The mixture was stirred for 1 h. The reaction was poured into water and extracted with ethyl acetate. The organic layer was washed, dried (MgSO$_4$) and concentrated in vacuo. The residue was purified by reverse phase HPLC with water/acetonitrile and 2% TFA as eluent.

Yield: 140 mg, Mp 115-117° C.; MS-ESI: [M+H]$^+$=521.5; $^1$H-NMR (CDCl$_3$) δ 1.28 (m, 6H, isopropoxy, rotamers), 3.88 (s, 3H, OCH$_3$), 3.04 (m, 2H, H6), 4.47 (m, 2H, H5), 5.20 (m, 2H, allyl), 5.78 (m, 1H, allyl), 6.78 (s, 1H, H7), 7.28 (br m, 1H, H10), 7.08 (br m, 1H, thiophene), 7.35 (br m, 2H, thiophene); hFSHRago (CHO luc) EC$_{50}$=3 nM.

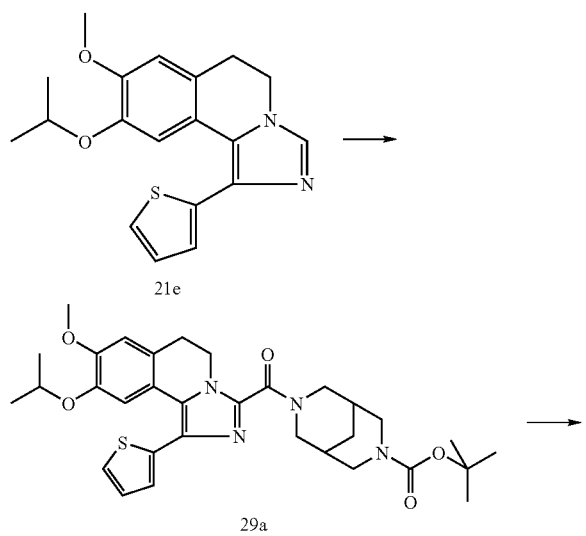

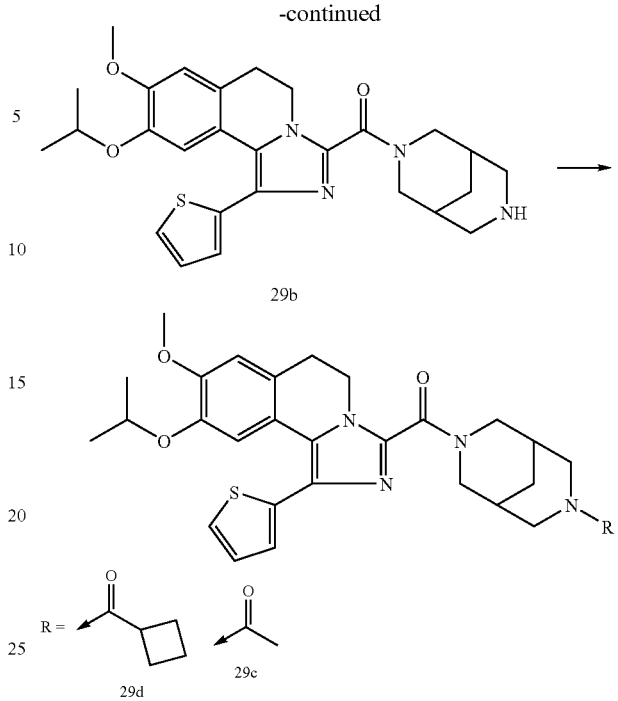

Example 29

1-[7-(9-Isopropoxy-8-methoxy-1-thiophen-2-yl-5,6-dihydro-imidazo[5,1-a]iso-quinoline-3-carbonyl)-3,7-diaza-bicyclo[3.3.1]non-3-yl]-ethanone; trifluoro-acetic acid salt and (7-cyclobutanecarbonyl-3,7-diaza-bicyclo[3.3.1]non-3-yl)-(9-isopropoxy-8-methoxy-1-thiophen-2-yl-5,6-dihydro-imidazo[5,1-a]isoquinolin-3-yl)-methanone; trifluoro-acetic acid salt (a). 7-(9-Isopropoxy-8-methoxy-1-thiophen-2-yl-5,6-dihydro-imidazo[5,1-a]iso-quinoline-3-carbonyl)-3,7-diaza-bicyclo[3.3.1]nonane-3-carboxylic acid tert-butyl ester To a suspension of the product of example 21e (150 mg) in dry THF (5 ml) was added at −40° C. a n-BuLi solution (290 µl, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (2 ml) and N-ethylmorpholine (152 µl), were added 3,7-diaza-bicyclo[3.3.1]nonane-3-carboxylic acid tert-butyl ester (200 mg) [Prepared according to O. Huttenloch, E. Laxman, H. Waldmann, *Chem. Eur. J.*, 8, (20), 4767 (2002)] and TBTU (213 mg). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel in toluene/ethyl acetate [0→100% (v/v)] as eluent.

Yield: 158 mg. LC/MS-ESI: [M+H]$^+$=593.1; TLC R$_f$=0.27 (toluene/ethyl acetate 1:1)

(b). (3,7-Diaza-bicyclo[3.3.1]non-3-yl)-(9-isopropoxy-8-methoxy-1-thiophen-2-yl-5,6-dihydro-imidazo[5,1-a]isoquinolin-3-yl)-methanone; hydrogen chloride salt A mixture of the product of example 29a (158 mg) and a solution of HCl in diethyl ether (3 ml, 2 M) in dichloromethane (10 ml) was stirred at room temperature for 6 h. The reaction mixture was concentrated in vacuo and used as such in the next reaction.

Yield: 146 mg. LC/MS-ESI: [M+H]$^+$=493.1; TLC $R_f$=0.2 (dichloromethane/methanol).

(c). 1-[7-(9-Isopropoxy-8-methoxy-1-thiophen-2-yl-5,6-dihydro-imidazo[5,1-a]iso-quinoline-3-carbonyl)-3,7-diaza-bicyclo[3.3.1]non-3-yl]-ethanone; trifluoro-acetic acid salt A mixture of the product of example 29b (65.5 mg), DIPEA (108 μl) and acetyl chloride (13.3 μl) in dichloromethane was stirred at room temperature for 3 h. The reaction mixture was diluted with water and extracted with dichloromethane. The organic layer was washed with brine, dried (MgSO$_4$), filtered and concentrated in vacuo. The residue was purified by preparative HPLC (20→100% acetonitrile; with 2% TFA).

Yield: 44 mg. MS-ESI: [M+H]$^+$=535.5; NMR (CDCl$_3$) δ 2.22 (s, 3H, CH$_3$CO), 1.23 (d, 6H, isopropoxy), 3.88 (s, 3H, OCH$_3$), 6.75 (s, 1H, H7), 7.10 (s+m, 2H, H10 and thiophene), 7.34 and 7.40 (2×m, 2H, thiophene); hFSHRago (CHO luc) EC$_{50}$=21 nM.

(d). (7-Cyclobutanecarbonyl-3,7-diaza-bicyclo[3.3.1]non-3-yl)-(9-isopropoxy-8-methoxy-1-thiophen-2-yl-5,6-dihydro-imidazo[5,1-a]isoquinolin-3-yl)-methanone; trifluoro-acetic acid salt Coupling of the product of example 29b (65.5 mg) with cyclobutanecarbonyl chloride (21 μl) was performed according to the method described in example 29c.

Yield: 50 mg. MS-ESI: [M+H]$^+$=575.5; $^1$H-NMR (CDCl$_3$) 1.22 (d, 6H, isopropoxy), 3.88 (s, 3H, OCH$_3$), 6.75 (s, 1H, H7), 7.03 (s, 1H, H10), 7.12 (7.38 and 7.45 (3×m, 3H, thiophene); hFSHRago (CHO luc) EC$_{50}$=5 nM.

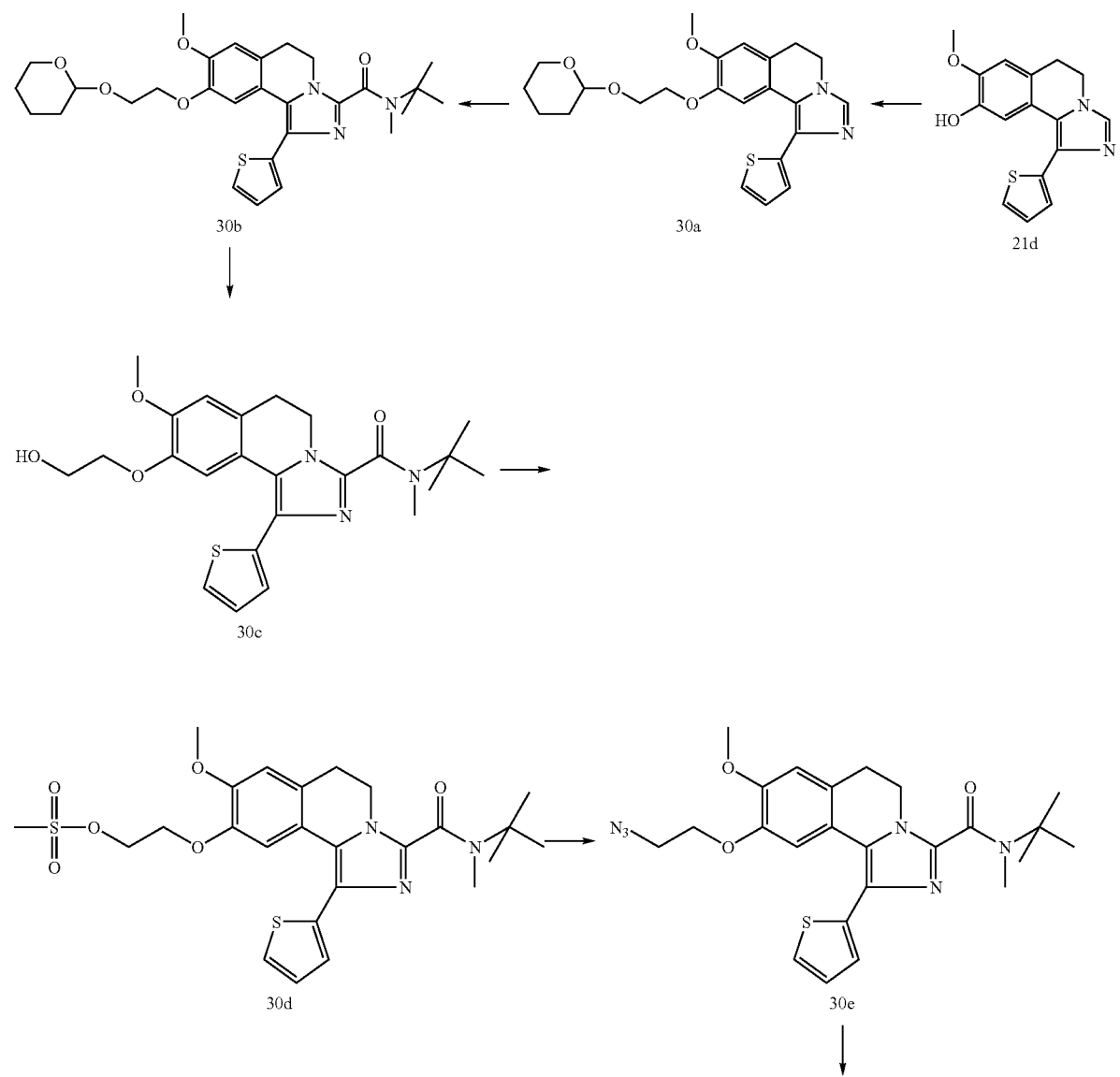

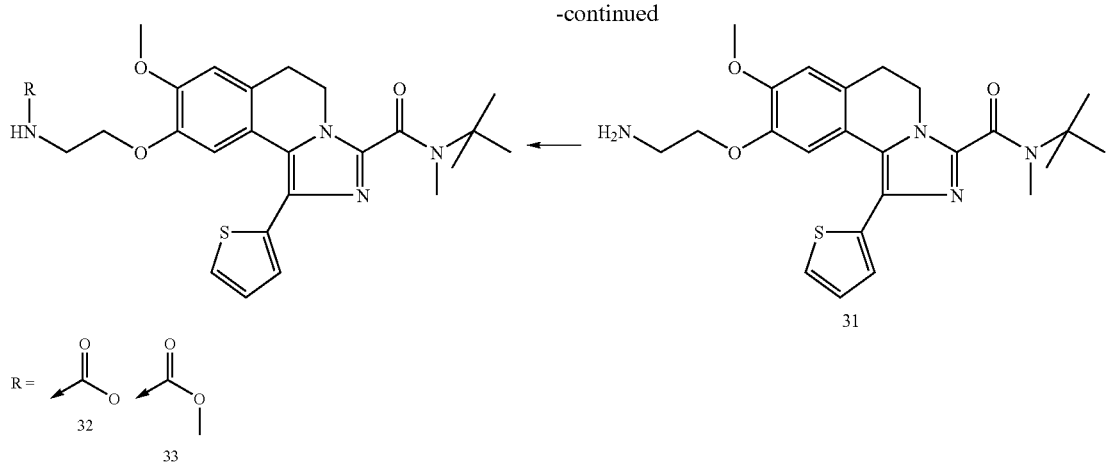

Example 30

9-(2-Azido-ethoxy)-8-methoxy-1-thiophen-2-yl-5,6-dihydro-imidazo[5,1-a]isoquinoline-3-carboxylic acid tert-butyl-methyl-amide; 9-(2-hydroxy-ethoxy)-8-methoxy-1-thiophen-2-yl-5,6-dihydro-imidazo[5,1-a]isoquinoline-3-carboxylic acid tert-butyl-methyl-amide (a). 8-Methoxy-9-[2-(tetrahydro-pyran-2-yloxy)-ethoxy]-1-thiophen-2-yl-5,6-dihydro-imidazo-[5,1-a]isoquinoline A mixture of the product of example 21d (2.1 g), anhydrous $K_2CO_3$ (24.4 g) and 2-(2-bromo-ethoxy)-tetrahydro-pyran (2.1 ml) in DMF (40 ml) was stirred at room temperature for 18 h. The reaction mixture was poured in water and extracted with ethyl acetate. The organic layer was washed twice with water, brine, dried ($MgSO_4$), filtered and concentrated in vacuo. The residue was purified by chromatography on silica gel in dichloromethane/acetone [10/0→3:7 (v/v)] as eluent.

Yield: 2.11 g. LC/MS-ESI: $[M+H]^+$=427.1; TLC $R_f$=0.72 (dichloromethane/acetone 1:1); NMR ($CDCl_3$) δ 6.77 (s, 1H H7), 7.45 (s, 1H, H10), 7.50 (s, 1H, H3), 4.65 (br t, 1H, CH-pyrane), 3.87 (s, 3H, $CH_3O$).

(b). 8-Methoxy-9-[2-(tetrahydro-pyran-2-yloxy)-ethoxy]-1-thiophen-2-yl-5,6-dihydro-imidazo-[5,1-a]isoquinoline-3-carboxylic acid tert-butyl-methyl-amide To a suspension of the product of example 30a (2.11 g) in dry THF (24 ml) was added at −40° C. a n-BuLi solution (3.71 ml, 1.6 M in heptane). After stirring for 10 min at −40° C., the reaction mixture was poured on $CO_2$ pellets. The mixture was stirred for 15 min and concentrated in vacuo at 35° C. To a solution of the residue in DMF (11 ml) and N-ethylmorpholine (1.7 ml), were added N-methyl-tert-butylamine (2.4 ml) and TBTU (2.38 g). After stirring at room temperature for 2 h, the reaction mixture was poured in an aqueous $NH_4Cl$ solution (5%) and extracted with ethyl acetate. The organic layer was dried ($MgSO_4$), filtered and concentrated in vacuo. The residue was purified by chromatography on silica gel in heptane/ethyl acetate [0→50% (v/v)] as eluent.

Yield: 1.33 g. $^1$H-NMR ($CDCl_3$) δ 1.52 (s, 9H, tert-butyl), 3.0 (t, 2H, C(6)$H_2$), 3.22 (s, 3H, $NCH_3$), 3.87 (s, 3H, $OCH_3$), 3.75-3.95 (m, 8H, $CH_2$-pyran), 4.38 (t, 2H, C(5)$H_2$), 4.65 (t, 1H, CH-pyran), 6.75 (s, 1H, ArH7), 7.08, 7.32 (m, 3H, thiophene), 7.28 (s, 1H, ArH10).

(c). 9-(2-Hydroxy-ethoxy)-8-methoxy-1-thiophen-2-yl-5,6-dihydro-imidazo[5,1-a]iso-quinoline-3-carboxylic acid tert-butyl-methyl-amide To a solution of the product of example 30b (1.3 g) in methanol (100 ml) an aqueous HCl solution (3 ml, 6 M) was added. After stirring at room temperature for 2 h, the reaction mixture was added to a saturated aqueous $NaHCO_3$ solution and extracted with ethyl acetate. The organic layer was washed with brine, dried ($MgSO_4$), filtered and concentrated in vacuo.

Yield: 1.1 g. LC/MS-ESI: $[M+H]^+$=456.3; hFSHRago (CHO luc) $EC_{50}$=7 nM.

(d). Methanesulfonic acid 2-[3-(tert-butyl-methyl-carbamoyl)-8-methoxy-1-thiophen-2-yl-5,6-dihydro-imidazo[5,1-a]isoquinolin-9-yloxy]-ethyl ester Methanesulfonyl chloride was added dropwise to a solution of the product of example 30c (1.09 g) and $Et_3N$ (1.0 ml) in dichloromethane (50 ml). After stirring at room temperature for 1 h, the mixture was washed with water, brine, dried ($MgSO_4$), filtered and concentrated in vacuo. The residue was purified by chromatography on silica gel in heptane/ethyl acetate [0→100% (v/v)] as eluent.

Yield: 1.22 g. LC/MS-ESI: $[M+H]^+$=534.2.

(e). 9-(2-Azido-ethoxy)-8-methoxy-1-thiophen-2-yl-5,6-dihydro-imidazo[5,1-a]iso-quinoline-3-carboxylic acid tert-butyl-methyl-amide To a solution of the product of example 30d (500 mg) in DMF (30 ml) was added sodium azide (183 mg). After stirring at 90° C. for 2 h, the reaction mixture was poured in water and extracted with dichloromethane. The organic layer was washed with water, brine, dried ($MgSO_4$), filtered and concentrated in vacuo. The residue was purified by chromatography on silica gel in heptane/ethyl acetate [0→100% (v/v)] as eluent.

Yield: 331 mg. LC/MS-ESI: $[M+H]^+$=481.3; $^1$H-NMR ($CDCl_3$) δ 1.53 (s, 9H, tert-butyl), 3.02 (t, 2H, C(6)$H_2$), 3.25 (s, 3H, $NCH_3$), 3.52 (t, 2H, —$N_3CH_2$), 3.88 (s, 3H, $OCH_3$), 3.93 (t, 2H, —$OCH_2$), 4.4 (t, 2H, C(5)$H_2$), 6.79 (s, 1H, ArH7), 7.2 (s, 1H, ArH10), 7.1, 7.3, 7.36 (m, 3×1H, thiophene); hFSHRago (CHO luc) EC$_{50}$=15 nM.

Example 31

9-(2-Amino-ethoxy)-8-methoxy-1-thiophen-2-yl-5,6-dihydro-imidazo[5,1-a]isoquinoline-3-carboxylic acid tert-butyl-methyl-amide A mixture of the product of example 30e (327 mg), PS—PPh$_3$ (805 mg; loading 1.69 mmol/g resin) and water (2 ml) in dichloromethane/THF (1:1 (v/v); 26 ml) was stirred at 40° C. for 18 h. The reaction mixture was filtered and the filtrate was concentrated in vacuo. The crude product was used as such in the next reaction. A small sample was purified by preparative HPLC (0→100% acetonitrile) and freeze dried from acetonitrile/water.

Yield: 317 mg. LC/MS-ESI: [M+H]$^+$=455.3; $^1$H-NMR (CDCl$_3$) δ 1.53 (s, 9H, tert-butyl), 3.0 (br. s, 2H, NH$_2$), 3.02 (t, 2H, C(6)H$_2$), 3.18 (s, 3H, NCH$_3$), 3.25 (br t, 2H, —OCH$_2$), 3.8 (s, 3H, OCH$_3$), 3.92 (br t, 2H, —NH$_2$CH$_2$), 4.32 (t, 2H, C(5)H$_2$), 6.77 (s, 1H, ArH7), 7.12 (s, 1H, ArH10), 7.05, 7.3, 7.36 (m, 3×1H, thiophene); hFSHRago (CHO luc) EC$_{50}$=94 nM.

Example 32

9-(2-Acetylamino-ethoxy)-8-methoxy-1-thiophen-2-yl-5,6-dihydro-imidazo[5,1-a]isoquinoline-3-carboxylic acid tert-butyl-methyl-amide Acetyl chloride (10.2 µl) was added dropwise to a mixture of the product of example 31 (50 mg) and DIPEA (55 µl) in dichloromethane (2 ml). After stirring at room temperature for 18 h, the reaction mixture was diluted with dichloromethane and washed with water, brine, dried (MgSO$_4$), filtered and concentrated in vacuo. The residue was purified by preparative HPLC (0→100% acetonitrile).

Yield: 34.8 mg. LC/MS-ESI: [M+H]$^+$=497.3; $^1$H-NMR (CDCl$_3$) δ 1.53 (s, 9H, tert-butyl), 2.0 (s, 3H, —C(O)Me), 3.0 (t, 2H, C(6)H$_2$), 3.24 (s, 3H, NCH$_3$), 3.55 (m, 2H, —NCH$_2$), 3.83 (t, 2H, —OCH$_2$), 3.9 (s, 3H, OCH$_3$), 4.4 (t, 2H, C(5)H$_2$), 6.1 (br.s, 1H, —NH), 6.79 (s, 1H, ArH7), 7.3 (s, 1H, ArH10), 7.1, 7.27, 7.35 (m, 3×1H, thiophene); hFSHRago (CHO luc) EC$_{50}$=559 nM.

Example 33

{2-[3-(tert-Butyl-methyl-carbamoyl)-8-methoxy-1-thiophen-2-yl-5,6-dihydro-imidazo[5,1-a]isoquinolin-9-yloxy]-ethyl}-carbamic acid methyl ester Coupling of the product of example 31 (50 mg) with methyl chloroformate (11 µl) was performed according to the method described in example 32.

Yield: 34.3 mg. LC/MS-ESI: [M+H]$^+$=513.3; $^1$H-NMR (CDCl$_3$) δ 1.53 (s, 9H, tert-butyl), 3.0 (t, 2H, C(6)H$_2$), 3.22 (s, 3H, NCH$_3$), 3.5 (t, 2H, —NCH$_2$), 3.7 (s, 3H, —OCH$_3$), 3.83 (t, 2H, —OCH$_2$), 3.87 (s, 3H, OCH$_3$), 4.4 (t, 2H, C(5)H$_2$), 5.48 (br.s, 1H, —NH), 6.79 (s, 1H, ArH7), 7.2 (s, 1H, ArH10), 7.1, 7.3, 7.35 (m, 3×1H, thiophene); hFSHRago (CHO luc) EC$_{50}$=142 nM.

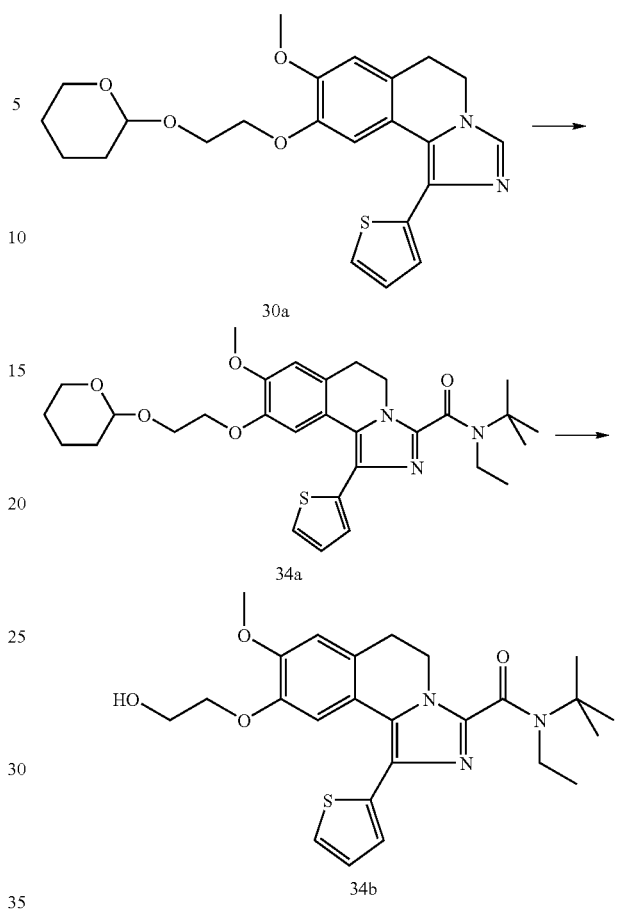

Example 34

9-(2-Hydroxy-ethoxy)-8-methoxy-1-thiophen-2-yl-5,6-dihydro-imidazo[5,1-a]isoquinoline-3-carboxylic acid tert-butyl-ethyl-amide (a). 8-Methoxy-9-[2-(tetrahydro-pyran-2-yloxy)-ethoxy]-1-thiophen-2-yl-5,6-dihydro-imidazo-[5,1-a]isoquinoline-3-carboxylic acid tert-butyl-ethyl-amide To a suspension of the product of example 30a (120 mg) in dry THF (3 ml) was added at −40° C. a n-BuLi solution (0.2 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (2 ml) and N-ethylmorpholine (0.1 ml), were added N-ethyl-tert-butylamine (0.15 ml) and TBTU (170 mg). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel in heptane/ethyl acetate [2:1 (v/v)] as eluent.

Yield: 90 mg. MS-ESI: [M+H]$^+$=554.3; TLC R$_f$=0.35 (toluene/ethyl acetate 7:3); NMR (CDCl3) δ 1.25 (t, 3, ethyl), 1.57 (s, 9, tBu), 3.0 (t, 2, CH$_2$(6)), 3.48, 3.75, 3.95, 4.0 (m, 6H, pyran), 3.82 (q, 2, CH$_2$N), 4.28 (t, 2, CH$_2$(5)), 4.67 (t, 1, CHO(THP)), 3.87 (s, 3, OCH$_3$), 6.76 (s, 1, H7), 7.38 (s, 1, H10).

(b) 9-(2-Hydroxy-ethoxy)-8-methoxy-1-thiophen-2-yl-5,6-dihydro-imidazo[5,1-a]isoquinoline-3-carboxylic acid tert-butyl-ethyl-amide To a solution of the product of example 34a (80 mg) in methanol (1.5 ml) was added p-toluenesulfonic acid (40 mg). The reaction mixture was stirred at room temperature for 2 h. An aqueous NaHCO$_3$ solution was added. The mixture was extracted with ethyl acetate. The organic layer was dried (MgSO$_4$), filtered and concentrated in vacuo. The residue was purified by chromatography on silica gel in heptane/acetone [1:1 (v/v)] as eluent. The fractions with product were combined, concentrated in vacuo. The residue was triturated with diethylether to give a white solid after drying in vacuo (50° C.).

Yield: 35 mg. MS-ESI: [M+H]$^+$=470.3; TLC R$_f$=0.35 (heptane/acetone 1:1); Mp: 178-186° C.; $^1$H-NMR (DMSO-d$_6$) δ 1.2 (t, 3H, —CH$_3$), 1.5 (s, 9H, tert-butyl), 2.98 (t, 2H, C(6)H$_2$), 3.60 (m, 2H, —NCH$_2$—), 3.75 (t, 2H, —OCH$_2$—), 3.8 (s, 3H, OCH$_3$), 4.1 (t, 2H, C(5)H$_2$), 4.84 (t, 1H, OH), 7.0 (s, 1H, ArH7), 7.3 (s, 1H, ArH10), 7.12, 7.38, 7.55 (m, 3×1H, thiophene); hFSHRago (CHO luc) EC$_{50}$=3 nM.

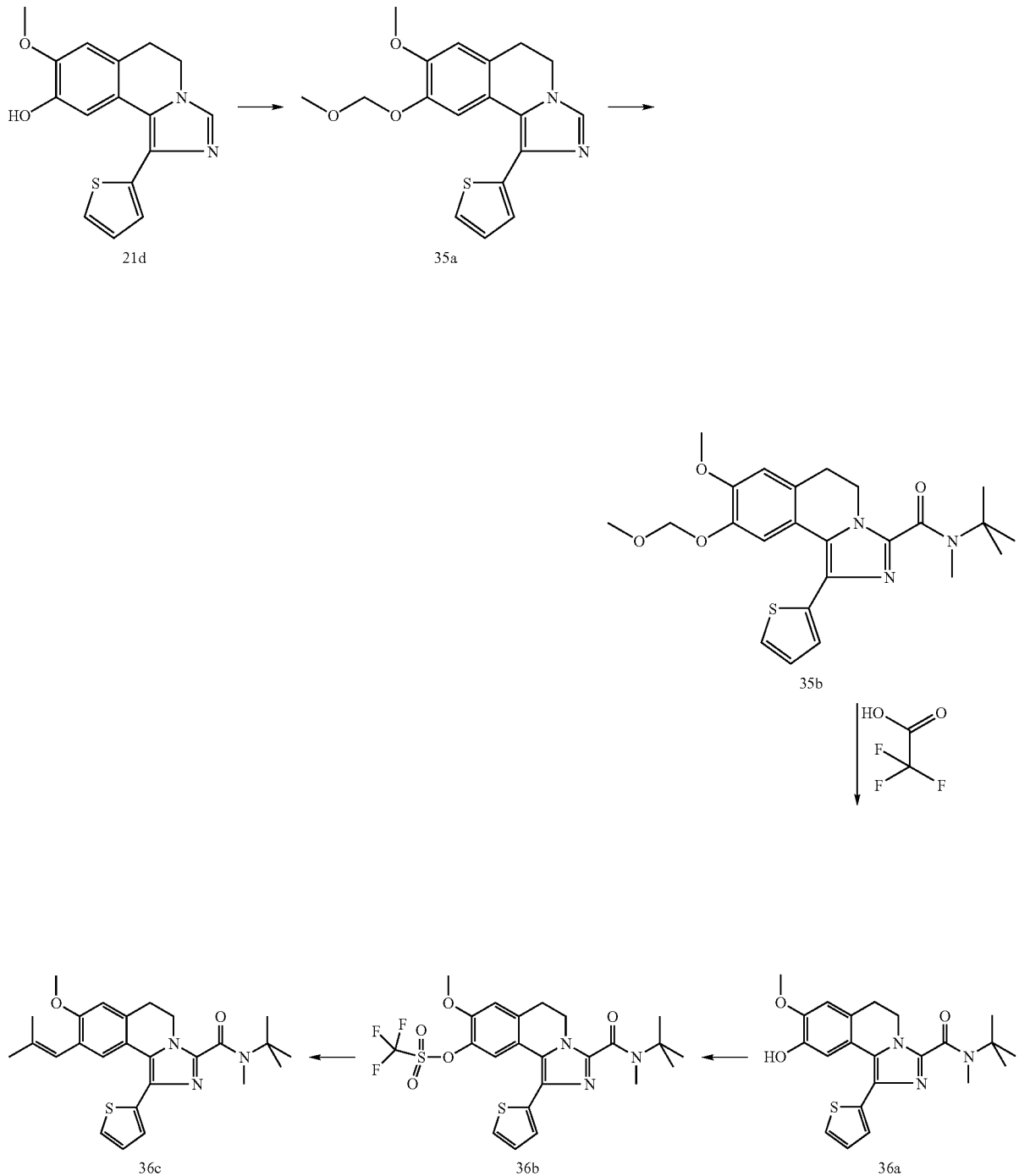

Example 35

8-Methoxy-9-methoxymethoxy-1-thiophen-2-yl-5,6-dihydro-imidazo[5,1-a]isoquinoline-3-carboxylic acid tert-butyl-methyl-amide; trifluoro-acetic acid salt

(a). 8-Methoxy-9-methoxymethoxy-1-thiophen-2-yl-5,6-dihydro-imidazo[5,1-a]isoquinoline To a solution of the product of example 21d (3.3 g) in DMF (25 ml) was added NaH (440 mg 60% dispersion in mineral oil). After stirring for 10 min, MOM-Cl (1 ml) was added at 0° C. The mixture was stirred for an additional 3 h. The product was diluted with water and extracted with ethyl acetate. The organic layer was washed with water, dried (MgSO$_4$), filtered and concentrated in vacuo. The residue was triturated with heptane.

Yield: 2.1 g. NMR (CDCl3) δ 3.42 (s, 3, OCH$_3$), 3.90 (s, 3, OCH$_3$), 5.09 (s, 2, O—CH$_2$—O), 6.78 (s, 1, H7), 7.52 (s, 1, H10), 7.68 (s, 1, H3).

(b). 8-Methoxy-9-methoxymethoxy-1-thiophen-2-yl-5,6-dihydro-imidazo[5,1-a]isoquinoline-3-carboxylic acid tert-butyl-methyl-amide; trifluoro-acetic acid salt To a suspension of the product of example 35a (800 mg) in dry THF (12 ml) was added at −40° C. a n-BuLi solution (1.75 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (5 ml), N-ethylmorpholine (0.8 ml), were added N-methyl-tert-butylamine (1.13 ml) and TBTU (1.13 g). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel in heptane/ethyl acetate [0→80% (v/v)] as eluent.

Yield: 516 mg. MS-ESI: [M+H]$^+$=456.5; $^1$H-NMR (CDCl$_3$) δ 1.52 (s, 9H, tert-butyl), 3.05 (t, 2H, C(6)H$_2$), 3.22 (s, 3H, NCH$_3$), 3.38 (s, 3H, OCH$_3$), 3.9 (s, 3H, OCH$_3$), 4.38 (t, 2H, C(5)H$_2$), 5.02 (s, 2H, —OCH$_2$O—), 6.8 (s, 1H, ArH7), 7.46 (s, 1H, ArH10), 7.1, 7.38 (m, 3×1H, thiophene); hFSHRago (CHO luc) EC$_{50}$=19 nM.

Example 36

8-Methoxy-9-(2-methyl-propenyl)-1-thiophen-2-yl-5,6-dihydro-imidazo[5,1-a]isoquinoline-3-carboxylic acid tert-butyl-methyl-amide; trifluoro-acetic acid salt

(a). 9-Hydroxy-8-methoxy-1-thiophen-2-yl-5,6-dihydro-imidazo[5,1-a]isoquinoline-3-carboxylic acid tert-butyl-methyl-amide An aqueous HCl solution (50 ml 6 M) was added to a solution of the product of example 35b (460 mg) in methanol (50 ml) and 2-propanol (50 ml). After stirring at room temperature for 3 h, water was added. The reaction mixture was washed with a saturated NaHCO$_3$ solution and concentrated in vacuo. The mixture was extracted with ethyl acetate. The organic layer was washed with brine, dried (MgSO$_4$), filtered and concentrated in vacuo. The residue was purified by chromatography on silica gel in heptane/ethyl acetate [0→50% (v/v)] as eluent.

Yield: 293 mg. LC/MS-ESI: [M+H]$^+$=412.1; $^1$H-NMR (CDCl$_3$) δ 1.52 (s, 9H, tert-butyl), 3.0 (t, 2H, C(6)H$_2$), 3.24 (s, 3H, NCH$_3$), 3.9 (s, 3H, OCH$_3$), 4.37 (t, 2H, C(5)H$_2$), 5.5 (s, 1H, OH), 6.75 (s, 1H, ArH7), 7.08 (m, 1H, thiophene), 7.3 (m, 2H, thiophene), 7.31 (s, 1, H10).

(b). Trifluoro-methanesulfonic acid 3-(tert-butyl-methyl-carbamoyl)-8-methoxy-1-thiophen-2-yl-5,6-dihydro-imidazo[5,1-a]isoquinolin-9-yl ester To a solution of the product of example 36a (242 mg) in pyridine (3 ml) at 0° C.) was added trifluoromethane sulfonic anhydride (147 µl) dropwise. After stirring at room temperature for 1 h, the reaction mixture was poured into water and extracted with ethyl acetate. The organic layer was washed with water, brine, dried (MgSO$_4$), filtered and concentrated in vacuo. The remaining residue was co-evaporated twice with toluene.

Yield: 343 mg. LC/MS-ESI: [M+H]$^+$=544.0; $^1$H-NMR (CDCl$_3$) δ 1.52 (s, 9H, tert-butyl), 3.1 (t, 2H, C(6)H$_2$), 3.25 (s, 3H, NCH$_3$), 3.94 (s, 3H, OCH$_3$), 4.42 (t, 2H, C(5)H$_2$), 6.92 (s, 1H, ArH7), 7.08, 7.28, 7.36 (3×m, 3H, thiophene), 7.55 (s, 1H, ArH10).

(c). 8-Methoxy-9-(2-methyl-propenyl)-1-thiophen-2-yl-5,6-dihydro-imidazo[5,1-a]isoquinoline-3-carboxylic acid tert-butyl-methyl-amide; trifluoro-acetic acid salt A mixture of the product of example 36b (80 mg) and example 18a (95 mg) in DME (1 ml) and water (0.3 ml) was degassed by bubbling N$_2$ through the mixture for 5 min. K$_2$CO$_3$ (40 mg) and Pd(PPh$_3$)$_4$ (11 mg) were added. The reaction mixture was heated at 90° C. for 4 h. The reaction mixture was concentrated in vacuo and diluted with water. The aqueous layer was extracted with ethyl acetate. The combined organic layers were washed with brine, dried (MgSO$_4$), filtered and concentrated in vacuo. The residue was purified by preparative HPLC (0→100% acetonitrile; with TFA).

Yield: 52 mg. MS-ESI: [M+H]$^+$=450.3; $^1$H-NMR (CDCl$_3$) δ 1.5 (s, 12H, tert-butyl+CH$_3$), 1.85 (d, 3H, CH$_3$), 3.15 (m, 5H, NCH$_3$+C(6)H$_2$), 3.87 (s, 3H, OCH$_3$), 4.4 (t, 2H, C(5)H$_2$), 6.15 (s, 1H, =CH), 6.75 (s, 1H, ArH7), 7.35 (s, 1H, ArH10), 7.10, 7.35, 7.42 (3×m, 3, thiophene); hFSHRago (CHO luc) EC$_{50}$=2 nM.

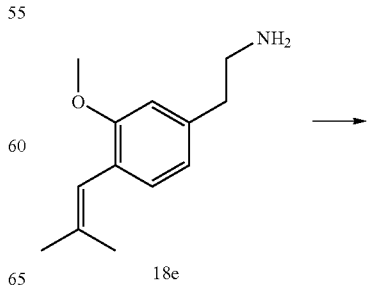

18e

-continued

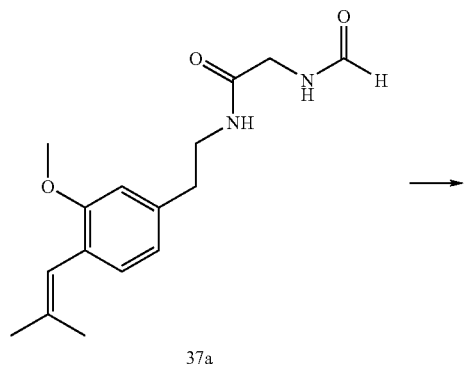

37a

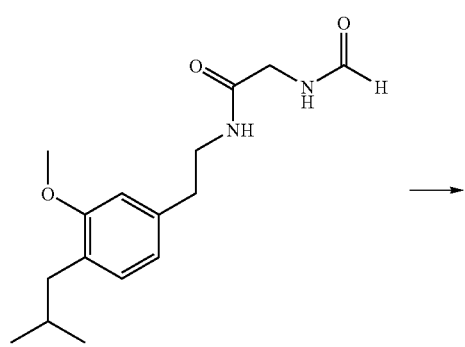

37b

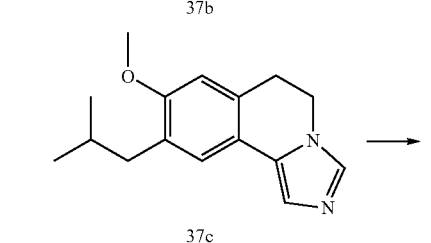

37c

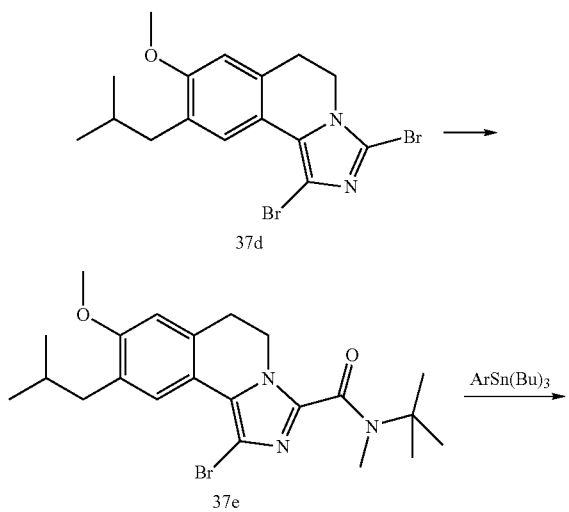

37d

37e

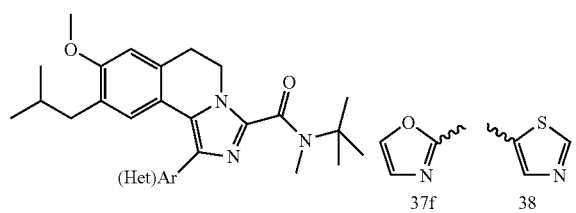

(Het)Ar 37f    38

Example 37

9-Isobutyl-8-methoxy-1-oxazol-2-yl-5,6-dihydro-imidazo[5,1-a]isoquinoline-3-carboxylic acid tert-butyl-methyl-amide (a). 2-Formylamino-N-{2-[3-methoxy-4-(2-methyl-propenyl)-phenyl]-ethyl}-acetamide The product of example 18e (1.5 g) was heated at 90° C. in formylamino-acetic acid ethyl ester (1.3 ml). After 4 h at 90° C., the reaction mixture was concentrated in vacuo. The residue was purified by chromatography on silica gel in dichloromethane/acetone [1:1 (v/v)] as eluent. The fractions with product were combined and concentrated in vacuo. The remaining residue was triturated with heptane to give an off white solid after drying in vacuo (50° C.).

Yield: 0.8 g. MS-ESI: [M+H]$^+$=132.3; TLC R$_f$=0.4 (dichloromethane/acetone 1:1); Mp: 80-81° C.

(b). 2-Formylamino-N-[2-(4-isobutyl-3-methoxy-phenyl)-ethyl]-acetamide

The product of example 37a (700 mg) in ethyl acetate (10 ml) was hydrogenated over Pd/C (10%; 100 mg). After 30 min, the reaction mixture was filtered over Celite and the filtrate was concentrated in vacuo. The residue was triturated with heptane and dried in vacuo (50° C.).

Yield: 610 mg. Mp: 87-90° C.; $^1$H-NMR (DMSO-d$_6$) δ 0.83 (d, 6H, 2×CH$_3$), 1.82 (m, 1H, CH(CH$_3$)$_2$), 2.39 (d, 2H, CH$_2$), 2.68 (t, 2H, CH$_2$), 3.3 (q, 2H, CH$_2$N), 3.7 (d, 2H, —CH$_2$NCHO), 3.77 (s, 3H, OCH$_3$), 6.68 (d, 1, ArH), 6.77 (d, 1, ArH), 6.98 (d, 1, ArH), 8.0 (t, 1, NH), 8.07 (s, 1, CHO), 8.22 (br d, 1, NH).

(c). 9-Isobutyl-8-methoxy-5,6-dihydro-imidazo[5,1-a]isoquinoline

A mixture of methanesulfonic acid (4 ml) and phosphorus pentoxide (500 mg) was heated at 65° C. for 20 min (to become homogeneous). The product of example 37b (600 mg) was added in one portion. After stirring at 65° C. for 1 h, the reaction mixture was poured in ice water and neutralized with solid Na$_2$CO$_3$. The mixture was extracted with ethyl acetate. The organic layer was dried (MgSO$_4$), filtered and concentrated in vacuo. To a solution of the residue in acetonitrile (10 ml) was added POCl$_3$ (2.5 ml). The mixture was stirred at 80° C. for 45 min, poured in ice water and neutralized with solid Na$_2$CO$_3$. The mixture was extracted with ethyl acetate. The residue was purified by chromatography on silica gel in dichloromethane/acetone [1:1 (v/v)] as eluent.

Yield: 200 mg. TLC R$_f$=0.45 (dichloromethane/acetone 1:1); Mp: 92-95° C.; $^1$H-NMR (DMSO-d$_6$) δ 0.85 (d, 6H, 2×CH$_3$), 1.88 (m, 1H, CH(CH$_3$)$_2$), 2.42 (d, 2H, —CH$_2$CH(CH$_3$)$_2$), 3.0 (t, 2H, C(6)H$_2$), 3.78 (s, 3H, OCH$_3$), 4.13 (t, 2H, C(5)H$_2$), 6.92, 7.21, 7.32, 7.63 (4×s, 4, ArH).

(d). 1,3-Dibromo-9-isobutyl-8-methoxy-5,6-dihydro-imidazo[5,1-a]isoquinoline

A solution of Br$_2$ (90 μl) in acetic acid (2 ml) was added to a mixture of the product of example 37c (200 mg) and sodium acetate (700 mg) in acetic acid (4 ml) The last part of this solution was added in a controlled way to the equivalence point (followed by mass spetrometry+TLC). The reaction mixture was diluted with water. Some Na$_2$S$_2$O$_3$ was added to neutralize the small excess of Br$_2$. The mixture was extracted with ethyl acetate. The organic layer was washed with water, (MgSO$_4$), filtered and concentrated in vacuo. The residue was purified by chromatography on silica gel (heptane/ethyl acetate as eluent).

Yield: 210 mg. MS-ESI: [M+H]$^+$=413.1/145.3/417.1; TLC R$_f$=0.6 (heptane/ethyl acetate 1:1); Mp: 99-101° C.; $^1$H-NMR (CDCl$_3$) δ 0.92 (d, 6H, 2×CH$_3$), 1.93 (m, 1H, CH(CH$_3$)$_2$), 2.52 (d, 2H, —CH$_2$CH(CH$_3$)$_2$), 3.05 (t, 2H, C(6) H$_2$), 3.82 (s, 3H, OCH$_3$), 4.13 (t, 2H, C(5)H$_2$), 6.71 (s, 1H, ArH7), 7.91 (s, 1H, ArH10).

(e). 1-Bromo-9-isobutyl-8-methoxy-5,6-dihydro-imidazo[5,1-a]isoquinoline-3-carboxylic acid tert-butyl-methyl-amide To a suspension of the product of example 37d (210 mg) in dry THF (3 ml) was added at −40° C. a n-Buli solution (0.35 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (3 ml) and N-ethylmorpholine (0.12 ml), were added N-methyl-tert-butylamine (0.15 ml) and TBTU (0.25 g). After stirring at room temperature for 2 h, the reaction mixture was poured in an aqueous NH$_4$Cl solution (5%). The mixture was extracted with ethyl acetate. The organic layer was dried (MgSO$_4$), filtered and concentrated in vacuo. The residue was purified by chromatography on silica gel in toluene/ethyl acetate [3:1 (v/v)] as eluent. The fractions with product were combined and concentrated in vacuo. The residue was triturated with cold heptane.

Yield: 120 mg. MS-ESI: [M+H]$^+$=448.3/450.3; TLC R$_f$=0.44 (toluene/ethyl acetate 3:1); Mp: 160-161° C.; $^1$H-NMR (CDCl$_3$) δ 0.92 (d, 6H, 2×CH$_3$), 1.5 (s, 6H, tert-butyl), 1.95 (m, 1H, —CH(CH$_3$)$_2$), 2.52 (d, 2H, CH$_2$), 3.03 (t, 2H, C(6)H$_2$), 3.2 (s, 3H, NCH$_3$), 3.83 (s, 3H, OCH$_3$), 4.38 (t, 2H, C(5)H$_2$), 6.72 (s, 1H, ArH7), 7.98 (s, 1H, ArH10).

(f). 9-Isobutyl-8-methoxy-1-oxazol-2-yl-5,6-dihydro-imidazo[5,1-a]isoquinoline-3-carboxylic acid tert-butyl-methyl-amide A mixture of the product of example 37e (40 mg), 2-(tributylstannyl)oxazole (150 mg) and Pd(PPh$_3$)$_4$ (20 mg) in degassed toluene (2 ml) was stirred at 110° C. for 4 h. The reaction mixture was concentrated in vacuo. The residue was purified by chromatography on silica gel in toluene/ethyl acetate [3:1 (v/v)] as eluent. The fractions with product were combined, concentrated in vacuo. The residue was triturated with heptane to give an of white solid after drying in vacuo (50° C.).

Yield: 35 mg. MS-ESI: [M+H]$^+$=437.5; TLC R$_f$=0.25 (toluene/ethyl acetate 3:1); Mp: 147-148° C.; $^1$H-NMR (DMSO-d$_6$) δ 0.9 (d, 6H, 2×CH$_3$), 1.48 (s, 9H, tert-butyl), 1.9 (m, 1H, —CH), 3.05 (s+t, 3H, —NCH$_3$+C(6)H$_2$), 3.83 (s, 3H, OCH$_3$), 4.2 (t, 2H, C(5)H$_2$), 7.0 (s, 1, H7), 7.37 (s, 1, H10), 8.15 (s, 1, H-oxazole), 8.6 (s, 1, H-oxazole); hFSHRago (CHO luc) EC$_{50}$=380 nM.

Example 38

9-Isobutyl-8-methoxy-1-thiazol-5-yl-5,6-dihydro-imidazo[5,1-a]isoquinoline-3-carboxylic acid tert-butyl-methyl-amide Coupling of the product of example 37e (50 mg) with 5-(tributylstannyl)thiazole (150 mg) was performed according to the method described in example 37f.

Yield: 35 mg. MS-ESI: [M+H]$^+$=453.5; TLC R$_f$=0.3 (toluene/ethyl acetate 3:1); Mp: 144-145° C.; $^1$H-NMR (DMSO-d$_6$) δ 0.8 (d, 6H, 2×CH$_3$), 1.5 (s, 9H, tert-butyl), 1.78 (m, 1H, —CH), 2.30 (d, 2, CH2Ar), 3.05 (t and s, 3H, C(6)H$_2$+N—CH$_3$), 3.83 (s, 3H, OCH$_3$), 4.17 (t, 2H, C(5)H$_2$), 7.0 (s 1, H7), 7.32 (s, 1, H10), 8.05 and 9.1 (2×s, 2, H-thiazole); hFSHRago (CHO luc) EC$_{50}$=13 nM.

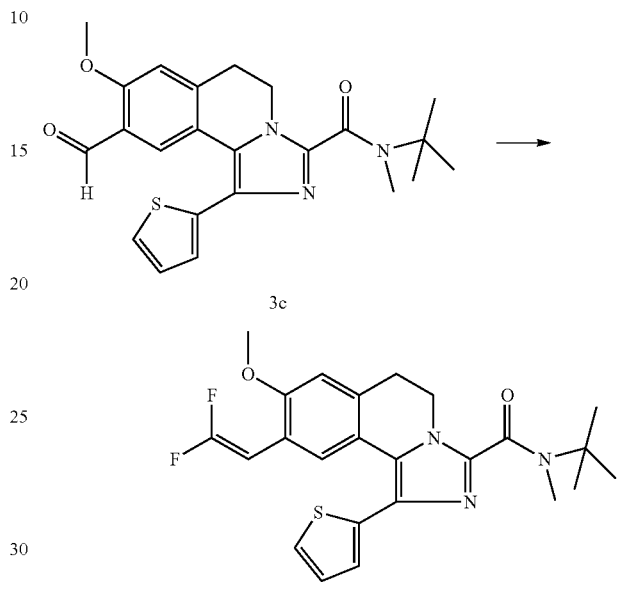

Example 39

9-(2,2-Difluoro-vinyl)-8-methoxy-1-thiophen-2-yl-5,6-dihydro-imidazo[5,1-a]isoquinoline-3-carboxylic acid tert-butyl-methyl-amide To a solution of diisopropylamine (60 µl) in freshly distilled THF (3 ml) at −40° C. was added drop wise N-BuLi (240 µl, 1.6 M in hexane). The mixture was stirred for 10 min at −60° C. A solution of (difluoromethyl)diphenylphosphinoxide (90 mg) in THF (1 ml) was added. The mixture was stirred for an additional 15 min at −40° C. A solution of the product of example 3c (130 mg) in THF (1 ml) was added and the reaction mixture was stirred at 70° C. for 1.5 h. At room temperature, an aqueous NH$_4$Cl solution (5%) was added. The mixture was extracted with ethyl acetate. The organic layer was dried (MgSO$_4$), filtered and concentrated in vacuo. The residue was purified by chromatography on silica gel in toluene/ethyl acetate [3:1 (v/v)] as eluent. The fractions with product were combined, concentrated in vacuo. The remaining residue was triturated with cold heptane to give a white solid after drying in vacuo (50° C.).

Yield: 65 mg. LC/MS-ESI: [M+H]$^+$=458.3; TLC R$_f$=0.62 (toluene/ethyl acetate 1:1); Mp: 154-155° C.; $^1$H-NMR (CDCl$_3$) δ 1.53 (s, 9H, tert-butyl), 3.06 (t, 2H, C(6)H$_2$), 3.25 (s, 3H, NCH$_3$), 3.86 (s, 3H, OCH$_3$), 4.4 (t, 2H, C(5)H$_2$), 5.55 (dd, 1H, —CH═CF2), 6.77 (s, 1H, ArH7), 7.82 (s, 1H, ArH10), 7.07, 7.30, 7.34 (3×m, 3, thiophene); hFSHRago (CHO luc) EC$_{50}$=22 nM.

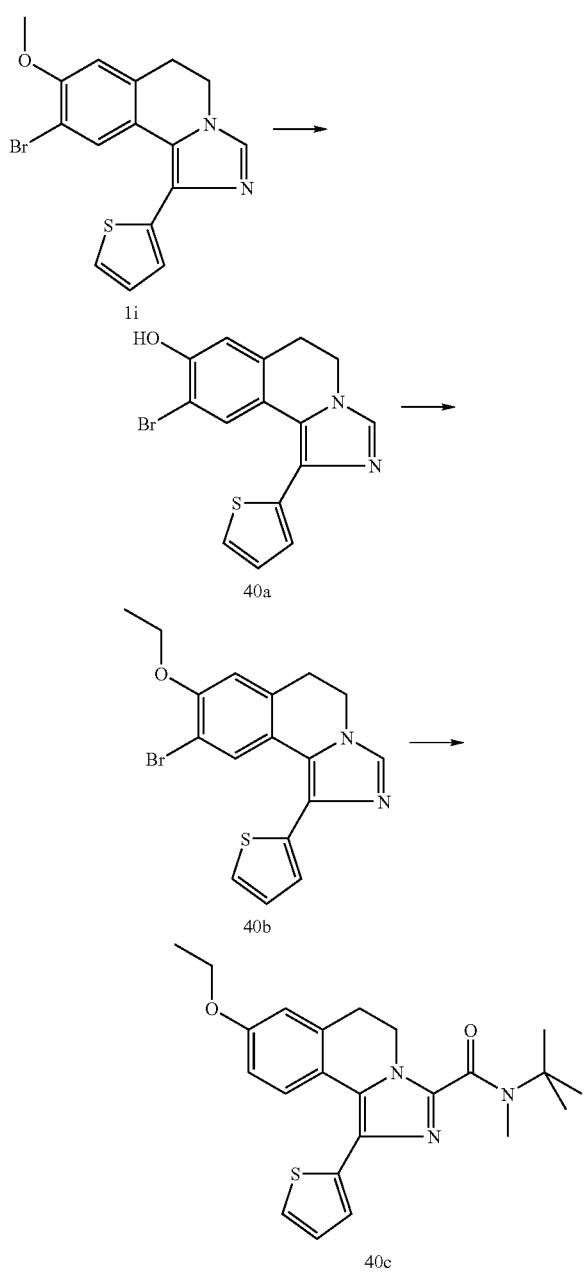

Example 40

8-Ethoxy-1-thiophen-2-yl-5,6-dihydro-imidazo[5,1-a]isoquinoline-3-carboxylic acid tert-butyl-methyl-amide (a). 9-Bromo-1-thiophen-2-yl-5,6-dihydro-imidazo[5,1-a]isoquinolin-8-ol Boron tribromide (2.0 ml) was added drop wise to a cooled solution (−60° C.) of the product of example 1i (1.2 g) in dichloromethane (40 ml). The reaction mixture was transferred to cold methanol (−50° C.; 60 ml). The mixture was warmed to room temperature and concentrated in vacuo. Water (40 ml) was added. The mixture was neutralized with a saturated NaHCO$_3$ solution and stirred for 30 min. The solids were collected by filtration and dried in vacuo (50° C.).

Yield: 1.15 g. MS-ESI: [M+H]$^+$=347.0/349.0; TLC R$_f$=0.10 (toluene/ethyl acetate 1:1)

(b). 9-Bromo-8-ethoxy-1-thiophen-2-yl-5,6-dihydro-imidazo[5,1-a]isoquinoline

A mixture of the product of example 40a (1.45 g), sodium hydride (60% dispersion in oil; 250 mg), ethyl iodide (0.5 ml) in DMF (10 ml) was stirred at 55° C. for 1 h. At room temperature, water and a saturated NH$_4$Cl solution was added. The mixture was extracted with ethyl acetate. The organic layer was washed with water, dried (MgSO$_4$), filtered and concentrated in vacuo. The residue was treated with heptane/diisopropylether. The solids were collected by filtration and dried in vacuo (50° C.).

Yield: 1.3 g. MS-ESI: [M+H]$^+$=375.1/377.0; TLC R$_f$=0.55 (toluene/acetone 1:1); Mp: 159-160° C.; $^1$H-NMR (DMSO-d$_6$) δ 1.38 (t, 3H, CH$_3$), 3.02 (t, 2H, C(6)H$_2$), 4.15 (m, 5H, C(5)H$_2$+OCH$_2$—), 7.12, 7.28 and 7.55 (3×m, 3H, thiophene), 7.28 (s, 1, H7), 7.78 (s, 1, H10), 7.86 (s, 1, H3)

(c). 8-Ethoxy-1-thiophen-2-yl-5,6-dihydro-imidazo[5,1-a]isoquinoline-3-carboxylic acid tert-butyl-methyl-amide To a solution of the product of example 40b (360 mg) in dry THF (6 ml) was added at −60° C. a solution of phenyllithium (500 μl 20% w/w in dibutyl ether). After stirring at −60° C. for 10 min, the reaction mixture was poured on CO$_2$ pellets. The reaction mixture was stirred at room temperature under N$_2$ for 10 min. The reaction mixture was concentrated in vacuo. To a solution of the residue in dry DMF (5 ml) N-methyl-tert-butylamine (300 μl), were added N-ethylmorpholine (300 μl), 1-hydroxybenzotriazole (40 mg) and TBTU (500 mg). The reaction mixture was stirred at room temperature for 2 h. The mixture was poured in an aqueous NH$_4$Cl solution and extracted twice with ethyl acetate. The combined organic layers were washed with water, brine, dried (Na$_2$SO$_4$), filtered and concentrated in vacuo. The residue was purified by chromatography on silica gel in heptane/ethyl acetate [1:1 (v/v)] as eluent.

Yield: 15 mg. MS-ESI: [M+H]$^+$=410.3; TLC R$_f$=0.58 (heptane/ethyl acetate 1;1); Mp: 111-112° C.; $^1$H-NMR (CDCl$_3$) δ 1.4 (t, 3H, —CH$_3$), 1.52 (s, 9H, tert-butyl), 3.04 (t, 2H, C(6)H$_2$), 3.25 (s, 3H, NCH$_3$), 4.05 (q, 2H, —OCH$_2$), 4.38 (t, 2H, C(5)H$_2$), 6.70 (dd, 1, H9), 6.79 (d, 1, H7), 7.64 (d, 1, H10), 7.07, 7.29 and 7.33 (3×m, 3, thiophene); hFSHRago (CHO luc) EC$_{50}$=417 nM.

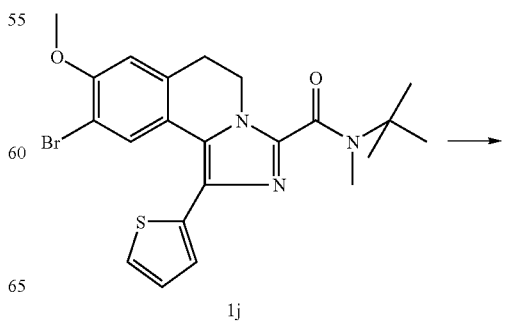

1j

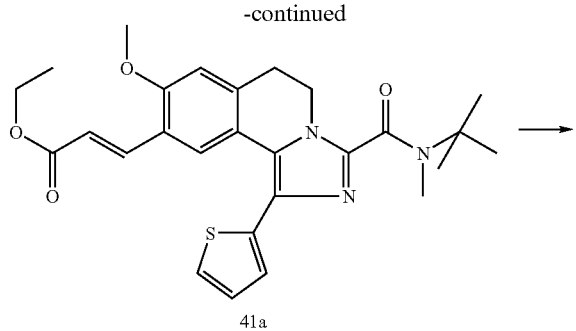

41a

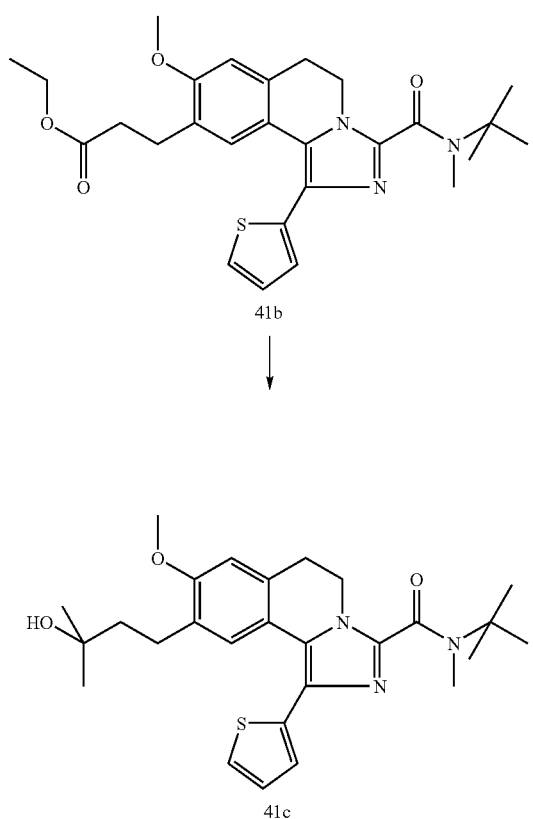

41b

↓

41c

Example 41

9-(3-Hydroxy-3-methyl-butyl)-8-methoxy-1-thiophen-2-yl-5,6-dihydro-imidazo[5,1-a]isoquinoline-3-carboxylic acid tert-butyl-methyl-amide (a). (E)-3-[3-(tert-Butyl-methyl-carbamoyl)-8-methoxy-1-thiophen-2-yl-5,6-dihydro-imidazo[5,1-a]isoquinolin-9-yl]-acrylic acid ethyl ester A mixture of the product of example 1j (145 mg), (E)-3-tributylstannanylacrylic acid ethyl ester (230 μl) and Pd(PPh$_3$)$_4$ (80 mg) in degassed toluene (3 ml) was stirred and heated in the microwave at 140° C. for 1 h. The reaction mixture was diluted with ethyl acetate and an aqueous 5% NH$_4$Cl solution. The resulting mixture was passed through Celite. The organic layer was washed with brine, dried (MgSO$_4$), filtered and concentrated in vacuo. The residue was purified by chromatography on silica gel (toluene/ethyl acetate as eluent). The fractions with product were combined, concentrated in vacuo. The remaining residue was triturated with heptane to give a white solid after drying in vacuo (50° C.).

Yield: 70 mg. LC/MS-ESI: [M+H]$^+$=494.2; TLC R$_f$=0.66 (toluene/ethyl acetate 1:1); Mp: 125-129° C.; $^1$H-NMR (CDCl$_3$) δ 1.33 (t, 3H, —OCH$_2$CH$_3$), 1.52 (s, 9H, tert-butyl), 3.08 (t, 2H, C(6)H$_2$), 3.25 (s, 3H, NCH$_3$), 3.91 (s, 3H, OCH$_3$), 4.22 (q, 2H, —OCH$_2$), 4.4 (t, 2H, C(5)H$_2$), 6.22 (d, 1H, CH=CH), 6.82 (s, 1H, ArH7), 7.1, 7.32, 7.38 (m, 3H, thiophene), 7.89 (s, 1H, ArH10), 7.82 (d, 1H, CH=CH).

(b). 3-[3-(tert-Butyl-methyl-carbamoyl)-8-methoxy-1-thiophen-2-yl-5,6-dihydro-imidazo[5,1-a]isoquinolin-9-yl]-propionic acid ethyl ester A mixture of the product of example 41a (400 mg) in ethyl acetate (20 ml) and ethanol (10 ml) was hydrogenated over Pd/C (10%; 500 mg) in a Parr apparatus under pressure (30 psi). After 72 h, the reaction mixture was filtered over Celite. The filtrate was concentrated in vacuo. The residue was purified by chromatography on silica gel in toluene/ethyl acetate [1:1 (v/v)] as eluent. The fractions with product were combined and concentrated in vacuo. The remaining residue was triturated with heptane/diisopropylether to give a white solid after drying in vacuo (50° C.).

Yield: 170 mg. LC/MS-ESI: [M+H]$^+$=496.2; TLC R$_f$=0.60 (toluene/ethyl acetate 1:1); Mp: 78-80° C.; $^1$H-NMR (CDCl$_3$) δ 1.22 (t, 3H, —OCH$_2$CH$_3$), 1.52 (s, 9H, tert-butyl), 2.5, 2.8 (2×t, 4H, CH$_2$—CH$_2$), 3.05 (t, 2H, C(6)H$_2$), 3.25 (s, 3H, NCH$_3$), 3.85 (s, 3H, OCH$_3$), 4.10 (q, 2H, OCH$_2$), 4.38 (t, 2H, C(5)H$_2$), 6.72 (s, 1H, ArH7), 7.08 (m 1H, thiophene), 7.32, (m, 2H, thiophene), 7.52 (s, 1H, ArH10).

(c). 9-(3-Hydroxy-3-methyl-butyl)-8-methoxy-1-thiophen-2-yl-5,6-dihydro-imidazo[5,1-a]isoquinoline-3-carboxylic acid tert-butyl-methyl-amide To a solution of the product of example 41b (110 mg) in dry THF (4 ml) was added a solution of methyl magnesium chloride in THF (200 μl 3M). Progress of the reaction was monitored by TLC. After stirring at room temperature for 1 h, the reaction mixture was poured in a saturated NH$_4$Cl solution and extracted with ethyl acetate. The organic layer was washed with brine, dried (MgSO$_4$), filtered and concentrated in vacuo. The residue was purified by chromatography on silica gel in toluene/ethyl acetate [1:1 (v/v)] as eluent. The fractions with product were combined and concentrated in vacuo. The remaining residue was triturated with diethyl ether/diisopropyl ether [1:3 (v/v)] to give a white solid.

Yield: 45 mg. MS-ESI: [M+H]$^+$=482.5; TLC R$_f$=0.40 (toluene/ethyl acetate 1:1); Mp: 140-143° C.; $^1$H-NMR (CDCl$_3$) δ 1.22 (s, 6H, CH$_3$), 1.52 (s, 9H, tBu), 1.63 (m, 2H, —CH$_2$), 2.58 (m, 2H, CH$_2$), 3.05 (t, 2H, C(6)H$_2$), 3.25 (s, 3H, NCH$_3$), 3.85 (s, 3H, OCH$_3$), 4.4 (t, 2H, C(5)H$_2$), 6.72 (s, 1H, ArH7), 7.5 (s, 1H, ArH10), 7.07 (m, 1H, thiophene), 7.32 (m, 2H, thiophene); hFSHRago (CHO luc) EC$_{50}$=191 nM.

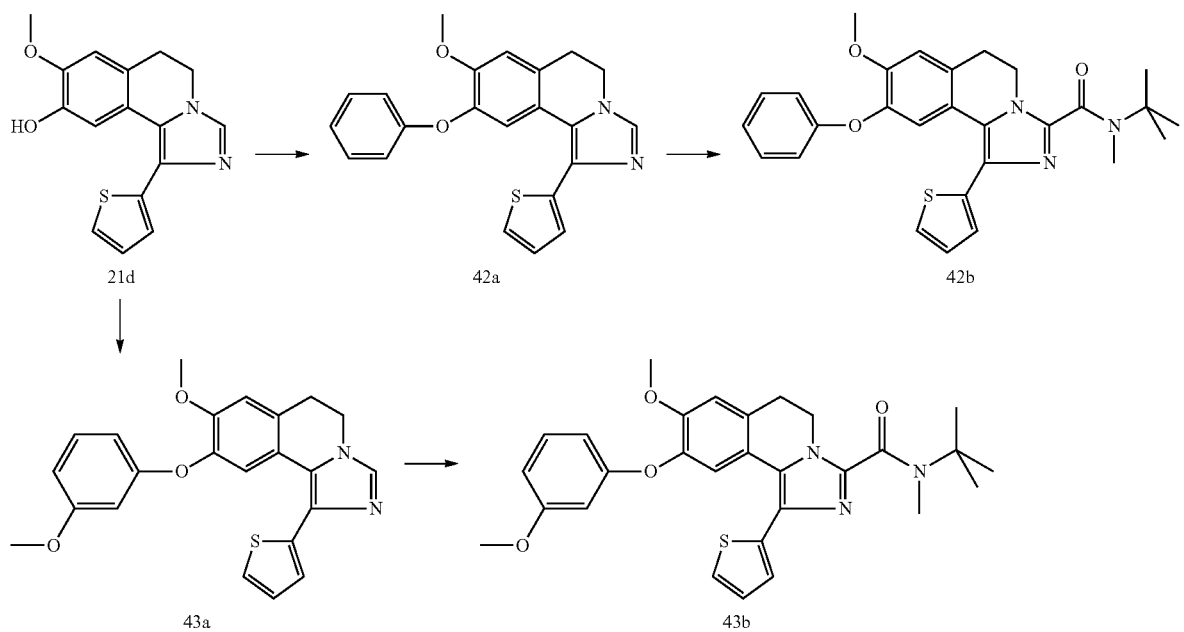

Example 42

8-Methoxy-9-phenoxy-1-thiophen-2-yl-5,6-dihydro-imidazo[5,1-a]isoquinoline-3-carboxylic acid tert-butyl-methyl-amide (a). 8-Methoxy-9-phenoxy-1-thiophen-2-yl-5,6-dihydro-imidazo[5,1-a]isoquinoline A mixture of the product of example 21d (250 mg), phenylboronic acid (190 mg), Cu(OAc)$_2$ (150 mg), pyridine (400 µl) and mol sieves (3.5 g 4A) in dichloromethane (10 ml) was stirred at room temperature for 48 h. The reaction mixture was filtered over Celite. The filtrate was diluted with a saturated NaHCO$_3$ solution, a saturated NH$_4$Cl solution and ethyl acetate. This mixture was shaken vigorously and filtered over Celite. The filtrate was extracted with ethyl acetate. The organic layer was dried (MgSO$_4$), filtered and concentrated in vacuo. The residue was purified by chromatography on silica gel (dichloromethane/acetone as eluent).

Yield: 190 mg. MS-ESI: [M+H]$^+$=375.3; TLC R$_f$=0.66 (dichloromethane/acetone 1:1); $^1$H-NMR (DMSO-d$_6$) δ 3.08 (t, 2H, C(6)H$_2$), 3.78 (s, 3H, OCH$_3$), 4.16 (t, 2H, C(5)H$_2$), 6.88-8.03 (m, 11H, ArH).

(b). 8-Methoxy-9-phenoxy-1-thiophen-2-yl-5,6-dihydro-imidazo[5,1-a]isoquinoline-3-carboxylic acid tert-butyl-methyl-amide To a solution of the product of example 42a (190 mg) in dry THF (2 ml) was added at −40° C. n-BuLi (0.35 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (3 ml) and N-ethylmorpholine (0.15 ml), were added N-methyl-tert-butylamine (0.1 ml) and TBTU (0.2 g). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel (toluene/ethyl acetate) as eluent. The fractions with product were combined and concentrated in vacuo. The residue was triturated with diisopropylether.

Yield: 125 mg. MS-ESI: [M+H]$^+$=488.3; TLC R$_f$=0.65 (toluene/ethyl acetate 1:1); Mp: 122-126° C.; $^1$H-NMR (DMSO-d$_6$) δ 1.48 (s, 9H, tert-butyl), 3.02 (s, 3H, NCH), 3.08 (t, 2H, C(6)H$_2$), 3.8 (s, 3H, OCH$_3$), 4.2 (t, 2H, C(5)H$_2$), 6.87 (d, 2, ArH), 7.05 (t, 1, ArH), 7.31 (t, 2, ArH), 6.91, 7.12 and 7.43 (3×m, 3, thiophene), 7.22 (s, 1, H7), 7.26 (s, 1, H10); hFSHRago (CHO luc) EC$_{50}$=128 nM.

Example 43

8-Methoxy-9-(3-methoxy-phenoxy)-1-thiophen-2-yl-5,6-dihydro-imidazo[5,1-a]isoquinoline-3-carboxylic acid tert-butyl-methyl-amide (a). 8-Methoxy-9-(3-methoxy-phenoxy)-1-thiophen-2-yl-5,6-dihydro-imidazo[5,1-a]isoquinoline Coupling of the product of example 21d (144 mg) with 3-methoxyphenylboronic acid (100 µl) was performed according to the method described in example 42a.

Yield: 110 mg. MS-ESI: [M+H]$^+$=405.1; TLC R$_f$=0.66 (dichloromethane/acetone 1:1); Mp: 147-150° C.; $^1$H-NMR (DMSO-d$_6$) δ 3.05 (t, 2H, C(6)H$_2$), 3.7, 3.8 (2×s, 6H, 2×OCH$_3$), 4.15 (t, 2H, C(5)H$_2$), 6.41 (m, 1, ArH), 6.48 (m, 1, ArH), 6.63 (m, 1, ArH), 6.88, 7.08 and 7.38 (3×m, 3, thiophene) 7.21 (m and s, 2, ArH+H7), 7.18 (s, 1, H10), 7.77 (s, 1, H-imidazo).

(b). 8-Methoxy-9-(3-methoxy-phenoxy)-1-thiophen-2-yl-5,6-dihydro-imidazo[5,1-a]isoquinoline-3-carboxylic acid tert-butyl-methyl-amide To a solution of the product of example 43a (100 mg) in dry THF (2 ml) was added at −40° C. n-BuLi (0.17 ml, 1.6 M in heptane). After stirring for 10 min at −40° C., the reaction mixture was poured on CO$_2$ pellets. The mixture was stirred for 15 min and concentrated in vacuo at 35° C. To a solution of the residue dissolved in DMF (2 ml) and N-ethylmorpholine (60 µl), were added N-methyl-tert-butylamine (0.1 ml) and TBTU (0.13 g). After stirring at room temperature for 2 h, the reaction mixture was poured in an aqueous $NH_4Cl$ solution (5%) and extracted with ethyl acetate. The organic layer was dried ($MgSO_4$), filtered and concentrated in vacuo. The residue was purified by chromatography on silica gel (toluene/ethyl acetate as eluent). The fractions with product combined, concentrated in vacuo and the residue was triturated with diisopropylether.

Yield: 45 mg. MS-ESI: $[M+H]^+$=518.5; TLC $R_f$=0.25 (heptane/ethyl acetate 1:1); Mp: 123-124° C.; $^1$H-NMR (DMSO-$d_6$) δ 1.46 (s, 9H, tert-butyl), 3.02 (s, 3H, $NCH_3$), 3.05 (t, 2H, C(6)$H_2$), 3.7, 3.8 (2×s, 6H, 2×$OCH_3$), 4.2 (t, 2H, C(5)$H_2$), 6.40, 6.47, 6.64, and 7.20 (4×m, 4, ArH), 7.92, 7.13, and 7.43 93×m, 3, thiophene), 7.22 and 7.27 (2×s, H7 and H10); hFSHRago (CHO luc) $EC_{50}$=447 nM.

L-tert-leucine (5 g) in formic acid (50 ml). The reaction mixture was stirred at 0° C. for 1 h and at room temperature for 3 h. Water (25 ml) was added. The mixture was stirred for another 30 min, concentrated in vacuo and co-evaporated twice with toluene. The remaining residue was triturated with diethyl ether. The solids were collected and dried in vacuo (50° C.).

Yield: 5.8 g. Mp: 217-219° C.; $^1$H-NMR (DMSO-$d_6$) δ 0.95 (s, 9H, tert-butyl), 4.12 (d, 1H, CH), 8.05 (s, 1H, CHO), 8.35 (d, 1H, NH), 12.7 (br.s, 1H, COOH).

(b). (S)—N-[2-(4-Bromo-3-methoxy-phenyl)-ethyl]-2-formylamino-3,3-dimethyl-butyramide A mixture of the product of example 1e (4 g), the product of example 44a (3.11 g), DIPEA (7.84 ml) and TBTU (6.26 g) in NMP (75 ml) was stirred at room temperature for 2 h. The reaction mixture was poured in a saturated $NH_4Cl$ solution

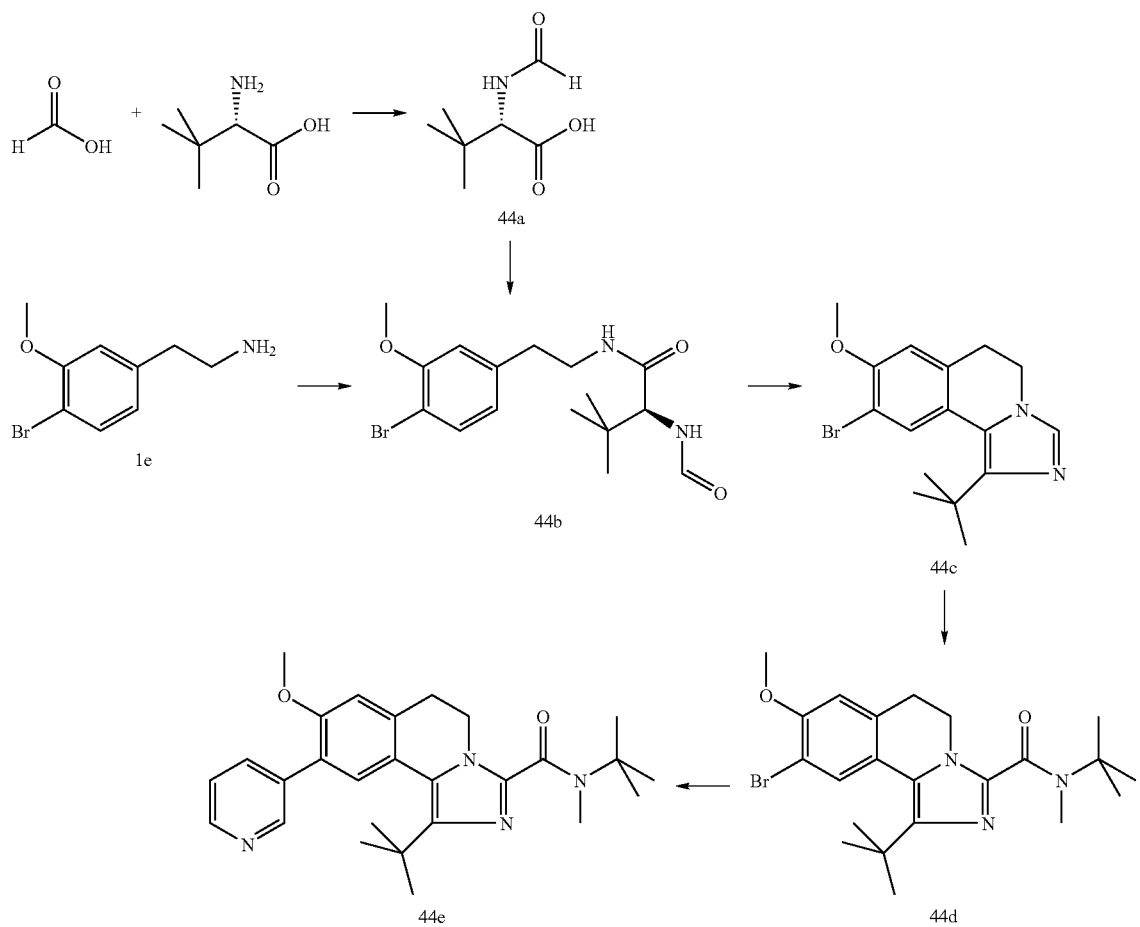

Example 44

1-tert-Butyl-8-methoxy-9-pyridin-3-yl-5,6-dihydro-imidazo[5,1-a]isoquinoline-3-carboxylic acid tert-butyl-methyl-amide (a). (S)-2-Formylamino-3,3-dimethyl-butyric acid A solution of acetic anhydride (18 ml) in dichloromethane (15 ml) was added drop wise to a cooled (0° C.) solution of and extracted with ethyl acetate. The organic layer was washed with brine, dried ($MgSO_4$), filtered and concentrated in vacuo. The residue was dissolved in hot acetone and toluene was added. After cooling to room temperature, the solids were collected, washed with acetone (at room temperature) and dried in vacuo (50° C.).

Yield: 2.76 g. LC/MS-ESI: $[M+H]^+$=371.2/373.2; $^1$H-NMR (DMSO-$d_6$) δ 0.83 (s, 9H, tert-butyl), 2.7 (t, 2H, $CH_2$), 3.3 (m, 2H, $CH_2$N), 3.82 (s, 3H, $OCH_3$), 4.2 (d, 1H, CH), 6.74 (dd, 1, ArH), 6.97 (d, 1, ArH), 7.43 (d, 1, ArH), 8.01 (d, 1, CHO), 8.17 (t, 1, NH).

(c). 9-Bromo-1-tert-butyl-8-methoxy-5,6-dihydro-imidazo[5,1-a]isoquinoline

Phosphorus pentoxide (1.8 g) was added to methanesulfonic acid (30 ml). The mixture was stirred for 30 min at 80° C. (most of $P_2O_5$ had dissolved). The product of example 44b (3.2 g) was added as a solid. The resulting mixture was stirred at 80° C. for 30 min. The reaction mixture was poured on solid $NaHCO_3$, diluted with water and extracted with ethyl acetate. The organic layer was washed with brine, dried ($MgSO_4$), filtered and concentrated in vacuo. The residue was triturated with ethyl acetate and filtered. The filtrate was concentrated in vacuo. The residue was purified by chromatography on silica gel (toluene/acetone as eluent). To a solution of the residue in acetonitrile (60 ml) (heating to dissolve), was added $POCl_3$ (5.45 ml). The reaction mixture was stirred at 80° C. for 2 h. The reaction mixture was poured on solid $NaHCO_3$, diluted with water and extracted with ethyl acetate. The organic layer was washed with brine, dried ($MgSO_4$), filtered and concentrated in vacuo. The residue was purified by chromatography on silica gel (toluene/acetone as eluent). The fractions with product were combined, and concentrated in vacuo. The residue was crystallized overnight from heptane/diethyl ether (1:1).

Yield: 1.47 g. LC/MS-ESI: $[M+H]^+$=335.1/337.1. Mp 156-157° C. NMR ($CDCl_3$) δ 1.48 (s, 9, tBu), 2.97 (t, 2, C(6)$H_2$), 4.03 (t, 2, C(5)$H_2$), 3.92 (s, 3, $OCH_3$), 6.80 (s, 1, H7), 7.42 (s, 1, H10), 7.95 (s, 1, H3).

(d). 9-Bromo-1-tert-butyl-8-methoxy-5,6-dihydro-imidazo[5,1-a]isoquinoline-3-carboxylic acid tert-butyl-methyl-amide To a solution of diisopropylamine (217 mg) in freshly distilled THF (4 ml) at 0° C., was added dropwise a solution of N-BuLi (1.6 M in hexane; 1.23 ml). The mixture was stirred for 15 min at 0° C. To a solution of the product of example 44c (300 mg) in freshly distilled THF (2 ml) at −78° C., was added drop wise the freshly prepared LDA solution (2.76 ml). The mixture was allowed to warm to 0° C. After stirring at 0° C. for 30 min, the reaction mixture was poured on $CO_2$ pellets. The mixture was stirred was continued for 15 min. The reaction mixture was concentrated in vacuo. To a solution of the remaining solid in dry DMF (6 ml) were added N-methyl-tert-butylamine (156 mg), N-ethylmorpholine (309 mg), 1-hydroxybenzotriazole (73 mg) and TBTU (431 mg). The reaction mixture was stirred at room temperature for 18 h. The mixture was poured in an aqueous $NH_4Cl$ solution and extracted with ethyl acetate (80 ml). The combined organic layers were washed with water (100 ml), brine (100 ml), dried ($Na_2SO_4$), filtered and concentrated in vacuo. The residue was purified by chromatography on silica gel in heptane/ethyl acetate [1:1 (v/v)] as eluent. The fractions containing product were combined and concentrated in vacuo. The product was triturated with diisopropylether.

Yield: 230 mg. UPLC/MS: $[M+H]^+$=448.4/450.4; $^1$H-NMR ($CDCl_3$) δ 1.45 and 1.55 (2×s, 18H, tert-butyl), 2.9 (t, 2H, C(6)$H_2$), 3.24 (s, 3H, $NCH_3$), 3.92 (s, 3H, $OCH_3$), 4.25 (t, 2h, C(5)$H_2$), 6.8 (s, 1H, ArH7), 7.91 (s, 1H, ArH10).

(e). 1-tert-Butyl-8-methoxy-9-pyridin-3-yl-5,6-dihydro-imidazo[5,1-a]isoquinoline-3-carboxylic acid tert-butyl-methyl-amide A mixture of the product of example 44d (50 mg), 3-(tributylstannyl)-pyridine (123 mg) and $Pd(PPh_3)_4$ (25 mg) in degassed toluene (2 ml) was stirred and heated in the microwave at 140° C. for 45 min. The reaction mixture was diluted with ethyl acetate. The organic layer was washed with water, brine, dried ($MgSO_4$), filtered and concentrated in vacuo. The residue was purified by chromatography on silica gel. The fractions with product were combined, concentrated in vacuo. The residue was triturated with diethyl ether to give an off white material.

Yield: 21 mg. UPLC/MS: $[M+H]^+$=447.6; $^1$H-NMR ($CDCl_3$) δ 1.47 and 1.52 (2×s, 2×9H, tert-butyl), 2.98 (t, 2H, C(6)$H_2$), 3.25 (s, 3H, $NCH_3$), 3.88 (s, 3H, $OCH_3$), 4.3 (t, 2H, C(5)$H_2$), 6.9 (s, 1H, ArH7), 7.75 (s, 1H, ArH10), 7.37, 7.88, 8.58 and 8.8 (4×m, 4, pyridine); hFSHRago (CHO luc) $EC_{50}$=33 nM.

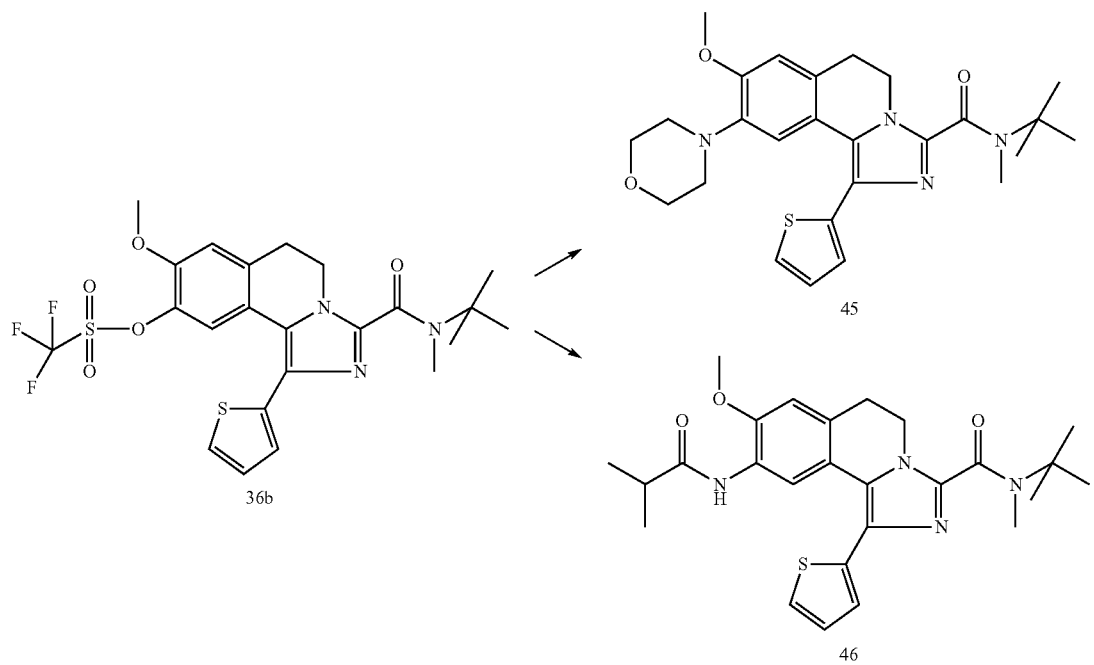

Example 45

8-Methoxy-9-morpholin-4-yl-1-thiophen-2-yl-5,6-dihydro-imidazo[5,1-a]isoquinoline-3-carboxylic acid tert-butyl-methyl-amide; trifluoro-acetic acid salt A mixture of the product of example 36b (100 mg), $K_3PO_4$ (119 mg), $Pd_2(dba)_3$ (8 mg), 2-(di-tert-butyl-phosphino)biphenyl (9 mg), morpholine (40 μl) in DME (1 ml) was stirred and heated in the microwave at 150° C. for 1 h. At room temperature, the reaction mixture was filtered and concentrated in vacuo. The residue was purified by preparative HPLC (0→100% acetonitrile; with TFA).

Yield: 53 mg. MS-ESI: $[M+H]^+=481.3$; $^1$H-NMR (CDCl$_3$) δ 1.52 (s, 9H, tert-butyl), 2.9 (m, 4, CH$_2$-morpholine), 3.1 (t, 2H, C(6)H$_2$), 3.15 (s, 3H, NCH$_3$), 3.85 (m, 4H, CH$_2$-morpholine), 3.9 (s, 3H, OCH$_3$), 4.39 (t, 2H, C(5)H$_2$), 6.79 (s, 1H, ArH7), 7.22 (s, 1H, ArH10), 7.11, 7.38 and 7.42 (3×m, 3, thiophene); hFSHRago (CHO luc) EC$_{50}$=113 nM.

Example 46

9-Isobutyrylamino-8-methoxy-1-thiophen-2-yl-5,6-dihydro-imidazo[5,1-a]isoquinoline-3-carboxylic acid tert-butyl-methyl-amide; trifluoro-acetic acid salt A mixture of the product of example 36b (120 mg), isobutyramide (38 mg), Pd$_2$(dba)$_3$ (8 mg), xantphos (10 mg), Cs$_2$CO$_3$ (215 mg) in dry dioxane (1 ml) was stirred and heated in the microwave at 150° C. for 1 h. At room temperature, the reaction mixture was filtered and concentrated in vacuo. The residue was purified by preparative HPLC (0→100% acetonitrile; with TFA).

Yield: 50 mg. MS-ESI: $[M+H]^+=481.3$; $^1$H-NMR (CDCl$_3$) δ 1.2 (d, 6, isopr.), 1.5 (s, 9H, tert-butyl), 2.52 (m, 1H, —CH), 3.1 (s+t, 5, NCH$_3$+C(6)H$_2$), 3.93 (s, 3, OCH$_3$), 4.38 (t, 2, C(5)H$_2$), 6.8 (s, 1H, ArH7), 7.67 (s, 1, ArH10), 7.17, 7.47, 7.52 (3×m, 3, thiophene), 8.68 (br.s, 1, —NH); hFSHRago (CHO luc) EC$_{50}$=148 nM.

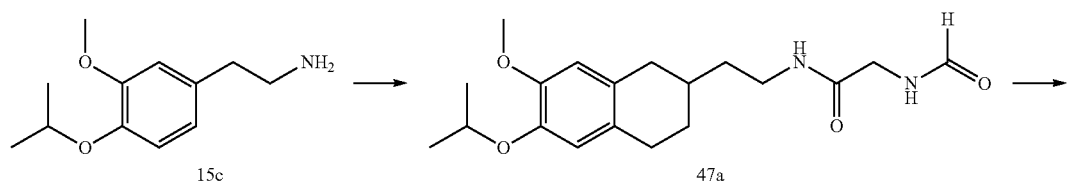

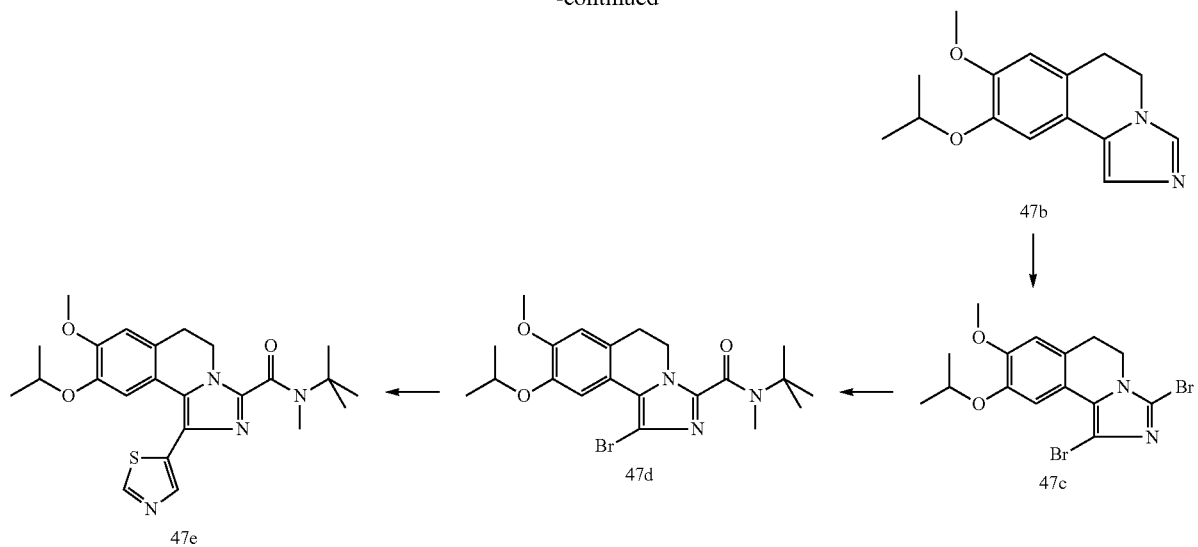

Example 47

9-Isopropoxy-8-methoxy-1-thiazol-5-yl-5,6-dihydro-imidazo[5,1-a]isoquinoline-3-carboxylic acid tert-butyl-methyl-amide (a). 2-Formylamino-N-[2-(4-isopropoxy-3-methoxy-phenyl)-ethyl]-acetamide A mixture of formylaminoacetic acid (3.1 g), the product of example 15c (6.3 g), N-ethylmorpholine (4 ml), DCC (6.6 g) and HOBT (4.5 g) in THF (35 ml) was stirred at room temperature for 4 h. The reaction mixture was diluted with diethyl ether (30 ml) and filtered over Celite. The filtrate was concentrated in vacuo. The residue was purified by chromatography on silica gel in dichloromethane/acetone [3/1→1:1 (v/v)] as eluent. The fractions containing product were combined and concentrated in vacuo. The residue was triturated with tert-butyl-methyl ether. The solids were collected and dried in vacuo (50° C.).

Yield: 8 g. TLC $R_f$=0.30 (dichloromethane/acetone 1:1); Mp: 75-82° C.; $^1$H-NMR (DMSO-d$_6$) δ 1.22 (d, 6, isoprop.), 2.65 (t, 2H, CH$_2$), 3.25 (t, 2H, CH$_2$N), 3.68 (d, 2H, CH$_2$), 3.72 (s, 3H, OCH$_3$), 6.67 (d, 1, ArH), 6.80 (br s, 1, ArH), 6.84 (d, 1, ArH), 7.97 (t, 1, NH, 8.07 (s, 1, CHO), 8.22 (br t, 1, NH).

(b). 9-Isopropoxy-8-methoxy-5,6-dihydro-imidazo[5,1-a]isoquinoline

The product of example 47a (2.0 g) in POCl$_3$ (20 ml) was stirred at 60° C. for 2 h. The reaction mixture was concentrated in vacuo and co evaporated with toluene. The residue was stirred with water for 30 min. The aqueous layer was neutralized with Na$_2$CO$_3$ and extracted with ethyl acetate. The organic layer was washed with brine, dried (MgSO$_4$), filtered and concentrated in vacuo. The residue was purified by chromatography on silica gel (dichloromethane/acetone as eluent). The fractions containing product were combined and concentrated in vacuo. The remaining residue was triturated with tert-butyl-methyl ether. The solids were collected and dried in vacuo (50° C.).

Yield: 570 mg. MS-ESI: [M+H]$^+$=259.1; TLC $R_f$=0.27 (dichloromethane/acetone 1:1); Mp: 146-148° C.; $^1$H-NMR (DMSO-d$_6$) δ 1.25 (d, 6H, isopr.), 2.92 (t, 2H, C(6)H$_2$), 3.75 (s, 3H, OCH$_3$), 4.1 (t, 2H, C(5)H$_2$), 4.58 (m, 1H, CH), 6.92 (s, 1, ArH), 6.18 (s, 1, ArH), 7.28 (s, 1, H1 (imidazo)), 7.63 (s, 1, H3 (imidazo)).

(c). 1,3-Dibromo-9-isopropoxy-8-methoxy-5,6-dihydro-imidazo[5,1-a]isoquinoline

A solution of Br$_2$ (180 µl) in acetic acid (3 ml) was added drop wise to a solution of the product of example 47b (400 mg) and sodium acetate (1.5 g) in acetic acid (8 ml). After 5 min, the reaction mixture was poured in water. A small amount of sodiumthiosulfate was added. The aqueous layer was neutralized with NaHCO$_3$ and extracted with ethyl acetate. The organic layer was washed with brine, dried (MgSO$_4$), filtered and concentrated in vacuo. The residue was purified by chromatography on silica gel (heptane/acetone as eluent). The fractions containing product were combined and concentrated in vacuo. The remaining residue was triturated with tert-butyl-methyl ether and the solids were collected and dried in vacuo (50° C.).

Yield: 340 mg. MS-ESI: [M+H]$^+$=415.1/417.1/418.9; Mp: 156-157° C. $^1$H-NMR (DMSO) δ 1.28 (d, 6H, isopr.), 3.0 (t, 2H, C(6)H$_2$), 3.8 (s, 3H, OCH$_3$), 4.07 (t, 2H, C(5)H$_2$), 4.48 (m, 1H, CH), 7.02 (s, 1H, ArH7), 7.6 (s, 1H, ArH10).

(d). 1-Bromo-9-isopropoxy-8-methoxy-5,6-dihydro-imidazo[5,1-a]isoquinoline-3-carboxylic acid tert-butyl-methyl-amide To a solution of the product of example 47c (100 mg) in dry THF (3 ml) was added at −40° C. a n-BuLi solution (0.35 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (3 ml) and N-ethylmorpholine (120 µl), were added N-methyl-tert-butylamine (0.15 ml) and TBTU (0.25 g). After stirring at room temperature for 2 h, the reaction mixture was poured into an aqueous NH$_4$Cl solution (5%) and extracted with ethyl acetate. The organic layer was dried (MgSO$_4$), filtered and concentrated in vacuo. The residue was purified by chromatography on silica gel in toluene/ ethyl acetate [7:3 (v/v)] as eluent. The fractions with product combined, concentrated in vacuo. The residue was triturated from cold heptane.

Yield: 180 mg. MS-ESI: [M+H]$^+$=450.3/452.3; TLC R$_f$=0.56 (toluene/ethyl acetate 7:3); Mp: 134-135° C.; $^1$H-NMR (DMSO-d$_6$) δ 1.3 (d, 6H, isopr.), 1.45 (s, 9H, tert-butyl), 2.98 (t, 2H, C(6)H$_2$), 3.02 (s, 3H, NCH$_3$), 3.8 (s, 3H, OCH$_3$), 4.2 (t, 2H, C(5)H$_2$), 4.5 (m, 1H, CH), 7.02 (s, 1H, ArH7), 7.68 (s, 1H, ArH10).

(e). 9-Isopropoxy-8-methoxy-1-thiazol-5-yl-5,6-dihydro-imidazo[5,1-a]isoquinoline-3-carboxylic acid tert-butyl-methyl-amide A mixture of the product of example 47d (75 mg), 5-(tributylstannyl)thiazole (200 μl) and Pd(PPh$_3$)$_4$ (30 mg) in degassed dry toluene (2 ml) was stirred under a N$_2$ atmosphere at 110° C. for 2 h. The reaction mixture was concentrated in vacuo. The residue was purified by chromatography on silica gel in toluene/acetone [3:1 (v/v)] as eluent. The fractions containing product were combined and concentrated in vacuo. The remaining residue was triturated with heptane and dried in vacuo (50° C.).

Yield: 65 mg. MS-ESI: [M+H]$^+$=455.5; TLC R$_f$=0.40 (toluene/acetone 3:1); Mp: 112-114° C.; $^1$H-NMR (DMSO-d$_6$) δ 1.15 (d, 6H, isopr.), 1.52 (s, 9H, tert-butyl), 3.0 (t, 2H, C(6)H$_2$), 3.05 (s, 3H, NCH$_3$), 3.8 (s, 3H, OCH$_3$), 4.18 (m, 3H, —CH+C(5)H$_2$), 7.03, 7.05 (2×s, 2, H7+H10), 8.07 and 9.15 (2×s, 2, thiazole H); hFSHRago (CHO luc) EC$_{50}$=6 nM.

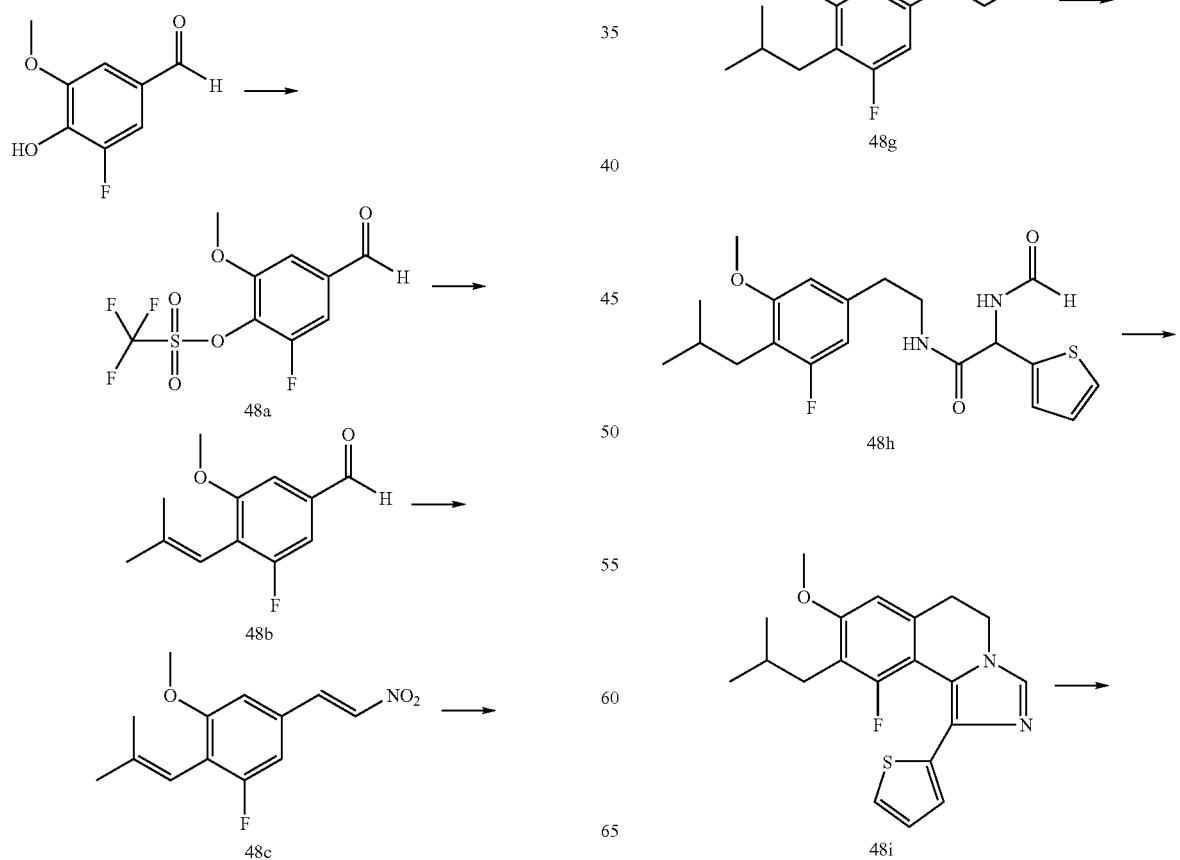

-continued

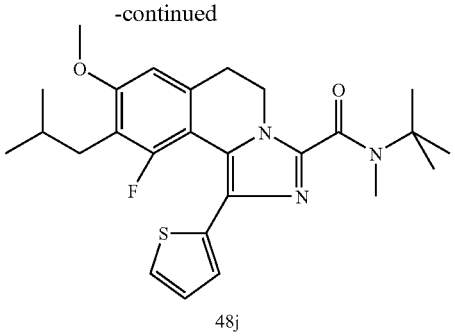

48j

Example 48

10-Fluoro-9-isobutyl-8-methoxy-1-thiophen-2-yl-5,6-dihydro-imidazo[5,1-a]isoquinoline-3-carboxylic acid tert-butyl-methyl-amide

(a). Trifluoro-methanesulfonic acid 2-fluoro-4-formyl-6-methoxy-phenyl ester Trifluoromethanesulfonic anhydride (1.2 ml) was added drop wise at −20° C. to a solution of 3-fluoro-4-hydroxy-5-methoxybenzaldehyde (1 g) and pyridine (1.5 ml) in dichloromethane (10 ml). After stirring for 15 min, the reaction mixture was poured on ice and acidified with an aqueous HCl solution (2N). The aqueous layer was extracted with ethyl acetate and the organic layer was washed with water, brine, dried (MgSO$_4$), filtered and concentrated in vacuo.

Yield: 1.8 g. TLC R$_f$=0.45 (heptane/ethyl acetate 1:1); Mp: 56-57° C.; $^1$H-NMR (CDCl$_3$) δ 4.03 (s, 3H OCH$_3$), 7.38 (m, 2H, ArH), 9.95 (s, 1H, CHO).

(b). 3-Fluoro-5-methoxy-4-(2-methyl-propenyl)-benzaldehyde

A mixture of the product of example 48a (1.6 g), example 18a (1.6 g), K$_2$CO$_3$ (1 g) in DME (20 ml) and water (4 ml) was degassed by flushing with N$_2$ for 5 min. Pd(PPh$_3$)$_4$ (100 mg) was added. The reaction mixture was heated under N$_2$ for 6 h at 90° C. At room temperature, the mixture was diluted with ethyl acetate. The organic layer was washed with brine, dried (MgSO$_4$), filtered and concentrated in vacuo. The residue was purified by chromatography on silica gel (heptane/ethyl acetate as eluent).

Yield: 1.1 g. LC/MS-ESI: [M+H]$^+$=209.1; TLC R$_f$=0.60 (heptane/ethyl acetate 1:1); $^1$H-NMR (CDCl$_3$) δ 1.63, 1.97 (2×d, 6H, isobutylene), 3.9 (s, 3H, OCH$_3$), 5.96 (br s, 1H, =CH), 7.2 (m, 2H, ArH), 9.91 (s, 1H, CHO).

(c). 1-Fluoro-3-methoxy-2-(2-methyl-propenyl)-5-((E)-2-nitro-vinyl)-benzene A mixture of the product of example 48b (1.1 g), ammonium acetate (2.5 g) and nitromethane (3 ml) in acetic acid (25 ml) was heated at 85° C. for 5 h. At room temperature, water (30 ml) was added and after stirring for 15 minutes the solids were collected and dried in vacuo.

Yield: 1.1 g. LC/MS-ESI: [M+H]$^+$=252.1; TLC R$_f$=0.62 (heptane/ethyl acetate 1:1); Mp: 131-133° C., $^1$H-NMR (CDCl$_3$) δ 1.65, 1.98 (2×dd, 6H, isobutylene), 3.88 (s, 3H, OCH$_3$), 5.93 (br s, 1H, =CH), 6.79 (br s, 1, ArH), 6.93 (dd, 1, ArH), 7.56 and 7.92 (2×dd, 2, CH=CHNO$_2$).

(d). 2-[3-Fluoro-5-methoxy-4-(2-methyl-propenyl)-phenyl]-ethylamine

A solution of the product of example 48c (1.1 g) in THF (15 ml) was added drop wise to a suspension of LiAlH$_4$ (920 mg) in THF/diethyl ether (40 ml; 1:1 (v/v)). After stirring at 75° C. for 1 h, the reaction mixture was quenched by drop wise addition of water (1 ml), an aqueous NaOH solution (1 ml 4N) and water (3 ml). The resulting suspension was filtered over Celite, concentrated in vacuo. The residue taken up in diethyl ether, dried (MgSO$_4$), filtered and concentrated in vacuo.

Yield: 1.05 g. LC/MS-ESI: [M+H]$^+$=224.2; $^1$H-NMR (CDCl$_3$) δ 1.62 and 1.95 (2×dd, 6H, isobutylene), 2.72 (t, 2H, CH$_2$), 3.0 (t, 2H, CH$_2$N), 3.82 (s, 3H, OCH$_3$), 5.9 (s, 1H, CH), 6.50 (br s, 1, ArH), 6.55 (dd, 1, ArH).

(e). N-{2-[3-Fluoro-5-methoxy-4-(2-methyl-propenyl)-phenyl]-ethyl}-formamide The product of example 48d (1.05 g) in ethylformate (20 ml) was heated at 80° C. for 5 h, concentrated in vacuo and the residue was purified by chromatography on silica gel (heptane/acetone as eluent).

Yield: 720 mg. LC/MS-ESI: [M+H]$^+$=252.1; TLC R$_f$=0.45 (heptane/acetone 1:1); Mp: 81-83° C.; $^1$H-NMR (CDCl$_3$) δ 1.62, 1.95 (dd, 6H, 2×CH$_3$), 2.82 (t, 2H, CH$_2$), 3.58 (t, 2H, CH$_2$N), 3.82 (s, 3H, OCH$_3$), 5.6 (br.s., 1H, NH), 5.9 (s, 1H, =CH), 6.50 (br s, 1, ArH,), 6.55 (dd, 1, ArH), 8.17 (s, 1H, CHO).

(f). N-[2-(3-Fluoro-4-isobutyl-5-methoxy-phenyl)-ethyl]-formamide

A solution of the product of example 48e (720 mg) in ethyl acetate (30 ml) was hydrogenated in the presence of Pd/C (10%; 100 mg). After 16 h, the catalyst was filtered. The filtrate was concentrated in vacuo. The residue was treated with heptane to afford a white crystalline material.

Yield: 640 mg. LC/MS-ESI: [M+H]$^+$=254.2; TLC R$_f$=0.43 (heptane/acetone 1:1); Mp: 78-79° C.; $^1$H-NMR (CDCl$_3$) δ 0.88 (d, 6H, isobutyl), 1.87 (m, 1H, —CH), 2.45 (dd, 2H, —CH$_2$, isobutyl), 2.8 (t, 2H, ArCH$_2$), 3.58 (q, 2H, CH$_2$N), 3.8 (s, 3H, OCH$_3$), 5.5 (br.s, 1H, NH), 6.47 (br s, 1H, ArH), 6.51 (dd, 1, ArH), 8.16 (s, 1H, CHO).

(g). 1-Fluoro-2-isobutyl-5-(2-isocyano-ethyl)-3-methoxy-benzene

A solution of POCl$_3$ (0.28 ml) in THF (3 ml) was added drop wise at −20° C. to a solution of the product of example 48f (620 mg) and Et$_3$N (2 ml) in THF (6 ml). After stirring at −20° C. for 1 h, water was added. The mixture was stirred was continued for 1.5 h. The mixture was extracted with diethyl ether. The organic layer was dried (MgSO$_4$), filtered and concentrated in vacuo. The residue was purified by chromatography on silica gel in heptane/ethyl acetate [1:1 (v/v)] as eluent.

Yield: 530 mg. TLC R$_f$=0.75 (heptane/acetone 1:1); $^1$H-NMR (CDCl$_3$) δ 0.82 (d, 6H, isobut.), 1.8 (m, 1H, —CH), 2.41 (dd, 2H, —CH$_2$), 2.88 (t, 2H, CH$_2$), 3.54 (t, 2H, CH$_2$N), 3.75 (s, 3H, OCH$_3$), 6.45 (m, 2H, ArH).

(h). N-[2-(3-Fluoro-4-isobutyl-5-methoxy-phenyl)-ethyl]-2-formylamino-2-thiophen-2-yl-acetamide A mixture of the product of example 48g (530 mg), thiophene-2-carboxaldehyde (253 mg) and ammonium acetate (300 mg) in methanol (5 ml) was refluxed for 6 h. At room temperature, the reaction mixture was poured in water. The mixture was extracted with ethyl acetate. The organic layer was washed with brine, dried (MgSO$_4$), filtered and concentrated in vacuo. The residue was purified by chromatography on silica gel in heptane/acetone [1:1 (v/v)] as eluent. The fractions with product were combined and concentrated in vacuo. The residue was treated with heptane/diisopropylether to afford a white crystalline product.

Yield: 470 mg. LC/MS-ESI: [M+H]$^+$=393.2; TLC R$_f$=0.43 (heptane/acetone 1:1); Mp: 131-132° C.; $^1$H-NMR (DMSO-d$_6$) δ 0.83 (d, 6H, 2×CH$_3$), 1.8 (q, 1H, —CH), 2.4 (d, 2H, CH$_2$), 2.7 (t, 2H, CH$_2$), 3.3 (m, 2H, CH$_2$N), 3.73 (s, 3H, OCH$_3$), 5.72 (d, 1H, CH), 6.58 (d, 1, ArH), 6.63 (br s, 1, ArH), 6.93 (m, 2, thiophene), 7.41 (m, 1, thiophene), 8.02 (br s, 1, CHO), 8.47 (t, 1, NH), 8.86 (d, 1, NH).

(i). 10-Fluoro-9-isobutyl-8-methoxy-1-thiophen-2-yl-5,6-dihydro-imidazo[5,1-a]iso-quinoline A solution of methanesulphonic acid (10 ml) and P$_2$O$_5$ (1.5 g) was heated at 75° C. for 30 min. The product of example 48h (400 mg) was added. The mixture was stirred at 75° C. for 1 h. The reaction mixture was poured on a mixture of NaHCO$_3$ (30 g) in water (30 ml). The mixture was stirred for 5 min, further diluted with water and extracted with ethyl acetate. The organic layer was washed once with an aqueous NaOH (2N) solution, water, brine, dried (MgSO$_4$), filtered and concentrated in vacuo. The residue was purified by chromatography on silica gel (heptane/acetone as eluent). The fractions with product were combined, concentrated in vacuo. The residue was treated with cold diethyl ether to afford a white crystalline product.

Yield: 280 mg. LC/MS: [M+H]$^+$=357.0; TLC R$_f$=0.32 (heptane/acetone 1:1); Mp: 148-149° C.; $^1$H-NMR (DMSO-d$_6$) δ 0.85 (d, 6H, isobutyl), 1.8 (m, 1H, CH-isobutyl), 2.4 (d, 2, CH$_2$-isobutyl), 3.02 (t, 2H, C(6)H$_2$), 3.85 (s, 3H, OCH$_3$), 4.1 (t, 2H, C(5)H$_2$), 6.8, 6.99, 7.4 (m, 3H, thiophene), 6.95 (s, 1H, ArH7), 7.83 (s, 1, H3 imidazo).

(j). 10-Fluoro-9-isobutyl-8-methoxy-1-thiophen-2-yl-5,6-dihydro-imidazo[5,1-a]isoquinoline-3-carboxylic acid tert-butyl-methyl-amide To a suspension of the product of example 48i (250 mg) in dry THF (3 ml) at −40° C. was added a solution of n-BuLi (0.5 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (2 ml) and N-ethylmorpholine (0.2 ml), were added N-methyl-tert-butylamine (0.2 ml) and TBTU (0.35 g). After stirring at room temperature for 2 h, the reaction mixture was poured into an aqueous NH$_4$Cl solution (5%) and extracted with ethyl acetate. The organic layer was dried (MgSO$_4$), filtered and concentrated in vacuo. The residue was purified by chromatography on silica gel in heptane/acetone [1:1 (v/v)] as eluent. The fractions with product combined and concentrated in vacuo. The residue was triturated from heptane/10% diisopropylether and dried in vacuo (50° C.).

Yield: 170 mg. LC/MS-ESI: [M+H]$^+$=470.2; TLC R$_f$=0.60 (heptane/acetone 1:1); Mp: 141-142° C.; $^1$H-NMR (DMSO-d$_6$) δ 0.85 (d, 6, isobutyl), 1.48 (s, 9H, tert-butyl), 1.8 (m, 1H, —CH-isobutyl), 2.4 (d, 2H, CH2-isobutyl), 3.03 (t, 2H, C(6)H$_2$), 3.08 (s, 3H, NCH$_3$), 3.86 (s, 3H, OCH$_3$), 4.15 (t, 2H, C(5)H$_2$), 6.85 (m, 1, H7), 6.98 (m, 2, thiophene), 7.43 (m, 1, thiophene); hFSHRago (CHO luc) EC$_{50}$=7 nM.

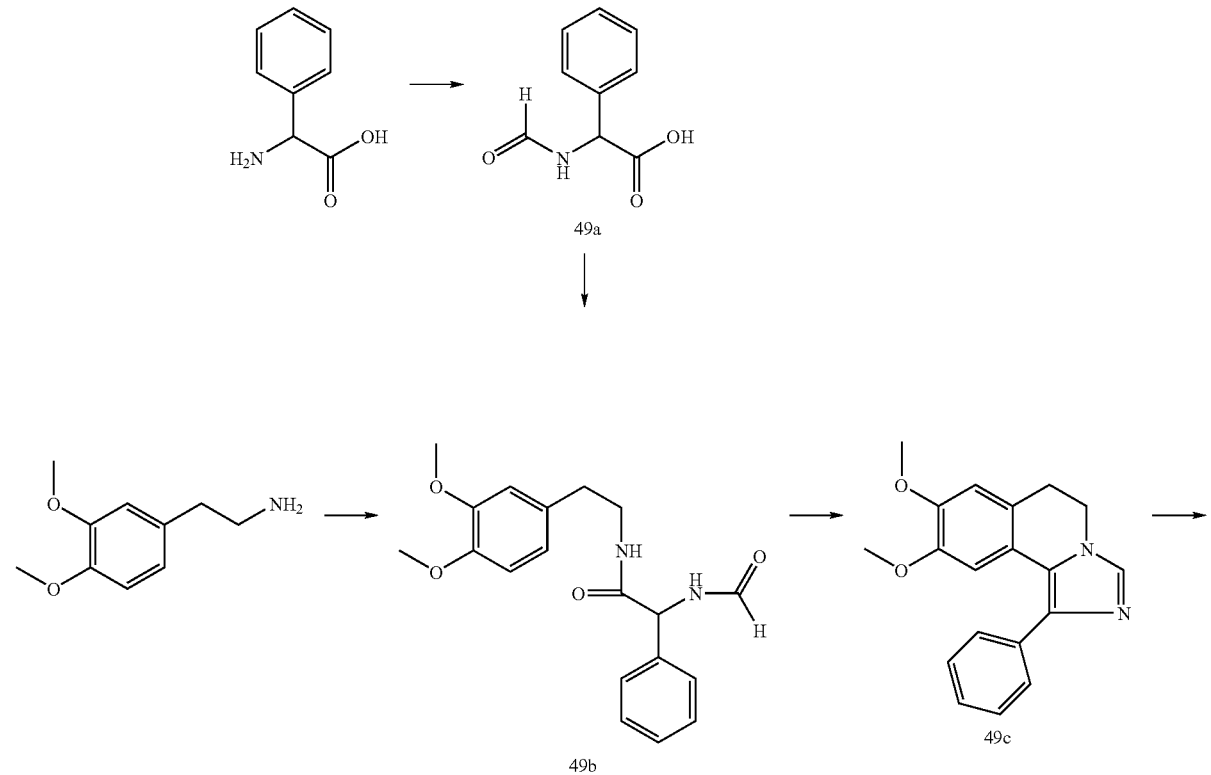

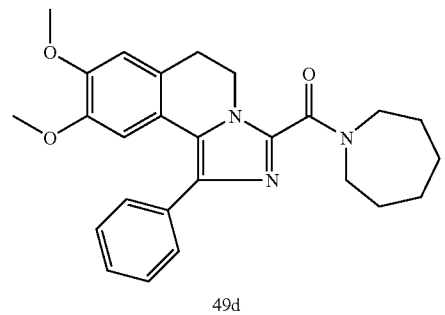

49d

Example 49

Azepan-1-yl-(8,9-dimethoxy-1-phenyl-5,6-dihydro-imidazo[5,1-a]isoquinolin-3-yl)-methanone; hydrochloride salt

(a). Formylamino-phenyl-acetic acid

A mixture of acetic anhydride (7 ml), formic acid (20 ml) and phenylglycine (1.8 g) was stirred at 60° C. for 4 h. At room temperature, water (25 ml) was added. The mixture was stirred at room temperature for 30 min. The mixture was concentrated in vacuo. The residue was crystallized from boiling water (10 ml). The solids were collected and dried in vacuo (50° C.).

Yield: 1.1 g. Mp: 173-178° C.; $^1$H-NMR (DMSO-$d_6$) δ 5.4 (d, 1H, CH), 7.4 (m, 5H, ArH), 8.05 (s, 1H, CHO), 8.9 (d, 1H, NH), 13.0 (br.s, 1H, COOH).

(b). N-[2-(3,4-Dimethoxy-phenyl)-ethyl]-2-formylamino-2-phenyl-acetamide

A mixture of the product of example 49a (0.9 g), 2-(3,4-dimethoxy-phenyl)-ethylamine (0.9 g), TBTU (1.8 g) and DIPEA (0.9 ml) in DMF (10 ml) was stirred at room temperature for 16 h. The reaction mixture was poured into water and extracted with ethyl acetate. The organic layer was washed with brine, dried (MgSO$_4$), filtered and concentrated in vacuo. The residue was treated with tert-butyl-methyl ether/heptane (v/v 1:1). The solids were collected and dried in vacuo (50° C.).

Yield: 1.25 g. TLC $R_f$=0.65 (dichloromethane/acetone 1:1); Mp: 136-137° C.; NMR (CDCl$_3$) δ 2.65 (m, 2, CH$_2$), 3.40 and 3.55 (2×m, 2, CH2), 5.40 (d, 1, CH), 8.20 (s, 1, CHO), 5.65 (br t, 1, NH), 7.08 (bd, 1, NH), 6.49 (dd, 1, ArH), 6.58 (d, 1, ArH), 6.72 (d, 1, ArH), 7.32 (m, 5, phenyl).

(c). 8,9-Dimethoxy-1-phenyl-5,6-dihydro-imidazo[5,1-a]isoquinoline

A solution of methanesulphonic acid (6 ml) and P$_2$O$_5$ (900 mg) was heated at 75° C. for 30 min. The product of example 49b (1.0 g) was added. The mixture was stirred at 75° C. for 1 h. The reaction mixture was poured on NaHCO$_3$/water. The mixture was extracted with ethyl acetate. The organic layer was washed with an aqueous NaOH solution (2 M), water, brine, dried (MgSO$_4$), filtered and concentrated in vacuo. The residue was triturated with tert-butyl-methyl ether/heptane.

Yield: 0.75 g. MS-ESI: [M+H]$^+$=307.4; TLC $R_f$=0.37 (heptane/acetone 1:1); Mp: 130-133° C.; $^1$H-NMR (CDCl$_3$) δ 3.02 (t, 2H, C(6)H$_2$), 3.58, 3.9 (2×s, 6H, 2×OCH$_3$), 4.17 (t, 2H, C(5)H$_2$), 6.75 (s, 1, H7), 7.12 (s, 1, H10), 7.56 (s, 1, H3 imidazo), 7.31 (m, 1, ArH), 7.40 (m, 2, ArH), 7.72 (m, 2, ArH).

(d). Azepan-1-yl-(8,9-dimethoxy-1-phenyl-5,6-dihydro-imidazo[5,1-a]isoquinolin-3-yl)-methanone; hydrochloride salt To a suspension of the product of example 49c (150 mg) in dry THF (4 ml) at −40° C. was added a n-BuLi solution (0.4 ml, 1.6 M in heptane). After stirring for 10 min at −40° C., the reaction mixture was poured on CO$_2$ pellets. The mixture was stirred for 15 min and concentrated in vacuo at 35° C. To a solution of the residue in DMF (3 ml) and N-ethylmorpholine (0.1 ml), were added azepane (0.2 ml) and TBTU (0.25 g). After stirring at room temperature for 2 h, the reaction mixture was poured in an aqueous NH$_4$Cl solution (5%) and extracted with ethyl acetate. The organic layer was dried (MgSO$_4$), filtered and concentrated in vacuo. The residue was purified by chromatography on silica gel (toluene/acetone as eluent). The residue was dissolved in diethyl ether and treated with a HCl solution (2 M in dioxane).

Yield: 42 mg. MS-ESI: [M+H]$^+$=432.4; TLC $R_f$=0.40 (heptane/ethyl acetate 7:3); $^1$H-NMR (DMSO-$d_6$) δ 1.57 (m, 4H, azepane), 1.78 (m, 4H, azepane), 3.02 (m, 2H, H5), 3.60 (m, 2H, azepane), 3.82 (m, 2H, azepane), 3.42 (s, 3H, OCH$_3$), 3.80 (s, 3H, OCH$_3$), 4.30 (m, 2H, H6), 7.37 (m, 1H, phenyl), 7.48 (m, 2H, phenyl), 7.66 (m, 2H, phenyl); hFSHRago (CHO luc) EC$_{50}$=630 nM.

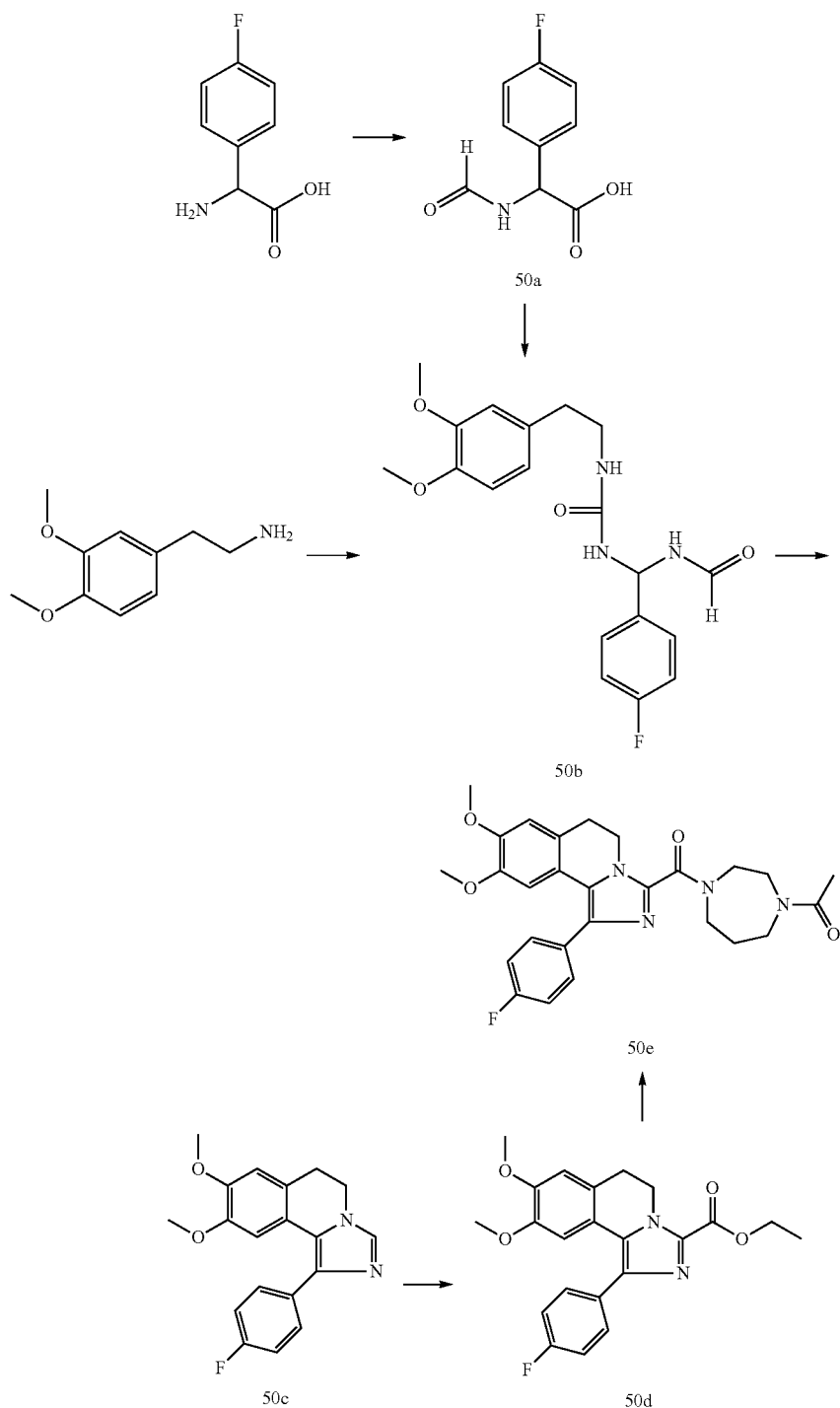

Example 50

1-{4-[1-(4-Fluoro-phenyl)-8,9-dimethoxy-5,6-dihydro-imidazo[5,1-a]isoquinoline-3-carbonyl]-[1,4]diazepan-1-yl}-ethanone; hydrochloride salt (a). (4-Fluorophenyl)-formylamino acetic acid To a solution of (4-fluorophenyl)glycine (1.9 g) in formic acid (20 ml) was added acetic anhydride (7 ml). After stirring for 5 h, the reaction was concentrated in vacuo to 10 ml. Water (25 ml) was added. After additional stirring for 30 min, the reaction mixture was concentrated in vacuo. The residue was triturated with water, filtered, and dried in vacuo, to provide white crystals.

Yield: 1.7 g. Mp: 190-203° C.; $^1$H-NMR (DMSO-d$_6$) δ 5.40 (d, 1, CH), 8.97 (d, 1, NH), 8.08 (s, 1, CHO), 7.22 and 7.43 (2×m, 4, Ar(F)H), 13.10 (s, 1, COOH); $^{19}$F-NMR (DMSO-d$_6$) δ −114.97.

(b). N-[2-(3,4-Dimethoxyphenyl)-ethyl]-2-(4-fluorophenyl)-2-formylaminoacetamide To a mixture of N-formyl-4-fluorophenylglycine (900 mg) and 2,3-dimethoxyphenethylamine (1 ml) in DMF (5 ml) was added N-ethylmorpholine (0.75 ml) and TBTU (1.6 g). After stirring for 4 h, the reaction was quenched by addition of water (30 ml). The product was extracted with ethylacetate. The organic layer was washed with water, dried ($MgSO_4$), filtered and concentrated in vacuo. The residue was triturated with methyl-tert.butylether and recrystallized from toluene.

Yield: 1.5 g. Mp: 147-150° C.; NMR (DMSO-$d_6$) δ 3.68, 3.70 (2×s, 6, $OCH_3$), 2.61 (t, 2, $ArCH_2$), 3.25 (m, 2, $CH_2N$—), 5.48 (d, 1, CH)), 6.58, 6.73, 6.78 (3×m, 3, ArH), 7.12 and 7.36 (2×m, 4, F—Ar—H), 8.40 (t, 1, NH), 8.04 (s, 1, CHO), 8.85 (d, 1, NH), 8.40 (t, 1, NH).

(c). 1-(4-Fluorophenyl)-8,9-dimethoxy-5,6-dihydro-imidazo[5,1-a]isoquinoline A mixture of $P_2O_5$ (150 mg) and methanesulfonic acid (1 ml) was heated at 90° C. for 30 min. The product of 50b (100 mg) was added. The reaction mixture was heated at 90° C. for 1.5 h. The reaction mixture was poured in ice water and neutralized by the addition of $Na_2CO_3$. The product was extracted with ethyl acetate. The organic layer was dried ($MgSO_4$), filtered and concentrated in vacuo. The residue was treated with ether/diisopropyl ether mixture.

Yield: 55 mg. Mp: 185-188° C.; NMR (DMSO-$d_6$) δ 7.77 (s, 1, imidazole-H2), 7.65 and 7.25 (2×m, 4, F—Ar—H), 6.96 and 6.98 (2×s, 2, H7 and H10), 3.48 and 3.78 (2×s, 6, $OCH_3$), 3.00 (t, 2, H6), 4.13 (t, 2, H5); $^{19}$F-NMR (DMSO-$d_6$)-115.7.

(d). 1-(4-Fluoro-phenyl)-8,9-dimethoxy-5,6-dihydro-imidazo[5,1-a]isoquinoline-3-carboxylic acid, ethyl ester To a suspension of the product of 50c (300 mg) in 6 ml of dry THF (6 ml) at −60° C. under nitrogen was added a solution of n-BuLi in hexane (0.7 ml, 1.6M). After stirring for 30 min, ethylchloroformate (100 µl) was added. The mixture was stirred for another 15 min and after the removal of the cooling, for 15 min at ambient temperature. The reaction mixture was quenched by addition of water and extracted with ethyl acetate. The organic layer was dried ($MgSO_4$), filtered and concentrated in vacuo. The residue was purified by chromatography over silica gel (heptane/acetone as eluent). The residue was triturated with diisopropyl ether.

Yield: 60 mg. Mp: 198-200° C.; NMR ($CDCl_3$) δ 1.48 (t, 3, $CH_3$), 4.48 (q, 2, $CH_2$), 3.51 and 3.90 (2×s, 6, $OCH_3$), 3.06 (t, 2, H6), 4.09 (t, 2, H5), 6.78 and 6.91 (2×s, 2, H7 and H10), 7.09 and 7.66 (2×m, 4, F—Ar—H); $^{19}$F-NMR ($CDCl_3$)-114.3.

(e). 1-{4-[1-(4-Fluoro-phenyl)-8,9-dimethoxy-5,6-dihydro-imidazo[5,1-a]isoquinoline-3-carbonyl]-[1,41]diazepan-1-yl}-ethanone; hydrochloride salt A solution of the product of 50d (60 mg) in dioxane (1 ml) was treated with a solution of LiOH (20 mg) in water (0.3 ml). The mixture was stirred for 45 min and neutralized by addition of an aqueous HCl solution (0.5 N). The aqueous material was freeze-dried and diluted with DMF (1 ml). N-acetylhomopiperidine (30 mg), N-ethylmorpholine (30 ml) and TBTU (60 mg) were added. The reaction mixture was stirred for 4 h, poured in water and extracted with ethyl acetate. The organic layer was dried ($MgSO_4$), filtered and concentrated in vacuo. The residue was purified by chromatography on silica gel (dichloromethane/acetone as eluent). The product was dissolved in a mixture of acetone/ether (v:v, 1:1) and treated with one equivalent of a 0.4N HCl solution in ether.

Yield: 10 mg. MS-ESI: $[M+H]^+$=493.4; TLC $R_f$=0.50 (dichloromethane/acetone 1:1); NMR (DMSO-$d_6$) δ 2.00 (m, 3, acetyl(rotamers)), 3.47 and 3.80 (2×s, 6, $OCH_3$), 6.95 and 7.02 (2×s, 2, H7 and H10), 7.30 and 7.69 (2×m, F—Ar—H); $^{19}$F-NMR (DMSO-$d_6$)-114.9; hFSHRago (CHO luc) $EC_{50}$=315 nM.

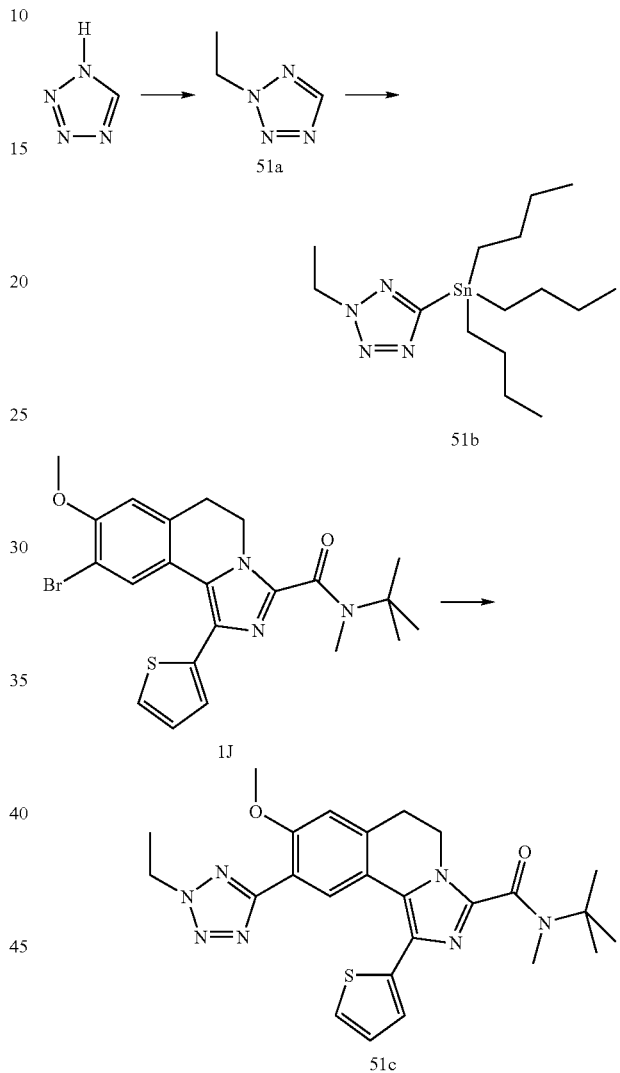

Example 51

9-(2-Ethyltetrazol-5-yl-)-8-methoxy-1-thiophen-2-yl-5,6-dihydro-imidazo[5,1-a]isoquinoline-3-carboxylic acid tert-butyl-methyl-amide

(a) 2-Ethyltetrazole

To a suspension of NaH (2.50 g 60% dispersion in mineral oil) in DMF (33 ml) was added in small portions (4.4 g, 62 mmol) of tetrazole at 0-5° C. After stirring for additional 20 min, a solution of iodoethane (9.8 g) in DMF (5 ml) was added drop wise. The reaction mixture was kept at room temperature for 2 h (slightly exothermic) and subsequently stirred for 12 h. The reaction mixture was poured in water and extracted with ether. The organic layer was washed with brine, dried (MgSO$_4$), filtered and concentrated in vacuo. The residue was distilled to afford the 2-ethyltetrazole (bp 80° C., 50 mbar).

Yield: 920 mg NMR (CDCl$_3$) δ 1.65 (t, 3H, CH$_3$), 4.70 (q, 2H, CH$_2$), 8.51 (s, 1H, H4).

(b) 2-Ethyl-5-tributylstannanyl-2H-tetrazole

To a solution of the product of example 51a (100 mg) in dry THF (4 ml) at −60° C. was added under N$_2$ a solution of BuLi in hexane (700 μl, 1.6M). The mixture was stirred for 40 min at −60° C. (white precipitate formed). Tributyltinchloride (360 mg) in THF (3 ml) was introduced drop wise. The reaction mixture was stirred for 15 min at −60° C., for 30 min in an ice bath and quenched by the addition of an aqueous NH$_4$Cl solution (30 ml 5%). The mixture was extracted with ethyl acetate. The organic layer was washed with brine, dried (MgSO$_4$), filtered and concentrated in vacuo. The residue was purified by chromatography on silica gel (pentane/ether gradient).

Yield: 400 mg. R$_f$ (heptane/ether 5/1) 0.30. NMR (CDCl$_3$) δ 0.88 (t, 9H, 3×CH$_3$ butyl), 1.63 (t, 3H, CH$_3$ ethyl), 1.20, 1.33, 1.58 (3 m, 18H, CH$_2$ butyl).

(c) 9-(2-Ethyltetrazol-5-yl-)-8-methoxy-1-thiophen-2-yl-5,6-dihydro-imidazo[5,1-a]isoquinoline-3-carboxylic acid tert-butyl-methyl-amide A solution of the product of example 1j (300 mg), the product of example 51b (380 mg) and Pd(PPhe$_3$)$_4$ (50 mg) in degassed toluene (6 ml), was heated under a N$_2$ atmosphere for 48 h at 115° C. The reaction mixture was cooled and purified by chromatography on silica gel with a gradient of toluene/ethyl acetate. The residue was triturated with diethyl ether to give white crystals.

Yield: 180 mg. Mp 121-123° C. TLC Rf (toluene/ethyl acetate 1/1) 0.5. NMR (CDCl$_3$) δ 1.49 (s, 9H, tbutyl), 1.64 (t, 3H, ethyl), 3.11 (t, 2H, H6), 3.95 (s, 3H, OCH$_3$), 4.35 (t, 2H, H5), 4.65 (q, 2H, ethyl), 3.18 (s, 3H, NCH$_3$), 6.47 (s, 1H, H2), 6.90 (s, 1H, H7), 8.18 (s, 1H, H10), 7.04, 7.10, 7.27 (3×m, 3H, thiophene); hFSHRago (CHO luc) EC$_{50}$=5 nM.

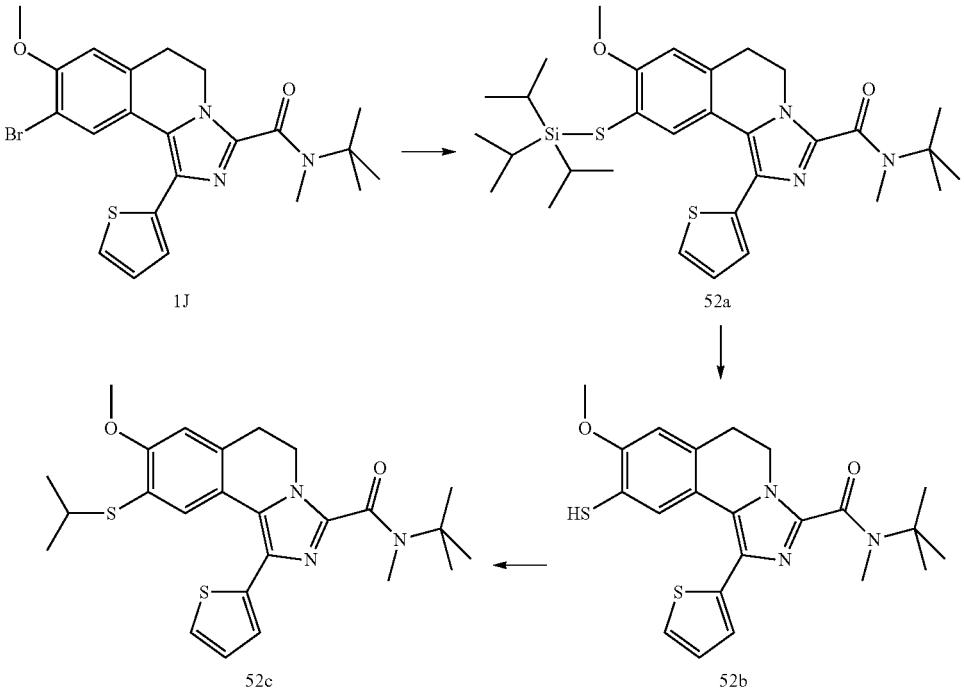

Example 52

9-Isopropylsulfanyl-8-methoxy-1-thiophen-2-yl-5,6-dihydro-imidazo[5,1-a]isoquinoline-3-carboxylic acid tert-butyl-methyl-amide; hydrochloride salt (a) 8-Methoxy-1-thiophen-2-yl-9-triisopropylsilanyl-sulfanyl-5,6-dihydro-imidazo[5,1-a]iso-quinoline-3-carboxylic acid tert-butyl-methyl-amide A suspension of sodium hydride (80 mg of 60% NaH, washed oil free with dry pentane) in toluene (2 ml) was treated drop wise with triisopropylsilanethiol (470 μl) under a N$_2$ atmosphere. After subsiding of gas evolution the mixture was stirred for an additional 10 min. The product of example 1j (950 mg) in toluene (10 ml) was added, followed by the addition of palladiumtetrakistriphenylphosphine (100 mg). The reaction mixture was heated at 90° C. for 16 h. The mixture was concentrated in vacuo and purified by chromatography on silica gel with an eluent of toluene/ethyl acetate.

Yield: 370 mg. Mp 162° C.; NMR (CDCl$_3$) δ 1.55 (s, 9, tert.Bu), 0.98 (d, 18, isoprop), 1.12 (m, 3, CH-isopr), 3.05 (t, 2, H4), 4.38 (t, 2, H5), 3.88 (s, 3, OCH$_3$), 3.25 (s, 3, NCH3), 6.72 (s, 1, H7), 7.88 (s, 1, H10), 7.07, 7.28, 7.33 (3×m, 3, thiophene).

(b) 9-Mercapto-8-methoxy-1-thiophen-2-yl-5,6-dihydro-imidazo[5,1-a]isoquinoline-3-carboxylic acid tert-butyl-methyl-amide Deprotection of the product of example 52a was achieved by treating a solution the product of example 52a (370 mg) in THF (7 ml) with a solution of TBAF in THF (1 ml, 1M). After stirring for 1 h, the mixture was poured in an aqueous NH$_4$Cl solution (5%) and extracted with ethylacetate. The residue was purified by chromatography on silica gel with heptane/ethyl acetate as eluent. The residue was crystallized upon treatment with diisopropylether Yield: 250 mg. Mp 186° C.; Rf (heptane/ethyl acetate 1/1) 0.40; NMR (CDCl$_3$) δ 1.55 (s, 9, tert.Bu), 3.03 (t, 2, H4), 4.39 (t, 2, H5), 3.93 (s, 3, OCH$_3$), 3.24 (s, 3, NCH$_3$), 6.76 (s, 1, H7), 7.63 (s, 1, H10), 7.08, 7.31, 7.34 (3×m, 3, thiophene).

(c) 9-Isopropylsulfanyl-8-methoxy-1-thiophen-2-yl-5,6-dihydro-imidazo[5,1-a]iso-quinoline-3-carboxylic acid tert-butyl-methyl-amide; hydrochloride salt A solution of the product of example 52b (20 mg) in DMF (0.5 ml) under nitrogen atmosphere was treated with NaH (3 mg 60% dispersion in mineral oil). After stirring for 5 min, 2-bromopropane (7 µl) was added. The reaction mixture was stirred for 1 h. The mixture was diluted with water and extracted with ethyl acetate. The residue was purified by chromatography on silica gel with (heptane/ethyl acetate as eluent). The product isolated was dissolved in ether and converted to the hydrochloride salt by addition of a solution of HCl in ether (0.2 M), until weakly acidic.

Yield: 8 mg. Mp 127° C.; Rf (heptane/ethyl acetate 1/1) 0.52 (free base); NMR (CDCl3) δ 1.20 (dd, 6H, isopropyl), 1.60 (s, 9H, tbutyl), 3.12 (m, 1H, CH isopropyl), 3.80 (m, 2H, H4), 3.23 (s, 3H, NCH$_3$), 3.93 (s, 3H, OCH$_3$), 4.40 (m, 2H, H5), 6.78 (s, 1H, H7), 7.52 (s, 1H, H10, 7.18, 7.41, 7.68 (3×m, 3H, thiophene); hFSHRago (CHO luc) EC$_{50}$=16 nM

Example 53

Agonistic Activity of Compounds at the Human FSH Receptor Expressed in CHO Cells Agonistic activity of the compounds at the human FSH receptor was determined in Chinese Hamster Ovary (CHO) cells stably transfected with the human FSH receptor and cotransfected with a cAMP responsive element (CRE)/promotor directing the expression of a firefly luciferase reporter gene. Binding of the compounds to the Gs protein-coupled FSH receptor will result in an increase of cAMP, which in turn will induce an increased transactivation of the luciferase reporter. Cells (7,500 cells/well of a 384 well plate) were incubated in Dulbecco' minimal essential F12 modified medium (Invitrogen), supplemented with 1 µg/ml bovine insulin, 5 µg/ml human apo-transferrin, 80 U/ml penicillin G and 80 µg/ml streptomycin with the test compounds (concentration between 0.0316 nM and 10.0 µM) in duplicate in a humidified atmosphere (95%) at 5-7% CO2 and 37° C. The final concentration of DMSO was 1%. After 4 hours of incubation, plates were allowed to adjust to room temperature for 1 hour. Then, Luclite (PerkinElmer) solution was added to the wells and cells were allowed to lyse for at least 1 hour at room temperature. Subsequently, luciferase activity was measured in a luminescence counter. The signal is expressed as counts per second (cps). The EC$_{50}$ (concentration of the test compound that elicits half-maximal (50%) luciferase stimulation compared to the compound's maximally attainable effect) and efficacy values (maximal effect of the test compound as percentage of the maximal effect of recombinant human FSH) of the compounds were determined using the software program MathIQ (version 2.0, ID Business Solutions Limited). EC$_{50}$ data are indicated at the synthesis examples.

What is claimed is:
1. A compound according to formula I:

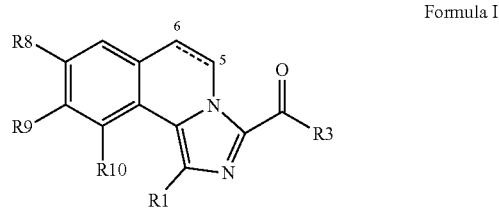

Formula I or a pharmaceutically acceptable salt thereof wherein
the C5-C6 bond can either be saturated or unsaturated;
R$^1$ is phenyl or (2-5C)heteroaryl, both optionally substituted with one or more substituents selected from R$^{13}$ or
R$^1$ is (1-6C)alkyl, halogen, cyano, (2-6C)alkenyl, (2-6C)alkynyl, (3-6C)cycloalkyl, (5-6C)cycloalkenyl, (2-5C)heterocycloalkyl or (2-5C)-heterocycloalkenyl;
R$^3$ is (di)[(1-6C)alkyl]amino, optionally substituted with hydroxy or
R$^3$ is a group selected from

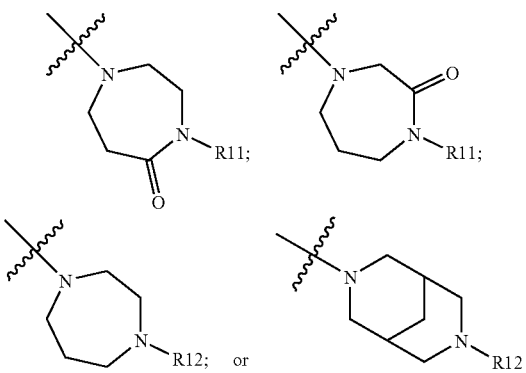

or
R$^3$ is (1-6C)alkyl, (3-6C)cycloalkyl, (di)[(1-4C)alkyl]amino(1-4C)alkyl or
R$^3$ is (2-6C)heterocycloalkyl; (2-6C)heterocycloalkyl(1-4C)alkyl, the (2-6C)heterocycloalkyl moiety of which optionally may be substituted with (1-4C)alkylcarbonyl or (3-6C)cycloalkylcarbonyl,
R$^3$ is pyrrolidin-1-yl, azepin-1-yl, 1,4-oxazepin-1-yl, all optionally substituted with one or more (1-4C)alkyl substituents
R$^8$ is H, (1-4C)alkyl, (1-4C)alkoxy, (1-4C)alkoxy(1-4C)alkyl, hydroxy or (2-4C)alkenyl;
R$^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino, formyl, cyano, nitro, (di)[(1-4C)alkyl]aminocarboxy, (1-6C)alkylcarbonyl, (1-4C)alkoxycarbonyl, (di)[(1-4C)alkyl]amino, (di)[(1-4C)

alkyl]aminocarbonylamino, (1-4C)alkoxycarbonylamino, (di)[(1-4C)alkyl]aminosulfonylamino, (1-6C)alkylthio or (1-4C)alkylsulfonylamino or $R^9$ is (1-6C)alkyl, (1-6C)alkoxy or (2-6C)alkenyl, all optionally substituted with one or more substituents selected from halogen, hydroxy, amine, azide, (1-4C)alkoxy, (1-4C)alkoxycarbonylamino or (1-4C)alkylcarbonylamino or $R^9$ is (1-5C)heteroaryl, phenyl, (2-5C)heteroaryloxy or phenoxy, all optionally substituted with one or more substituents selected from $R^{14}$ or $R^9$ is (1-6C)alkylcarbonylamino, optionally substituted with hydroxy, amino, (2-5C)heterocycloalkyl or (di)[(1-4C)alkyl]amino or $R^9$ is phenyl substituted at two adjacent positions together representing a fused O—$(CH_2)_m$—O ring wherein m is 1 or 2;

$R^{10}$ is H, methoxy, halogen or methyl $R^{11}$ is H, (1-4C)alkyl or (2-4C)alkenyl;

$R^{12}$ is (1-4C)alkylcarbonyl or (3-6C)cycloalkylcarbonyl, both optionally substituted with one or more substituents selected from $R^{15}$;

$R^{13}$ is hydroxy, amino, halogen, nitro, trifluoromethyl, cyano, (1-4C)alkyl, (1-4C)alkoxy, (1-4C)alkylthio or (di)[(1-4C)alkyl]amino;

$R^{14}$ is hydroxy, amino, halogen, nitro, trifluoromethyl, cyano, (1-4C)alkyl, (1-4C)alkoxy, (1-4C)alkylthio, (di)[(1-4C)alkyl]amino, (2-5C)heteroaryl, (di)[(1-4C)alkyl]aminocarbonyl, (1-4C)alkylcarbonylamino or (1-4C)alkylsulfonyl or $R^{14}$ is (2-5C)heterocycloalkyl optionally substituted with (1-4C)alkyl or (1-4C)alkoxycarbonyl; and $R^{15}$ is hydroxy, amino, halogen, nitro, trifluoromethyl, cyano, (1-4C)alkyl, (1-4C)alkoxy, (1-4C)alkylthio or (di)[(1-4C)alkyl]amino.

2. The compound according to claim 1 wherein $R^1$ is phenyl or (2-5C)heteroaryl, both optionally substituted with one or more substituents selected from $R^{13}$ or $R^1$ is (1-6C)alkyl, halogen, cyano, (2-6C)alkenyl, (2-6C)alkynyl, (3-6C)cycloalkyl, (5-6C)cycloalkenyl; and $R^3$ is (di)[(1-6C)alkyl]amino, optionally substituted with hydroxy or $R^3$ is a group selected from

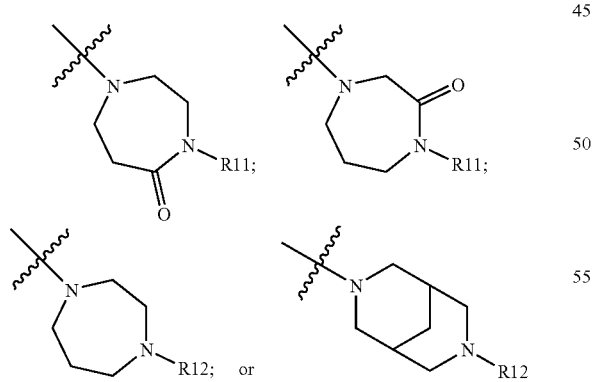

or $R^3$ is (1-6C)alkyl, (3-6C)cycloalkyl, (di)[(1-4C)alkyl]amino(1-4C)alkyl or $R^3$ is (2-6C)heterocycloalkyl(1-4C)alkyl, the (2-6C)heterocycloalkyl moiety of which optionally may be substituted with (1-4C)alkylcarbonyl or (3-6C)cycloalkylcarbonyl, or $R^3$ is pyrrolidin-1-yl, azepin-1-yl, 1,4-oxazepin-1-yl, all optionally substituted with one or more (1-4C)alkyl substituents $R^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino, formyl, cyano, nitro, (di)[(1-4C)alkyl]aminocarboxy, (1-6C)alkylcarbonyl, (1-4C)alkoxycarbonyl, (di)[(1-4C)alkyl]amino, (di)[(1-4C)alkyl]aminocarbonylamino, (1-4C)alkoxycarbonylamino, (di)[(1-4C)alkyl]aminosulfonylamino, (1-6C)alkylthio or (1-4C)alkylsulfonylamino or $R^9$ is (1-6C)alkyl, (1-6C)alkoxy or (2-6C)alkenyl, all optionally substituted with one or more substituents selected from halogen, hydroxy, amine, azide, (1-4C)alkoxy, (1-4C)alkoxycarbonylamino or (1-4C)alkylcarbonylamino or $R^9$ is (1-5C)heteroaryl, phenyl, (2-5C)heteroaryloxy or phenoxy, all optionally substituted with one or more substituents selected from $R^{14}$ or $R^9$ is (1-6C)alkylcarbonylamino, optionally substituted with hydroxy, amino, (2-5C)heterocycloalkyl or (di)[(1-4C)alkyl]amino.

3. The compound according to claim 1 wherein $R^1$ is phenyl or (2-5C)heteroaryl, both optionally substituted with one or more substituents selected from $R^{13}$ or $R^1$ is (1-6C)alkyl;

$R^3$ is (di)[(1-6C)alkyl]amino, optionally substituted with hydroxy or $R^3$ is a group selected from

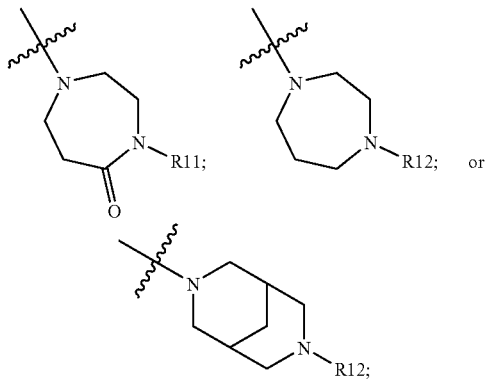

or $R^3$ is pyrrolidin-1-yl, optionally substituted with one or more (1-4C)alkyl substituents $R^8$ is H, (1-4C)alkyl, (1-4C)alkoxy or (2-4C)alkenyl;

$R^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino or (1-6C)alkylthio or $R^9$ is (1-6C)alkyl, (1-6C)alkoxy or (2-6C)alkenyl, all optionally substituted with one or more substituents selected from halogen, hydroxy, amine, azide, (1-4C)alkoxy, (1-4C)alkoxycarbonylamino or (1-4C)alkylcarbonylamino or $R^9$ is (1-5C)heteroaryl, phenyl, phenyloxy or (2-5C)heteroaryloxy, all optionally substituted with one or more substituents selected from $R^{14}$ or $R^9$ is (1-6C)alkylcarbonylamino, optionally substituted with hydroxy, amino, (2-5C)heterocycloalkyl or (di)[(1-4C)alkyl]amino or $R^9$ is phenyl substituted at two adjacent positions together representing dioxomethylene;

$R^{10}$ is H or halogen;

$R^{11}$ is (1-4C)alkyl or (2-4C)alkenyl;

$R^{12}$ is (1-4C)alkylcarbonyl or (3-6C)cycloalkylcarbonyl;

$R^{13}$ is halogen; and $R^{14}$ is amino, halogen, trifluoromethyl, cyano, (1-4C)alkyl, (1-4C)alkoxy, (di)[(1-4C)alkyl]amino, (2-5C)heteroaryl, (di)[(1-4C)alkyl]aminocarbonyl, (1-4C)alkylcarbonylamino or (1-4C)alkylsulfonyl or $R^{14}$ is (2-5C)heterocycloalkyl optionally substituted with (1-4C)alkoxycarbonyl.

4. The compounds according to claim 1 wherein $R^9$ is H, halogen, hydroxy, amino, (2-6C)alkynyl, (2-5C)heterocycloalkyl, (3-6C)cycloalkoxy, (2-5C)heterocycloalkoxy, (di)[(1-4C)alkyl]aminocarbonyl, (2-5C)heterocycloalkylcarbonyl, (2-5C)heteroarylaminocarbonyl, (2-5C)heterocycloalkylcarbonylamino, (2-5C)heteroarylcarbonylamino or (1-6C)alkylthio or $R^9$ is (1-6C)alkyl, (1-6C)alkoxy or (2-6C)alkenyl, all optionally substituted with one or more substituents selected from halogen, hydroxy, amine, azide, (1-4C)alkoxy, (1-4C)alkoxycarbonylamino or (1-4C)alkylcarbonylamino or $R^9$ is (1-5C)heteroaryl or phenyl, both optionally substituted with one or more substituents selected from $R^{14}$ or $R^9$ is (1-6C)alkylcarbonylamino, optionally substituted with hydroxy, amino, (2-5C)heterocycloalkyl or (di)[(1-4C)alkyl]amino.

5. The compound according to claim 1 wherein the C5-C6 bond is saturated.

6. The compound according to anyone of claim 1 wherein $R^1$ is (2-5C)heteroaryl.

7. The compound according to claim 6 wherein $R^1$ is thien-2-yl or thiazol-5-yl.

8. The compound according to claim 7 wherein $R^1$ is thien-2-yl.

9. The compound according to claim 1 wherein $R^3$ is (di)[(1-6C)alkyl]amino,

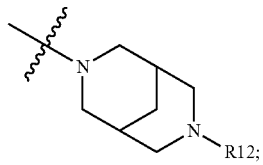 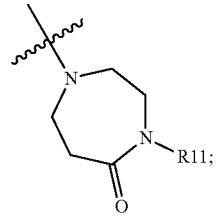

or pyrrolidin-1-yl, optionally substituted with one or more (1-4C)alkyl substituents.

10. The compound according to claim 9 wherein $R^{12}$ is (3-6C)cycloalkylcarbonyl.

11. The compound according to claim 1 wherein $R^8$ is (1-4C)alkoxy.

12. The compound according to claim 1 wherein $R^9$ is (1-6C)alkoxy, optionally substituted with hydroxyl; (1-6C)alkyl; (1-4C)alkenyl; (2-5C)heteroarylaminocarbonyl; (1-6C)alkylcarbonylamino, optionally substituted with (2-5C)heterocycloalkyl; or (1-5C)heteroaryl, or phenyl, both optionally substituted with one or more substituents selected from $R^{14}$.

13. The compound according to claim 12 wherein $R^{14}$ is amino, halogen, cyano, (1-4C)alkyl, (di)[(1-4C)alkyl]amino, (2-5C)heteroaryl, (1-4C)alkylcarbonylamino or (2-5C)heterocycloalkyl.

14. The compound according to anyone of claim 1 wherein $R^{10}$ is H.

15. The compound according to claim 1 wherein $R^{14}$ is amino, halogen, cyano, (1-4C)alkyl, (di)[(1-4C)alkyl]amino, (2-5C)heteroaryl, (1-4C)alkylcarbonylamino or (2-5C)heterocycloalkyl.

16. The compound according to claim 1 wherein $R^1$ is thien-2-yl, $R^3$ is (di)[(1-6C)alkyl]amino and $R^8$ is (1-4C)alkoxy.

17. The compound according to claim 1 wherein $R^8$ is methoxy.

18. A pharmaceutical composition which comprises a compound of formula I according to claim 1 or a pharmaceutically acceptable salt thereof and one or more pharmaceutically acceptable excipients.

19. A method of treating infertility in a patient in need of induced ovulation or controlled ovarian stimulation, the method comprising administering to the patient an effective amount of a compound of claim 1 or a pharmaceutically acceptable salt thereof.

* * * * *